United States Patent
Newton et al.

(10) Patent No.: US 8,669,208 B2
(45) Date of Patent: *Mar. 11, 2014

(54) HERBICIDAL BENZOXAZINONES

(75) Inventors: Trevor William Newton, Neustadt (DE); Thomas Seitz, Viernheim (DE); Matthias Witschel, Bad Duerkheim (DE); Anja Simon, Weinheim (DE); Helmut Walter, Obrigheim (DE); Richard Roger Evans, Limburgerhof (DE)

(73) Assignee: BASF SE, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/876,330

(22) PCT Filed: Sep. 26, 2011

(86) PCT No.: PCT/EP2011/066628
§ 371 (c)(1), (2), (4) Date: Mar. 27, 2013

(87) PCT Pub. No.: WO2012/041789
PCT Pub. Date: Apr. 5, 2012

(65) Prior Publication Data
US 2013/0184155 A1 Jul. 18, 2013

Related U.S. Application Data

(60) Provisional application No. 61/388,620, filed on Oct. 1, 2010.

(30) Foreign Application Priority Data

Oct. 1, 2010 (EP) .................................... 10185431

(51) Int. Cl.
| | | |
|---|---|---|
| *C07D 265/36* | (2006.01) | |
| *C07D 413/10* | (2006.01) | |
| *C07D 471/04* | (2006.01) | |
| *A01N 43/84* | (2006.01) | |
| *A01N 43/90* | (2006.01) | |

(52) U.S. Cl.
USPC .......................................... 504/225; 544/105

(58) Field of Classification Search
USPC .......................................... 544/105; 504/225
See application file for complete search history.

(56) References Cited

U.S. PATENT DOCUMENTS

| | | | |
|---|---|---|---|
| 5,080,710 A | 1/1992 | Rueb et al. | |
| 5,215,570 A | 6/1993 | Burckhardt et al. | |
| 5,529,974 A | 6/1996 | Kerber | |
| 5,532,203 A | 7/1996 | Foery et al. | |
| 6,235,680 B1 | 5/2001 | Ziemer et al. | |
| 8,445,407 B2 * | 5/2013 | Witschel et al. .............. 504/225 | |
| 2011/0015068 A1 | 1/2011 | Sievernich et al. | |
| 2011/0086762 A1 | 4/2011 | Fischer et al. | |
| 2013/0102463 A1 | 4/2013 | Ehrhardt et al. | |

FOREIGN PATENT DOCUMENTS

| | | |
|---|---|---|
| CN | 1687061 | 10/2005 |
| CN | 100386324 | 5/2008 |
| EP | 0 170 191 | 2/1986 |
| EP | 0365484 | 10/1989 |
| EP | 0 413 832 | 2/1991 |
| EP | 2103615 | 9/2009 |
| JP | 200 247975 | 9/2012 |
| WO | WO 90/06748 | 6/1990 |
| WO | WO 90/10626 | 8/1990 |
| WO | WO 92/06962 | 4/1992 |
| WO | WO 93/15074 | 8/1993 |
| WO | WO 94/03454 | 2/1994 |
| WO | WO 97/07104 | 2/1997 |
| WO | WO 9745016 | 12/1997 |
| WO | WO 02/066471 | 8/2002 |
| WO | WO 2010003444 | 1/2010 |
| WO | WO 2010040485 | 4/2010 |
| WO | WO 2010/145992 | 12/2010 |
| WO | WO 2011/018486 | 2/2011 |
| WO | WO 2011/051393 | 5/2011 |
| WO | WO 2011/057935 | 5/2011 |
| WO | WO 2012080239 | 6/2012 |

OTHER PUBLICATIONS

International Preliminary Report on Patentability dated Jan. 21, 2013, prepared in International Application No. PCT/EP2011/066628.
International Search Report dated Oct. 11, 2011, prepared in International Application No. PCT/EP2011/066628.
Naga et al., "Acid-Catalyzed Amino-Migration of O-Phenylhydroxylamines", J. Am. Chem. Soc., vol. 114, 1992, pp. 9795-9806.
Office Action, issued in co-pending U.S. Appl. No. 13/378,137, dated Sep. 13, 2013.
Office Action, issued in co-pending U.S. Appl. No. 13/993,137, dated Sep. 13, 2013.

* cited by examiner

Primary Examiner — Kahsay Habte
(74) Attorney, Agent, or Firm — Brinks Gilson & Lione

(57) ABSTRACT

The present invention provides benzoxazinones of formula I

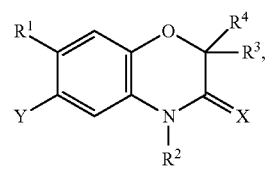

wherein
$R^1$ is hydrogen or halogen;
$R^2$ is hydrogen, $C_1$-$C_6$-alkyl, $C_1$-$C_6$-haloalkyl, $C_3$-$C_6$-cycloalkyl, $C_3$-$C_6$-alkenyl, $C_3$-$C_6$-haloalkenyl, $C_3$-$C_6$-alkynyl, $C_3$-$C_6$-haloalkynyl, $C_1$-$C_6$-alkoxy or $C_3$-$C_6$-cycloalkyl-$C_1$-$C_6$-alkyl;
$R^3$ is halogen;
$R^4$ is halogen;
X is O or S; and
Y is a substituted or unsubstituted heterocycle;
Benzoxazinones of formula I are useful as herbicides.

18 Claims, No Drawings

HERBICIDAL BENZOXAZINONES

This application is a National Stage application of International Application No. PCT/EP2011/066628, filed Sep. 26, 2011, which claims the benefit of U.S. Provisional Application No. 61/388,620, filed Oct. 1, 2010, the entire contents of which are hereby incorporated herein by reference. This application also claims priority under 35 U.S.C. §119 to European Patent Application No. 10185431.3, filed Oct. 1, 2010, the entire contents of which is hereby incorporated herein by reference.

The present invention relates to benzoxazinones of the general formula I defined below and to their use as herbicides. Moreover, the invention relates to compositions for crop protection and to a method for controlling unwanted vegetation.

WO 90/10626 and WO 97/07104 for example describe inter alia structurally similar compounds for which herbicidal action is stated, which differ from the benzoxazinones I according to the present invention in that the benzo[1,4]oxazine ring is preferably unsubstituted in the 2-position, whereas the benzoxazinones of formula I according to the present invention are substituted in said position by at least one halogen atom.

However, the herbicidal properties of these known compounds with regard to the harmful plants are not always entirely satisfactory.

It is therefore an object of the present invention to provide benzoxazinones having improved herbicidal action. To be provided are in particular benzoxazinones which have high herbicidal activity, in particular even at low application rates, and which are sufficiently compatible with crop plants for commercial utilization.

These and further objects are achieved by the benzoxazinones of the formula I, defined below, and by their agriculturally suitable salts.

Accordingly, the present invention provides benzoxazinones of formula I

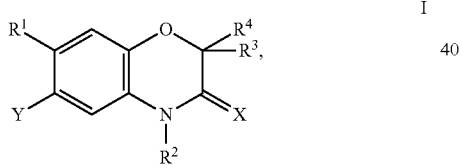

wherein
$R^1$ is hydrogen or halogen;
$R^2$ is hydrogen, $C_1$-$C_6$-alkyl, $C_1$-$C_6$-haloalkyl, $C_3$-$C_6$-cycloalkyl, $C_3$-$C_6$-alkenyl, $C_3$-$C_6$-haloalkenyl, $C_3$-$C_6$-alkynyl, $C_3$-$C_6$-haloalkynyl, $C_1$-$C_6$-alkoxy or $C_3$-$C_6$-cycloalkyl-$C_1$-$C_6$-alkyl;
$R^3$ is hydrogen or halogen;
$R^4$ is halogen;
X is O or S; and
Y is a substituent selected from the group consisting of $Y^1$ to $Y^{66}$:

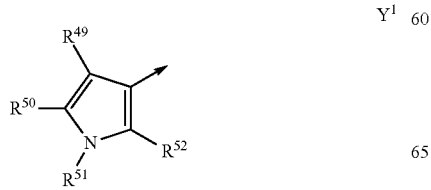

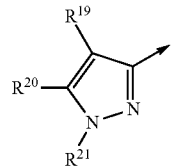

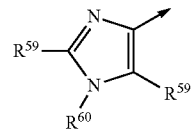

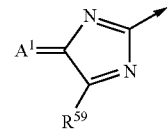

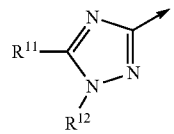

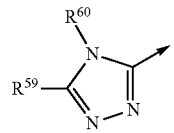

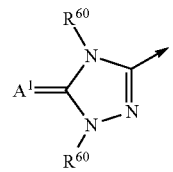

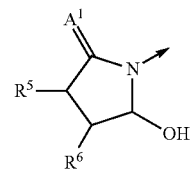

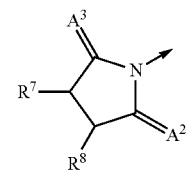

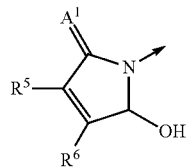

-continued
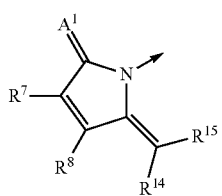 Y11
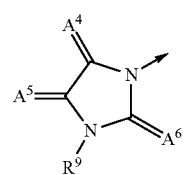 Y12
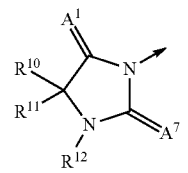 Y13
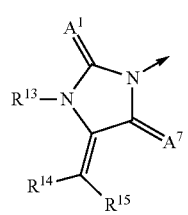 Y14
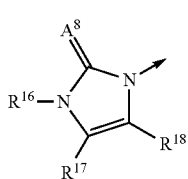 Y15
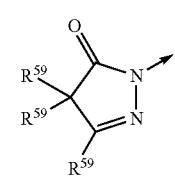 Y16
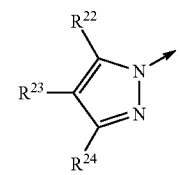 Y17
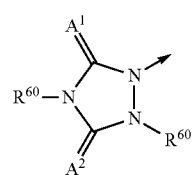 Y18
-continued
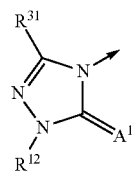 Y19
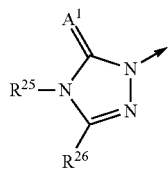 Y20
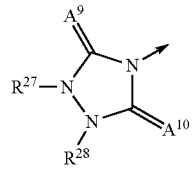 Y21
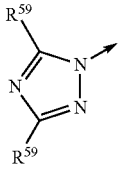 Y22
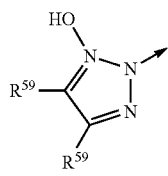 Y23
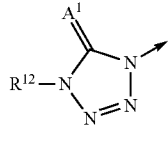 Y24
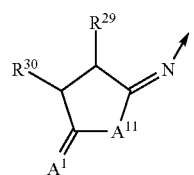 Y25
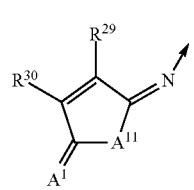 Y26
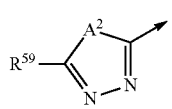 Y27

-continued
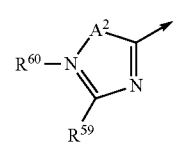  Y28
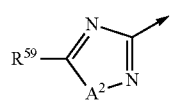  Y29
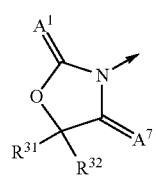  Y30
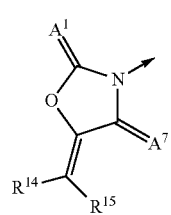  Y31
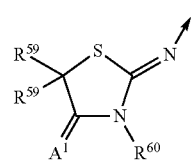  Y32
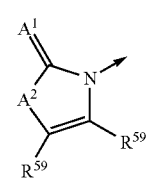  Y33
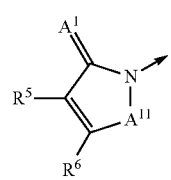  Y34
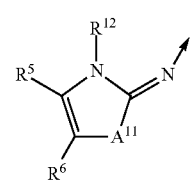  Y35
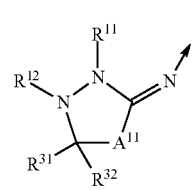  Y36
-continued
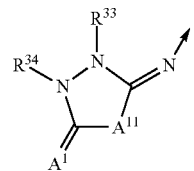  Y37
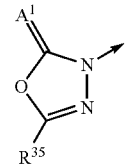  Y38
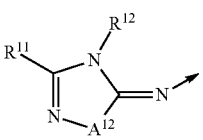  Y39
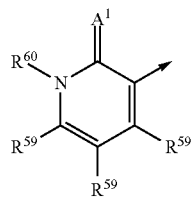  Y40
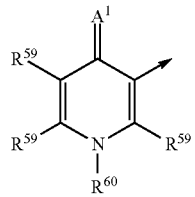  Y41
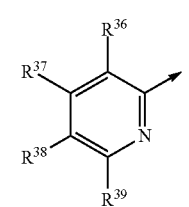  Y42
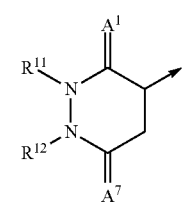  Y43
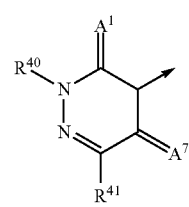  Y44

-continued
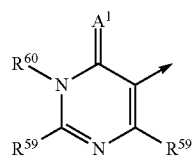 Y⁴⁵
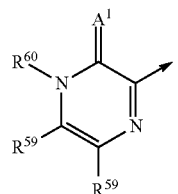 Y⁴⁶
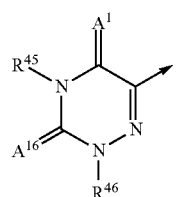 Y⁴⁷
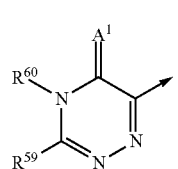 Y⁴⁸
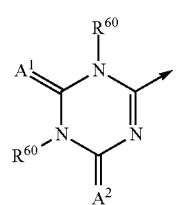 Y⁴⁹
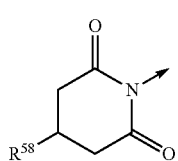 Y⁵⁰
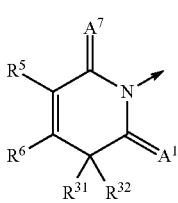 Y⁵¹
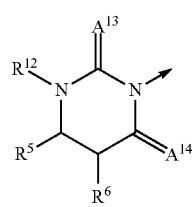 Y⁵²
-continued
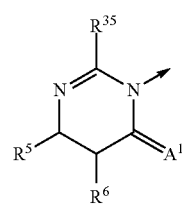 Y⁵³
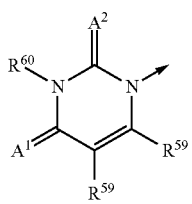 Y⁵⁴
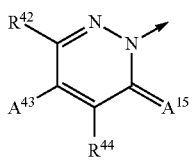 Y⁵⁵
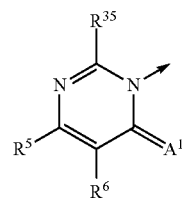 Y⁵⁶
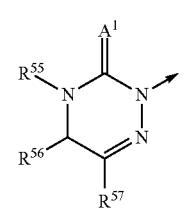 Y⁵⁷
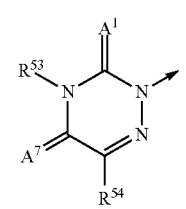 Y⁵⁸
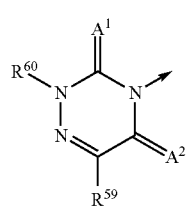 Y⁵⁹
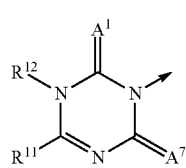 Y⁶⁰

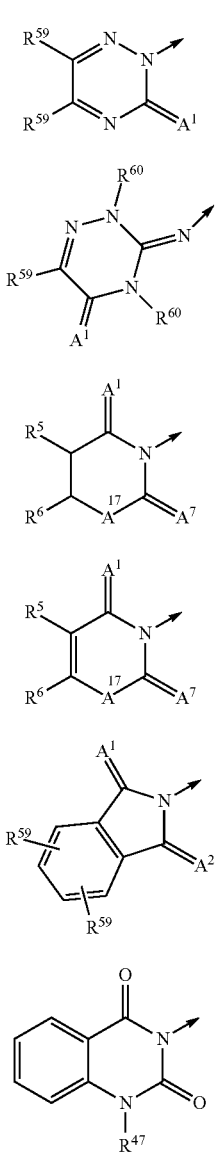

wherein
A$^1$ to A$^{10}$ are oxygen or sulfur;
A$^{11}$ is oxygen, sulphur, SO or SO$_2$;
A$^{12}$ to A$^{17}$ are oxygen or sulfur;
R$^5$, R$^6$, R$^7$, R$^8$, R$^{23}$, R$^{24}$, R$^{29}$, R$^{30}$, R$^{37}$, R$^{38}$, R$^{39}$, R$^{43}$, R$^{44}$, R$^{56}$ and R$^{58}$
are hydrogen, hydroxy, C$_1$-C$_6$-alkyl, C$_1$-C$_6$-haloalkyl, C$_3$-C$_7$-cycloalkyl, C$_3$-C$_7$-cycloalkyloxy, C$_1$-C$_6$-alkoxy, C$_1$-C$_6$-haloalkoxy, C$_2$-C$_6$-alkenyl, C$_2$-C$_6$-haloalkenyl, C$_2$-C$_6$-alkenyloxy, C$_3$-C$_6$-alkynyl, C$_3$-C$_6$-alkynyloxy, C$_1$-C$_6$-alkylthio, C$_1$-C$_6$-alkylsulfinyl, C$_1$-C$_6$-alkylsulfonyl, C$_1$-C$_6$-alkoxysulfonyl, C$_1$-C$_6$-alkylsulfonyloxy, amino, C$_1$-C$_6$-alkylamino or di(C$_1$-C$_6$-alkyl)amino; or
R$^5$ and R$^6$, R$^7$ and R$^8$, R$^{23}$ and R$^{24}$ or R$^{29}$ and R$^{30}$, together with the atoms to which they are attached, form a three- to six-membered cycle, which is saturated, partial unsaturated or aromatic, which may comprise apart from carbon atoms one to four nitrogen atoms, or one or two oxygen atoms, or one or two sulfur atoms, or one to three nitrogen atoms and an oxygen atom, or one to three nitrogen atoms and a sulfur atom, or one sulfur and one oxygen atom, and which for its part may be partially or fully halogenated and/or substituted by one to three radicals from the group consisting of C$_1$-C$_6$-alkyl and C$_1$-C$_6$-alkoxy;
R$^9$, R$^{10}$, R$^{11}$, R$^{12}$, R$^{16}$, R$^{17}$, R$^{20}$, R$^{21}$, R$^{25}$, R$^{26}$, R$^{27}$, R$^{28}$, R$^{33}$, R$^{34}$, R$^{40}$, R$^{45}$, R$^{46}$, R$^{50}$, R$^{51}$, R$^{53}$ and R$^{55}$ are hydrogen, cyano, hydroxy, C$_1$-C$_6$-alkyl, C$_1$-C$_6$-cyanoalkyl, C$_1$-C$_6$-haloalkyl, C$_3$-C$_7$-cycloalkyl, C$_3$-C$_7$-cycloalkyloxy, C$_1$-C$_6$-alkoxy, C$_1$-C$_6$-haloalkoxy, C$_2$-C$_6$-alkenyl, C$_2$-C$_6$-haloalkenyl, C$_2$-C$_6$-alkenyloxy, C$_3$-C$_6$-alkynyl, C$_3$-C$_6$-alkynyloxy, C$_1$-C$_6$-alkylsulfinyl, C$_1$-C$_6$-alkylsulfonyl, phenyl-C$_1$-C$_6$-alkyl, amino, C$_1$-C$_6$-alkylamino or di(C$_1$-C$_6$-alkyl)amino; or
R$^{11}$ and R$^{12}$, R$^{16}$ and R$^{17}$, R$^{25}$ and R$^{26}$, R$^{27}$ and R$^{28}$, or R$^{33}$ and R$^{34}$, together with the atoms to which they are attached, form a three- to six-membered cycle, which is saturated, partial unsaturated or aromatic, which may comprise apart from carbon atoms one to four nitrogen atoms, or one or two oxygen atoms, or one or two sulfur atoms, or one to three nitrogen atoms and an oxygen atom, or one to three nitrogen atoms and a sulfur atom, or one sulfur and one oxygen atom, and which for its part may be partially or fully halogenated and/or substituted by one to three radicals from the group consisting of C$_1$-C$_6$-alkyl and C$_1$-C$_6$-alkoxy;
R$^{13}$ is hydrogen, C$_1$-C$_6$-alkyl, C$_1$-C$_6$-haloalkyl, C$_2$-C$_6$-alkenyl, C$_3$-C$_6$-alkynyl, C$_1$-C$_6$-haloalkoxy, amino, C$_1$-C$_6$-alkylamino or di(C$_1$-C$_6$-alkyl)amino;
R$^{14}$, R$^{15}$, R$^{18}$, R$^{22}$, R$^{31}$ and R$^{32}$
are hydrogen, halogen or C$_1$-C$_6$-alkyl;
R$^{19}$, R$^{35}$, R$^{36}$, R$^{41}$, R$^{42}$, R$^{49}$, R$^{52}$, R$^{54}$ and R$^{57}$
are hydrogen, halogen, hydroxy, C$_1$-C$_6$-alkyl, C$_1$-C$_6$-haloalkyl, C$_3$-C$_7$-cycloalkyl, C$_3$-C$_7$-cycloalkyloxy, C$_1$-C$_6$-alkoxy, C$_1$-C$_6$-haloalkoxy, C$_1$-C$_6$-alkylthio, C$_1$-C$_6$-haloalkylthio, C$_2$-C$_6$-alkenyl, C$_2$-C$_6$-haloalkenyl, C$_2$-C$_6$-alkenyloxy, C$_3$-C$_6$-alkynyl or C$_3$-C$_6$-alkynyloxy; and
R$^{47}$ is hydrogen, NH$_2$, C$_1$-C$_6$-alkyl or C$_3$-C$_6$-alkynyl;
R$^{59}$ is hydrogen, amino, nitro, cyano, carboxy, carbamoyl, thiocarbamoyl, halogen, C$_1$-C$_6$-alkyl, C$_1$-C$_6$-haloalkyl, C$_3$-C$_7$-cycloalkyl, C$_3$-C$_7$-cycloalkyloxy, C$_1$-C$_6$-alkoxy, C$_1$-C$_6$-haloalkoxy, C$_1$-C$_6$-alkylthio, C$_1$-C$_6$-haloalkylthio, C$_2$-C$_6$-alkenyl, C$_2$-C$_6$-haloalkenyl, C$_2$-C$_6$-alkenyloxy, C$_3$-C$_6$-alkynyl, C$_3$-C$_6$-alkynyloxy, C$_1$-C$_6$-alkoxycarbonyl, C$_2$-C$_6$-alkenylthio, C$_3$-C$_6$-alkynylthio, C$_1$-C$_6$-alkylamino, di(C$_1$-C$_6$-alkyl)amino or C$_3$-C$_7$-cycloalkyl-C$_1$-C$_3$-alkyl;
R$^{60}$ is hydrogen, hydroxyl, amino, cyano, C$_1$-C$_6$-alkyl, C$_1$-C$_6$-haloalkyl, C$_3$-C$_7$-cycloalkyl, C$_3$-C$_7$-cycloalkyloxy, C$_1$-C$_6$-alkoxy, C$_1$-C$_6$-haloalkoxy, C$_2$-C$_6$-alkenyl, C$_3$-C$_6$-alkynyl, C$_1$-C$_6$-alkoxycarbonyl, C$_1$-C$_6$-alkylamino, di(C$_1$-C$_6$-alkyl)amino, C$_3$-C$_7$-cycloalkyl-C$_1$-C$_3$-alkyl, phenyl or phenyl-C$_1$-C$_6$-alkyl;
wherein in case Y is Y$^2$ or Y$^{20}$, R$^3$ and R$^4$ both are halogen;
including their agriculturally acceptable salts.

The present invention also provides herbicidally active compositions comprising at least one benzoxazinone of formula I and at least one further compound selected from herbicidal active compounds B and safeners C.

The present invention also provides the use of benzoxazinones of the general formula I as herbicides, i.e. for controlling harmful plants.

The present invention also provides mixtures comprising at least one benzoxazinone of the formula I and auxiliaries customary for formulating crop protection agents.

The present invention furthermore provides a method for controlling unwanted vegetation where a herbicidal effective amount of at least one benzoxazinone of the formula I is allowed to act on plants, their seeds and/or their habitat. Application can be done before, during and/or after the emergence of the undesirable plants.

Moreover, the invention relates to processes and intermediates for preparing benzoxazinones of the formula I.

Further embodiments of the present invention are evident from the claims, the description and the examples. It is to be understood that the features mentioned above and still to be illustrated below of the subject matter of the invention can be applied not only in the combination given in each particular case but also in other combinations, without leaving the scope of the invention.

As used herein, the terms "controlling" and "combating" are synonyms.

As used herein, the terms "undesirable vegetation" and "harmful plants" are synonyms.

If the benzoxazinones of formula I as described herein are capable of forming geometrical isomers, for example E/Z isomers, it is possible to use both, the pure isomers and mixtures thereof, in the compositions according to the invention.

If the benzoxazinones of formula I as described herein have one or more centers of chirality and, as a consequence, are present as enantiomers or diastereomers, it is possible to use both the pure enantiomers and diastereomers and their mixtures in the compositions according to the invention.

If the benzoxazinones of formula I as described herein have functional groups, which can be ionized, they can also be used in the form of their agriculturally acceptable salts or mixtures thereof.

In general, the salts of those cations are suitable whose cations have no adverse effect on the action of the active compounds ("agricultural acceptable"). Preferred cations are the ions of the alkali metals, preferably of lithium, sodium and potassium, of the alkaline earth metals, preferably of calcium and magnesium, and of the transition metals, preferably of manganese, copper, zinc and iron, furthermore ammonium and substituted ammonium (hereinafter also termed as organoammonium) in which one to four hydrogen atoms are replaced by $C_1$-$C_4$-alkyl, hydroxy-$C_1$-$C_4$-alkyl, hydroxy-$C_1$-$C_4$-alkoxy-$C_1$-$C_4$-alkyl, phenyl or benzyl, preferably ammonium, methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyethoxy)eth-1-ylammonium, di(2-hydroxyeth-1-yl)ammonium, benzyltrimethylammonium, benzyltriethylammonium, furthermore phosphonium ions, sulfonium ions, preferably tri($C_1$-$C_4$-alkyl)sulfonium such as trimethyl-sulfonium, and sulfoxonium ions, preferably tri($C_1$-$C_4$-alkyl)sulfoxonium.

Anions of useful acid addition salts are primarily chloride, bromide, fluoride, iodide, hydrogen sulfate, methyl sulfate, sulfate, dihydrogen phosphate, hydrogen phosphate, nitrate, bicarbonate, carbonate, hexafluorosilicate, hexafluorophosphate, benzoate and the anions of $C_1$-$C_4$-alkanoic acids, preferably formate, acetate, propionate and butyrate.

The organic moieties mentioned in the definition of the variables mentioned herein, especially with regard to $R^1$ to $R^{46}$, are—like the term halogen—collective terms for individual enumerations of the individual group members. The term halogen denotes in each case fluorine, chlorine, bromine or iodine. All hydrocarbon chains, i.e. all alkyl, can be straight-chain or branched, the prefix $C_n$-$C_m$ denoting in each case the possible number of carbon atoms in the group.

Examples of such meanings are:

$C_1$-$C_4$-alkyl: for example $CH_3$, $C_2H_5$, n-propyl, and $CH(CH_3)_2$ n-butyl, $CH(CH_3)$—$C_2H_5$, $CH_2$—$CH(CH_3)_2$ and $C(CH_3)_3$;

$C_1$-$C_6$-alkyl and also the $C_1$-$C_6$-alkyl moieties of $C_1$-$C_6$-cycanoalkyl, $C_1$-$C_6$-cycloalkyl-$C_1$-$C_6$-alkyl, $C_1$-$C_6$-alkylsulfinyl, $C_1$-$C_6$-alkylsulfonyl, $C_1$-$C_6$-alkylsulfonyloxy, and phenyl-$C_1$-$C_6$-alkyl: $C_1$-$C_4$-alkyl as mentioned above, and also, for example, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl, preferably methyl, ethyl, n-propyl, 1-methylethyl, n-butyl, 1,1-dimethylethyl, n-pentyl or n-hexyl;

$C_1$-$C_4$-haloalkyl: a $C_1$-$C_4$-alkyl radical as mentioned above which is partially or fully substituted by fluorine, chlorine, bromine and/or iodine, for example, chloromethyl, di-chloromethyl, trichloromethyl, fluoromethyl, difluoromethyl, trifluoromethyl, chlorofluoromethyl, dichlorofluoromethyl, chlorodifluoromethyl, bromomethyl, iodomethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl, nonafluorobutyl, 1,1,2,2,-tetrafluoroethyl and 1-trifluoromethyl-1,2,2,2-tetrafluoroethyl;

$C_1$-$C_6$-haloalkyl and also the $C_1$-$C_6$-haloalkyl moieties of $C_1$-$C_6$-haloalkylthio: $C_1$-$C_4$-haloalkyl as mentioned above, and also, for example, 5-fluoropentyl, 5-chloropentyl, 5-bromopentyl, 5-iodopentyl, undecafluoropentyl, 6-fluorohexyl, 6-chlorohexyl, 6-bromohexyl, 6-iodohexyl and trisdecafluorohexyl;

$C_3$-$C_6$-cycloalkyl and also the cycloalkyl moieties of $C_3$-$C_6$-cycloalkyl-$C_1$-$C_6$-alkyl: monocyclic saturated hydrocarbons having 3 to 6 ring members, such as cyclopropyl, cyclobutyl, cyclopentyl and cyclohexyl;

$C_3$-$C_7$-cycloalkyl and also the cycloalkyl moieties of $C_3$-$C_7$-cycloalkyloxy: monocyclic saturated hydrocarbons having 3 to 7 ring members, such as cyclopropyl, cyclobutyl, cyclopentyl, cyclohexyl and cycloheptyl;

$C_3$-$C_6$-alkenyl: for example 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

$C_2$-$C_6$-alkenyl and the alkenyl moieties of $C_2$-$C_6$-alkenyloxy: $C_3$-$C_6$-alkenyl as mentioned above, and also ethenyl;

$C_2$-$C_6$-haloalkenyl: a $C_2$-$C_6$-alkenyl radical as mentioned above which is partially or fully substituted by fluorine, chlorine, bromine and/or iodine, for example 2-chloroprop-2-en-1-yl, 3-chloroprop-2-en-1-yl, 2,3-dichloroprop-2-en-1-yl, 3,3-dichloroprop-2-en-1-yl, 2,3,3-trichloro-2-en-1-yl, 2,3-dichlorobut-2-en-1-yl, 2-bromoprop-2-en-1-yl, 3-bromoprop-2-en-1-yl, 2,3-dibromoprop-2-en-1-yl, 3,3-dibromoprop-2-en-1-yl, 2,3,3-tribromo-2-en-1-yl or 2,3-dibromobut-2-en-1-yl;

$C_3$-$C_6$-alkynyl and also the $C_3$-$C_6$-alkynyl moieties of $C_3$-$C_6$-alkynyloxy: for example 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl;

$C_3$-$C_6$-haloalkynyl: a $C_3$-$C_6$-alkynyl radical as mentioned above which is partially or fully substituted by fluorine, chlorine, bromine and/or iodine, for example 1,1-difluoroprop-2-yn-1-yl, 3-chloroprop-2-yn-1-yl, 3-bromoprop-2-yn-1-yl, 3-iodoprop-2-yn-1-yl, 4-fluorobut-2-yn-1-yl, 4-chlorobut-2-yn-1-yl, 1,1-difluorobut-2-yn-1-yl, 4-iodobut-3-yn-1-yl, 5-fluoropent-3-yn-1-yl, 5-iodopent-4-yn-1-yl, 6-fluorohex-4-yn-1-yl or 6-iodohex-5-yn-1-yl;

$C_1$-$C_4$-alkoxy: for example methoxy, ethoxy, propoxy, 1-methylethoxy butoxy, 1-methylpropoxy, 2-methylpropoxy and 1,1-dimethylethoxy;

$C_1$-$C_6$-alkoxy and also the $C_1$-$C_6$-alkoxy moieties of $C_1$-$C_6$-haloalkoxy, $C_1$-$C_6$-alkoxysulfonyl: $C_1$-$C_4$-alkoxy as mentioned above, and also, for example, pentoxy, 1-methylbutoxy, 2-methylbutoxy, 3-methoxybutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy;

$C_1$-$C_4$-alkylthio: for example methylthio, ethylthio, propylthio, 1-methylethylthio, butylthio, 1-methylpropylthio, 2-methylpropylthio and 1,1-dimethylethylthio;

$C_1$-$C_6$-alkylthio: $C_1$-$C_4$-alkylthio as mentioned above, and also, for example, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio;

$C_1$-$C_6$-alkylamino: for example methylamino, ethylamino, propylamino, 1-methylethylamino, butylamino, 1-methylpropylamino, 2-methylpropylamino, 1,1-dimethylethylamino, pentylamino, 1-methylbutylamino, 2-methylbutylamino, 3-methylbutylamino, 2,2-dimethylpropylamino, 1-ethylpropylamino, hexylamino, 1,1-dimethylpropylamino, 1,2-dimethylpropylamino, 1-methylpentylamino, 2-methylpentylamino, 3-methylpentylamino, 4-methylpentylamino, 1,1-dimethylbutylamino, 1,2-dimethylbutylamino, 1,3-dimethylbutylamino, 2,2-dimethylbutylamino, 2,3-dimethylbutylamino, 3,3-dimethylbutylamino, 1-ethylbutylamino, 2-ethylbutylamino, 1,1,2-trimethylpropylamino, 1,2,2-trimethylpropylamino, 1-ethyl-1-methylpropylamino or 1-ethyl-2-methylpropylamino;

di($C_1$-$C_4$-alkyl)amino: for example N,N-dimethylamino, N,N-diethylamino, N,N-dipropylamino, N,N-di(1-methylethyl)amino, N,N-dibutylamino, N,N-di(1-methylpropyl)amino, N,N-di(2-methylpropyl)amino, N,N-di(1,1-dimethylethyl)amino, N-ethyl-N-methylamino, N-methyl-N-propylamino, N-methyl-N-(1-methylethyl)amino, N-butyl-N-methylamino, N-methyl-N-(1-methylpropyl)amino, N-methyl-N-(2-methylpropyl)amino, N-(1,1-dimethylethyl)-N-methylamino, N-ethyl-N-propylamino, N-ethyl-N-(1-methylethyl)amino, N-butyl-N-ethylamino, N-ethyl-N-(1-methylpropyl)amino, N-ethyl-N-(2-methylpropyl)amino, N-ethyl-N-(1,1-dimethylethyl)amino, N-(1-methylethyl)-N-propylamino, N-butyl-N-propylamino, N-(1-methylpropyl)-N-propylamino, N-(2-methylpropyl)-N-propylamino, N-(1,1-dimethylethyl)-N-propylamino, N-butyl-N-(1-methylethyl)amino, N-(1-methylethyl)-N-(1-methylpropyl)amino, N-(1-methylethyl)-N-(2-methylpropyl)amino, N-(1,1-dimethylethyl)-N-(1-methylethyl)amino, N-butyl-N-(1-methylpropyl)amino, N-butyl-N-(2-methylpropyl)amino, N-butyl-N-(1,1-dimethylethyl)amino, N-(1-methylpropyl)-N-(2-methylpropyl)amino, N-(1,1-dimethylethyl)-N-(1-methylpropyl)amino and N-(1,1-dimethylethyl)-N-(2-methylpropyl)amino;

di($C_1$-$C_6$-alkyl)amino: di($C_1$-$C_4$-alkyl)amino as mentioned above, and also, for example, N,N-dipentylamino, N,N-dihexylamino, N-methyl-N-pentylamino, N-ethyl-N-pentylamino, N-methyl-N-hexylamino and N-ethyl-N-hexylamino;

a three- to six-membered cycle, which is saturated, partial unsaturated or aromatic, which may comprise apart from carbon atoms one to four nitrogen atoms, or one or two oxygen atoms, or one or two sulfur atoms, or one to three nitrogen atoms and an oxygen atom, or one to three nitrogen atoms and a sulfur atom, or one sulfur and one oxygen atom, for example:

cyclopropyl, cyclobutyl, cyclopentyl, cyclohexyl;

1-cyclopropenyl, 2-cyclopropenyl, 1-cyclobutenyl, 2-cyclobutenyl, 1-cyclopentenyl, 2-cyclopentenyl, 1,3-cyclopentadienyl, 1,4-cyclopentadienyl, 2,4-cyclopentadienyl, 1-cyclohexenyl, 2-cyclohexenyl, 3-cyclohexenyl, 1,3-cyclohexadienyl, 1,4-cyclohexadienyl, 2,5-cyclohexadienyl; phenyl;

oxiranyl, oxetanyl, aziridinyl, thiiranyl, thiethanyl, azetidinyl, azetinyl;

tetrahydrofuranyl, tetrahydrothienyl, pyrrolidinyl, isoxazolidinyl, isothiazolidinyl, pyrazolidinyl, oxazolidinyl, thiazolidinyl, imidazolidinyl, triazolidinyl, oxadiazolidinyl, thiadiazolidinyl;

dihydrofuryl, dioxolanyl, dihydrothienyl, dihydropyrrolyl, dihydroisoxazol, dihydroisothiazolyl, dihydropyrazolyl, dihydroimidazolyl, dihydrooxazolyl, dihydrothiazolyl; furyl, thienyl, pyrrolyl, pyrazolyl, isoxazolyl, isothiazolyl, imidazolyl, oxazolyl, thiazolyl, oxadiazolyl, thiadiazol, triazolyl, tetrazolyl;

piperidinyl, dioxanyl, dithianyl, dithianyl, oxathianyl, tetrahydropyranyl, tetrahydrothiopyranyl, hexahydropyridazinyl, hexahydropyrimidinyl, piperazinyl, hexahydrotriazinyl, tetrahydrooxazinyl, morpholinyl;

pyranyl, thiopyranyl, dihydrooxazinyl, dihydropyranyl, dihydrothiopyranyl, tetrahydropyridinyl, dihydropyridinyl, dihydrothiazinyl, tetrahydropyridazinyl, tetrahydropyrimidinyl, tetrahydropyrazinyl, oxazinyl, thiazinyl, dihydropyridazinyl, dihydropyrazinyl, dihydropyrimidinyl;

pyridinyl, pyridazinyl, pyrimidin, pyrazinyl, triazinyl, tetrazinyl.

The preferred embodiments of the invention mentioned herein below have to be understood as being preferred either independently from each other or in combination with one another.

According to a preferred embodiment of the invention preference is also given to those benzoxazinones of formula I, wherein the variables, either independently of one another or in combination with one another, have the following meanings:

$R^1$ is hydrogen;
  is also preferably halogen,
  particularly preferred F or Cl,
  especially preferred F;

$R^2$ is $C_3$-$C_6$-alkynyl or $C_3$-$C_6$-haloalkynyl,
  preferably $C_3$-alkynyl or $C_3$-haloalkynyl,
  particularly preferred $CH_2C\equiv CH$, $CH_2C\equiv CCl$ or $CH_2C\equiv CBr$;
  is also preferably $C_3$-$C_6$-alkynyl or $C_3$-$C_6$-cycloalkyl-$C_1$-$C_6$-alkyl,
  particularly preferred propargyl or cyclopropylmethyl;
  is also preferably $C_3$-$C_6$-alkynyl, preferably $C_3$-alkynyl;
  particularly preferred $CH_2C\equiv CH$;
  is also preferably $C_3$-$C_6$-haloalkynyl, preferably $C_3$-haloalkynyl,
  particularly preferred $CH_2C\equiv CCl$ or $CH_2C\equiv CBr$;

$R^3$ is hydrogen;
  is also preferably halogen; particularly preferred F or Cl;
    more preferably Cl;
  is also preferably halogen, particularly preferred F;
  is also preferably hydrogen or F;

$R^4$ is hydrogen;
  is also preferably halogen; particularly preferred F or Cl;
    more preferably Cl;
  is also preferably halogen, particularly preferred F;
  is also preferably hydrogen or F;

X is O,
  is also preferably S;

Y is preferably $Y^2$, $Y^{13}$, $Y^{12}$, $Y^{20}$, $Y^{31}$, $Y^{37}$, $Y^{38}$, $Y^{39}$, $Y^{42}$, $Y^{55}$ or $Y^{66}$;
  is more preferably $Y^{12}$, $Y^{13}$, $Y^{20}$, $Y^{31}$, $Y^{37}$, $Y^{38}$, $Y^{39}$, $Y^{55}$ or $Y^{66}$;
  is still more preferably $Y^2$, $Y^{42}$, $Y^{55}$;
  is most preferably $Y^{55}$;

$A^1$ to $A^{10}$ preferably are oxygen;
  also preferably are sulphur;

$A^{11}$ preferably is oxygen or sulphur,
  more preferably is oxygen;
  also more preferably is sulphur;
  also preferably is oxygen, SO or $SO_2$;
  also preferably is sulphur, SO or $SO_2$;
  also more preferably is SO or $SO_2$;

$A^{12}$ to $A^{17}$ preferably are oxygen;
  also preferably are sulphur;

$R^5$, $R^6$, $R^7$, $R^8$, $R^{23}$, $R^{24}$, $R^{29}$, $R^{30}$, $R^{37}$, $R^{38}$, $R^{39}$, $R^{43}$, $R^{44}$, $R^{56}$ and $R^{58}$
  preferably are $C_1$-$C_6$-alkyl, $C_1$-$C_6$-haloalkyl, alkylthio, $C_1$-$C_6$-, $C_1$-$C_6$-alkylsulfonyl, or $R^5$ and $R^6$, $R^7$ and $R^8$, $R^{23}$ and $R^{24}$ or $R^{29}$ and $R^{30}$, together with the atoms to which they are attached, form a five- to six-membered cycle, which is saturated, partial unsaturated or aromatic, which may comprise apart from carbon atoms one to four nitrogen atoms, or one oxygen atoms, or one sulfur atoms, and which for its part may be partially or fully halogenated and/or substituted by one to three $C_1$-$C_6$-alkyl groups;
  more preferably are $C_1$-$C_6$-alkyl, $C_1$-$C_6$-haloalkyl, or $R^5$ and $R^6$, $R^7$ and $R^8$, $R^{23}$ and $R^{24}$ or $R^{29}$ and $R^{30}$ together with the atoms to which they are attached, form a five- to six-membered cycle, which is saturated, partial unsaturated or aromatic, and which for its part may be substituted by one or two halogen atoms, preferably fluorine, and/or substituted by one to three $C_1$-$C_4$-alkyl groups, preferably methyl;
  particularly preferably are $C_1$-$C_6$-alkyl or $C_1$-$C_6$-haloalkyl;
  also particularly preferred $R^5$ and $R^6$, $R^7$ and $R^8$, $R^{23}$ and $R^{24}$ or $R^{29}$ and $R^{30}$ together with the atoms to which they are attached, form a five- to six-membered cycle, which is saturated, partial unsaturated or aromatic, and which for its part may be substituted by one or two halogen atoms, preferably fluorine, and/or substituted by one to three $C_1$-$C_4$-alkyl groups, preferably methyl;

$R^{38}$ and $R^{43}$ are most preferably $C_1$-$C_6$-haloalkyl;

$R^{44}$ is most preferably $CH_3$;

$R^9$, $R^{10}$, $R^{11}$, $R^{12}$, $R^{16}$, $R^{17}$, $R^{20}$, $R^{21}$, $R^{25}$, $R^{26}$, $R^{27}$, $R^{28}$, $R^{33}$, $R^{34}$, $R^{40}$, $R^{45}$, $R^{46}$, $R^{50}$, $R^{51}$, $R^{53}$ and $R^{55}$
  preferably are hydrogen, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylsulfinyl, $C_1$-$C_6$-alkylsulfonyl, or $R^{11}$ and $R^{12}$, $R^{16}$ and $R^{17}$, $R^{25}$ and $R^{26}$, $R^{27}$ and $R^{28}$, or $R^{33}$ and $R^{34}$, together with the atoms to which they are attached, form a five- to six-membered cycle, which is saturated, partial unsaturated or aromatic, which may comprise apart from carbon atoms one to four nitrogen atoms, or one or two oxygen atoms, or one or two sulfur atoms, and which for its part may be partially or fully halogenated;
  more preferably are hydrogen, $C_1$-$C_6$-alkyl, $C_1$-$C_6$-haloalkyl, $C_1$-$C_6$-alkylsulfonyl, or $R^{11}$ and $R^{12}$, $R^{16}$ and $R^{17}$, $R^{25}$ and $R^{26}$, $R^{27}$ and $R^{28}$, or $R^{33}$ and $R^{34}$, together with the atoms to which they are attached, form a five- to six-membered cycle, which is saturated, partial unsaturated or aromatic, and which for its part may be substituted by one or two halogen atoms, preferably fluorine, and/or substituted by one to three $C_1$-$C_4$-alkyl groups, preferably methyl;
particularly preferred are hydrogen, $C_1$-$C_6$-alkyl, $C_1$-$C_6$-haloalkyl or $C_1$-$C_6$-alkylsulfonyl;
$R^{20}$ is most preferably $CF_3$, $OCHF_2$;
$R^{21}$ is most preferably Cl, Br, $CH_3$;
also particularly preferred $R^{11}$ and $R^{12}$, $R^{16}$ and $R^{17}$, $R^{25}$ and $R^{26}$, $R^{27}$ and $R^{28}$, or $R^{33}$ and $R^{34}$, together with the atoms to which they are attached, form a five- to six-membered cycle, which is saturated, partial unsaturated or aromatic, and which for its part may be substituted by one or two halogen atoms, preferably fluorine, and/or substituted by one to three $C_1$-$C_4$-alkyl groups, preferably methyl;
$R^{13}$ is preferably $C_1$-$C_6$-alkyl or $C_1$-$C_6$-haloalkyl;
$R^{14}$, $R^{15}$, $R^{18}$, $R^{22}$, $R^{31}$ and $R^{32}$
preferably are hydrogen, halogen or $C_1$-$C_6$-alkyl;
more preferably are halogen or $C_1$-$C_6$-alkyl;
most preferably are halogen;
also most preferably are $C_1$-$C_6$-alkyl;
also most preferably are hydrogen;
$R^{19}$, $R^{35}$, $R^{36}$, $R^{41}$, $R^{42}$, $R^{49}$, $R^{52}$, $R^{54}$ and $R^{57}$
preferably are hydrogen, halogen or $C_1$-$C_6$-alkyl;
more preferably are halogen or $C_1$-$C_6$-alkyl;
most preferably are halogen;
also most preferably are $C_1$-$C_6$-alkyl;
also most preferably are hydrogen;
$R^{36}$ is most preferably F, Cl;
$R^{47}$ preferably is $C_1$-$C_6$-alkyl;
$R^{59}$ preferably is hydrogen, halogen, $C_1$-$C_6$-alkyl or $C_1$-$C_6$-haloalkyl;
more preferably is $C_1$-$C_6$-alkyl;
$R^{60}$ preferably is hydrogen, amino, $C_1$-$C_6$-alkyl or $C_1$-$C_6$-haloalkyl;
more preferably is $C_1$-$C_6$-alkyl.

Particular preference is given to benzoxazinones of formula I, wherein X is O and Y is $Y^{55}$, wherein $A^{15}$ is O, $R^{42}$ is H, $R^{43}$ is $CF_3$, $R^{44}$ is $CH_3$, and which herein below are also referred to as benzoxazinones of formula Ia.

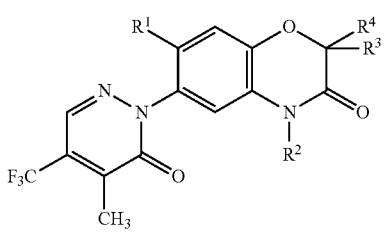

Ia wherein the variables $R^1$, $R^2$, $R^3$ and $R^4$ have the meanings, in particular the preferred meanings, as defined above.

Special preference is given to benzoxazinones of the formulae Ia1 to Ia60 of table A, where the definitions of the variables $R^1$, $R^2$, $R^3$ and $R^4$ are of particular importance for the compounds according to the invention not only in combination with one another but in each case also on their own:

TABLE A

| no. | $R^1$ | $R^2$ | $R^3$ | $R^4$ |
|---|---|---|---|---|
| Ia1 | H | H | H | F |
| Ia2 | H | $CH_3$ | H | F |
| Ia3 | H | $C_2H_5$ | H | F |
| Ia4 | H | $CH_2$—$C_2H_5$ | H | F |
| Ia5 | H | $CH(CH_3)_2$ | H | F |
| Ia6 | H | $CH_2$—$CH_2$—$(CH_3)_2$ | H | F |
| Ia7 | H | $CH_2$—CH=$CH_2$ | H | F |
| Ia8 | H | $CH_2$C≡CH | H | F |
| Ia9 | H | $CH_2$C≡C—Cl | H | F |
| Ia10 | H | $CH_2$C≡C—Br | H | F |
| Ia11 | F | H | H | F |
| Ia12 | F | $CH_3$ | H | F |
| Ia13 | F | $C_2H_5$ | H | F |
| Ia14 | F | $CH_2$—$C_2H_5$ | H | F |
| Ia15 | F | $CH(CH_3)_2$ | H | F |
| Ia16 | F | $CH_2$—$CH_2$—$(CH_3)_2$ | H | F |
| Ia17 | F | $CH_2$—CH=$CH_2$ | H | F |
| Ia18 | F | $CH_2$C≡CH | H | F |
| Ia19 | F | $CH_2$C≡C—Cl | H | F |
| Ia20 | F | $CH_2$C≡C—Br | H | F |
| Ia21 | Cl | H | H | F |
| Ia22 | Cl | $CH_3$ | H | F |
| Ia23 | Cl | $C_2H_5$ | H | F |
| Ia24 | Cl | $CH_2$—$C_2H_5$ | H | F |
| Ia25 | Cl | $CH(CH_3)_2$ | H | F |
| Ia26 | Cl | $CH_2$—$CH_2$—$(CH_3)_2$ | H | F |
| Ia27 | Cl | $CH_2$—CH=$CH_2$ | H | F |
| Ia28 | Cl | $CH_2$C≡CH | H | F |
| Ia29 | Cl | $CH_2$C≡C—Cl | H | F |
| Ia30 | Cl | $CH_2$C≡C—Br | H | F |
| Ia31 | H | H | F | F |
| Ia32 | H | $CH_3$ | F | F |
| Ia33 | H | $C_2H_5$ | F | F |
| Ia34 | H | $CH_2$—$C_2H_5$ | F | F |
| Ia35 | H | $CH(CH_3)_2$ | F | F |
| Ia36 | H | $CH_2$—$CH_2$—$(CH_3)_2$ | F | F |
| Ia37 | H | $CH_2$—CH=$CH_2$ | F | F |
| Ia38 | H | $CH_2$C≡CH | F | F |
| Ia39 | H | $CH_2$C≡C—Cl | F | F |
| Ia40 | H | $CH_2$C≡C—Br | F | F |
| Ia41 | F | H | F | F |
| Ia42 | F | $CH_3$ | F | F |
| Ia43 | F | $C_2H_5$ | F | F |
| Ia44 | F | $CH_2$—$C_2H_5$ | F | F |
| Ia45 | F | $CH(CH_3)_2$ | F | F |
| Ia46 | F | $CH_2$—$CH_2$—$(CH_3)_2$ | F | F |
| Ia47 | F | $CH_2$—CH=$CH_2$ | F | F |
| Ia48 | F | $CH_2$C≡CH | F | F |
| Ia49 | F | $CH_2$C≡C—Cl | F | F |
| Ia50 | F | $CH_2$C≡C—Br | F | F |
| Ia51 | Cl | H | F | F |
| Ia52 | Cl | $CH_3$ | F | F |
| Ia53 | Cl | $C_2H_5$ | F | F |
| Ia54 | Cl | $CH_2$—$C_2H_5$ | F | F |
| Ia55 | Cl | $CH(CH_3)_2$ | F | F |
| Ia56 | Cl | $CH_2$—$CH_2$—$(CH_3)_2$ | F | F |
| Ia57 | Cl | $CH_2$—CH=$CH_2$ | F | F |
| Ia58 | Cl | $CH_2$C≡CH | F | F |
| Ia59 | Cl | $CH_2$C≡C—Cl | F | F |
| Ia60 | Cl | $CH_2$C≡C—Br | F | F |

Also preferred are the benzoxazinones of formula Ib, particularly preferred the benzoxazinones of formulae Ib1 to Ib60, which differ from the corresponding benzoxazinones of formulae Ia1 to Ia60 only in that Y is $Y^{13}$, wherein $A^1$ and $A^7$ are O, $R^{10}$ is $CH_3$ and $R^{11}$ and $R^{12}$ together form —($CH_2$—CHF—$CH_2$)—, preferably $R^{11}$ and $R^{12}$ together form the (6S,7aR) stereoisomer:

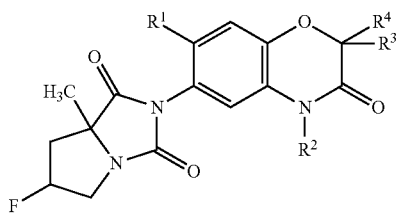

Ib

Also preferred are the benzoxazinones of formula Ic, particularly preferred the benzoxazinones of formulae Ic1 to Ic60, which differ from the corresponding benzoxazinones of formulae Ia1 to Ia60 only in that Y is $Y^{20}$, wherein $A^1$ is O and $R^{25}$ and $R^{26}$ together form —$(CH_2)_4$—:

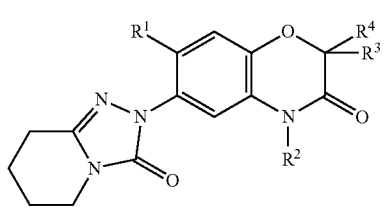

Ic

Also preferred are the benzoxazinones of formula Id, particularly preferred the benzoxazinones of formulae Id1 to Id60, which differ from the corresponding benzoxazinones of formulae Ia1 to Ia60 only in that Y is $Y^{20}$, wherein $A^1$ is O, $R^{25}$ is $CHF_2$ and $R^{26}$ is $CH_3$:

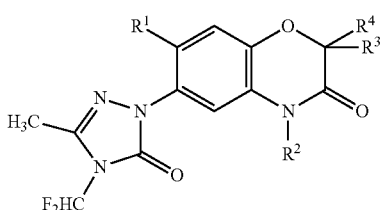

Id

Also preferred are the benzoxazinones of formula Ie, particularly preferred the benzoxazinones of formulae Ie1 to Ie60, which differ from the corresponding benzoxazinones of formulae Ia1 to Ia60 only in that Y is $Y^{31}$, wherein $A^1$ and $A^7$ are O, and $R^{14}$ and $R^{15}$ are $CH_3$:

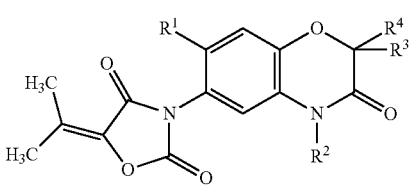

Ie

Also preferred are the benzoxazinones of formula If, particularly preferred the benzoxazinones of formulae If1 to If60, which differ from the corresponding benzoxazinones of formulae Ia1 to Ia60 only in that Y is $Y^{37}$, wherein $A^1$ is O, $A^{11}$ is S and $R^{33}$ and $R^{34}$ together form —$(CH_2)_4$—:

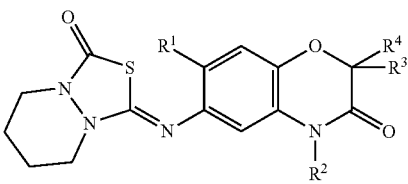

If

Also preferred are the benzoxazinones of formula Ig, particularly preferred the benzoxazinones of formulae Ig1 to Ig60, which differ from the corresponding benzoxazinones of formulae Ia1 to Ia60 only in that Y is $Y^{38}$, wherein $A^1$ is O and $R^{35}$ is $C(CH_3)_3$:

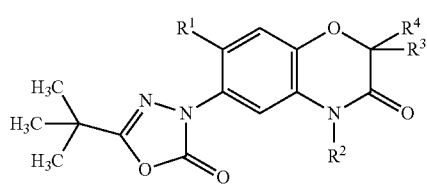

Ig

Also preferred are the benzoxazinones of formula Ih, particularly preferred the benzoxazinones of formulae Ih1 to Ih60, which differ from the corresponding benzoxazinones of formulae Ia1 to Ia60 only in that Y is $Y^{39}$, wherein $A^{12}$ is S and $R^{11}$ and $R^{12}$ together form —$CH_2$—$C(CH_3)_2$—$CH_2$—:

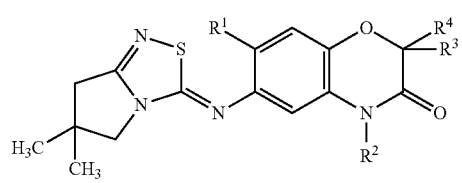

Ih

Also preferred are the benzoxazinones of formula Ii, particularly preferred the benzoxazinones of formulae Ii1 to Ii60, which differ from the corresponding benzoxazinones of formulae Ia1 to Ia60 only in that Y is $Y^{12}$, wherein $A^4$, $A^5$ and $A^6$ are O and $R^9$ is —$CH_2$—$CH_2$—$CH_3$:

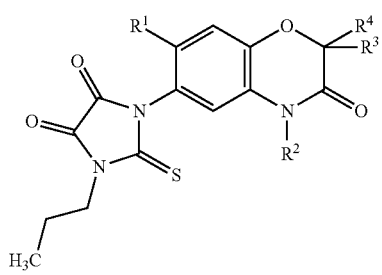

Ii

Also preferred are the benzoxazinones of formula Ik, particularly preferred the benzoxazinones of formulae Ik1 to Ik60, which differ from the corresponding benzoxazinones of formulae Ia1 to Ia60 only in that Y is $Y^{66}$, wherein $R^{47}$ is $CH_3$ and $R^{48}$ is H:

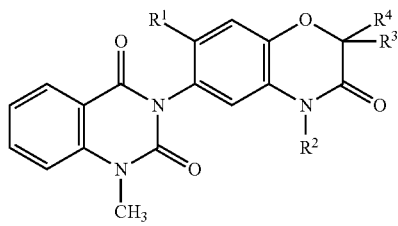

Ik

Also preferred are the benzoxazinones of formula Im, particularly preferred the benzoxazinones of formulae Im1 to Im60, which differ from the corresponding benzoxazinones of formulae Ia1 to Ia60 only in that Y is $Y^2$, wherein $R^{19}$ is Cl, $R^{20}$ is $CF_3$ and $R^{21}$ is $CH_3$:

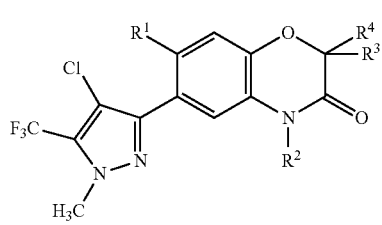

Im

Also preferred are the benzoxazinones of formula In, particularly preferred the benzoxazinones of formulae In1 to In60, which differ from the corresponding benzoxazinones of formulae Ia1 to Ia60 only in that Y is $Y^2$, wherein $R^{19}$ is Br, $R^{20}$ is $CF_3$ and $R^{21}$ is $CH_3$:

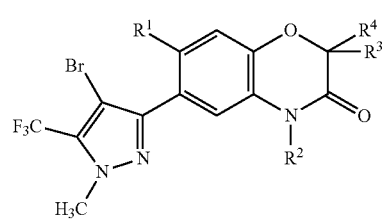

In

Also preferred are the benzoxazinones of formula Io, particularly preferred the benzoxazinones of formulae Io1 to Io60, which differ from the corresponding benzoxazinones of formulae Ia1 to Ia60 only in that Y is $Y^2$, wherein $R^{19}$ is Cl, $R^{20}$ is $OCHF_2$ and $R^{21}$ is $CH_3$:

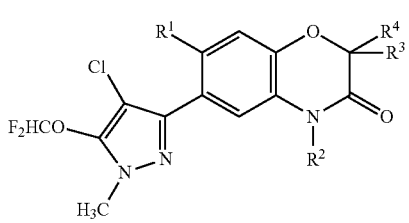

Io

Also preferred are the benzoxazinones of formula Ip, particularly preferred the benzoxazinones of formulae Ip1 to Ip60, which differ from the corresponding benzoxazinones of formulae Ia1 to Ia60 only in that Y is $Y^2$, wherein $R^{19}$ is Br, $R^{20}$ is $OCHF_2$ and $R^{21}$ is $CH_3$:

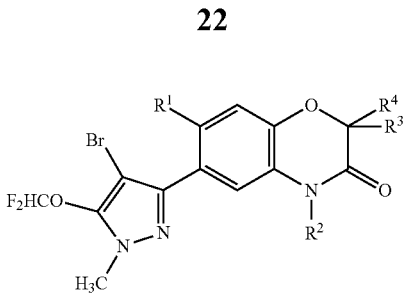

Ip

Also preferred are the benzoxazinones of formula Iq, particularly preferred the benzoxazinones of formulae Iq1 to Iq60, which differ from the corresponding benzoxazinones of formulae Ia1 to Ia60 only in that Y is $Y^{42}$, wherein $R^{36}$ is F, $R^{37}$ is H, $R^{38}$ is $CF_3$ and $R^{39}$ is H:

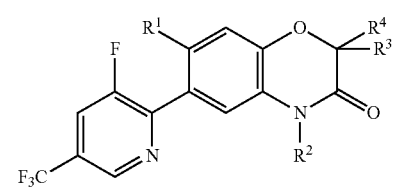

Iq

Also preferred are the benzoxazinones of formula Ir, particularly preferred the benzoxazinones of formulae Ir1 to Ir60, which differ from the corresponding benzoxazinones of formulae Ia1 to Ia60 only in that Y is $Y^{13}$, wherein $A^1$ and $A^7$ are O, $R^{10}$ is hydrogen and $R^{11}$ and $R^{12}$ together form —($CH_2$—CHF—$CH_2$)—, preferably $R^{11}$ and $R^{12}$ together form the (6S,7aR) stereoisomer:

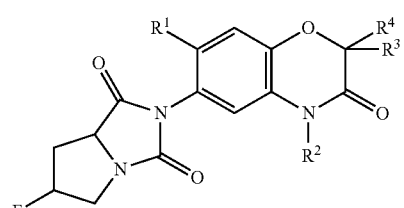

Ir

The benzoxazinones of formula I according to the invention can be prepared by standard processes of organic chemistry, for example via the nitro-compounds III and the amines II as shown below:

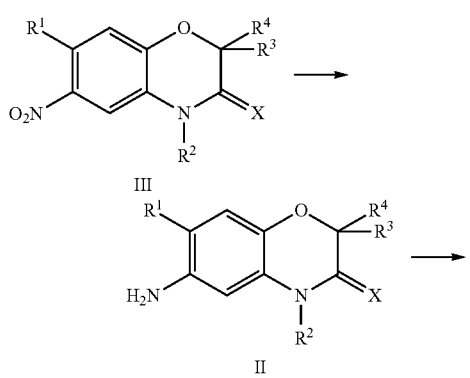

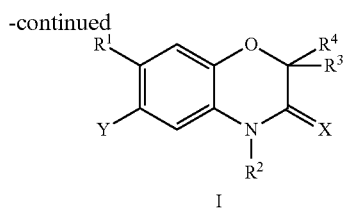

I

Preferred is the amino compound IIa (=amino compound II wherein $R^4$ is fluorine and X is O):

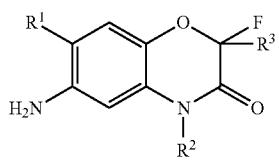

The reduction of the nitro compounds III is usually carried out at from 20° C. to the boiling point of the reaction mixture, preferably at from 20° C. to 200° C., particularly preferably at from 20° C. to 100° C., in an inert organic solvent (Organikum, Heidelberg, 1993, pages 320-323).

Suitable reducing agents are nascent $H_2$; hydrogen in the presence of catalytic amounts of transition metals or transition metal compounds, in particular those of the $8^{th}$ transition group, preferably Ni, Pd, Pt, Ru or Rh, either as such, in supported form e.g. supported via activated carbon, Al, $ZrO_2$, $TiO_2$, $SiO_2$, carbonates and the like, or in compounds such as palladium oxide or platinum oxide; or metal hydrides, semimetal hydrides such as aluminium hydride and hydrides derived therefrom such as lithium aluminium hydride, diisobutylaluminiumhydride, borohydrides such as diborane or boranates derived therefrom such as sodium borohydride or lithium borohydride.

Suitable solvents are aliphatic hydrocarbons such as pentane, hexane, cyclohexane and mixtures of $C_5$-$C_8$-alkanes, aromatic hydrocarbons such as toluene, o-, m- and p-xylene, ethers such as diethyl ether, diisopropyl ether, tert.-butyl methyl ether, dioxane, anisole and tetrahydrofuran, glycol ethers such as dimethyl glycol ether, diethyl glycol ether, diethylene glycol dimethyl ether, esters such as ethyl acetate, propyl acetate, methyl isobutyrate, isobutyl acetate, carboxamides such as N,N-dimethylformamide, N-methylpyrrolidone, N,N-dimethylacetamide, nitriles such as acetonitrile and propionitrile, alcohols such as methanol, ethanol, n-propanol, isopropanol, n-butanol and tert.-butanol, Particular preference is given to toluene and methanol.

It is also possible to use mixtures of the solvents mentioned.

Work up can be carried out in a known manner.

The methods used to convert the amines II to the compounds I depend on the nature of the group, Y. For each value of Y, the method of preparation is identical to that used for the preparation of the corresponding compounds I, in which $R^3$ and $R^4$ are H, starting from the compounds II, in which $R^3$ and $R^4$ also are H. These methods are described inter alia in JP 2009137851 ($Y^{45}$), CN 1687061 ($Y^{51}$), CN 1597681 ($Y^{12}$), WO 04/087694 ($Y^{65}$), CN 1515560 ($Y^{12}$), CN 1355164 ($Y^{66}$), CN 1355163 ($Y^{56}$), CN 1325849 ($Y^{12}$), WO 02/070476 ($Y^1$), WO 02/042275 ($Y^{42}$), WO 02/038562 ($Y^{20}$), WO 020/24704 ($Y^{21}$), EP 1157991 ($Y^{12}$), EP 1095935 ($Y^{52}$), WO 01/000602 ($Y^{13}$), JP 2000219679 ($Y^{17}$), JP 11292720 ($Y^{15}$), EP 902029 ($Y^{56}$), EP 863142 ($Y^{13}$), WO 98/14452 ($Y^{56}$), WO 98/07720 ($Y^{42}$), WO 97/47626 ($Y^{14}$), WO 93/15074 ($Y^1$, $Y^2$, $Y^3$, $Y^5$), WO 94/14817 ($Y^{21}$), WO 97/28127 ($Y^{40}$, $Y^{41}$), WO 97/11060 ($Y^{46}$), WO 97/07104 ($Y^{55}$), WO 97/06150 ($Y^{45}$), WO 94/05668 ($Y^{13}$), WO 96/20195 ($Y^{14}$), WO 96/18618 ($Y^{21}$), WO 96/02523 ($Y^{37}$), EP 688773 ($Y^{13}$), EP 683160 ($Y^{35}$), JP 07304759 ($Y^{32}$), WO 95/22547 ($Y^2$, $Y^{12}$, $Y^{20}$), WO 95/23509 ($Y^{13}$), EP 640600 ($Y^{60}$), WO 92/06962 ($Y^2$), WO 93/15074 ($Y^3$), JP 06016664 ($Y^{33}$), EP 568041 ($Y^{56}$), WO 93/19065 ($Y^{13}$), JP 05213970 ($Y^{37}$), JP 05140155 ($Y^{56}$), WO 93/03043 ($Y^{39}$), WO 92/21684 ($Y^{37}$), JP 04145087 ($Y^{37}$), WO 92/06962 ($Y^2$), WO 92/02509 ($Y^2$), EP 454444 ($Y^{58}$), EP 448188 ($Y^{39}$), JP 03081275 ($Y^2$), EP 422639 ($Y^{17}$), EP 415642 ($Y^{50}$), DE 3922107 ($Y^{14}$, $Y^{31}$), WO 90/10626 ($Y^{31}$), EP 371240 ($Y^{63}$, $Y^{64}$), EP 334055 ($Y^{17}$, $Y^{20}$, $Y^{38}$), EP 349832 ($Y^{21}$), EP 338533 ($Y^{14}$, $Y^{31}$), EP 328001 ($Y^{31}$), JP 01139580 ($Y^{11}$, $Y^{17}$, $Y^{55}$), EP 311135 ($Y^{13}$, $Y^{17}$, $Y^{21}$, $Y^{38}$, $Y^{39}$), EP 305923 ($Y^{23}$), U.S. Pat. No. 4,830,659 ($Y^{37}$), EP 304935 ($Y^{17}$), EP 304920 ($Y^{37}$), JP 63222167 ($Y^1$), WO 88/05264 ($Y^{20}$), EP 273417 ($Y^{37}$) and EP 176101 ($Y^{37}$).

The nitro compounds III in turn can be obtained from the corresponding phenyl compounds IV:

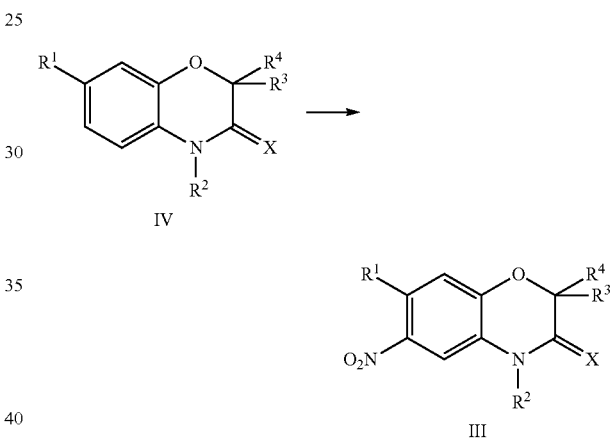

The nitration of the phenyl compound IV is usually carried out at from −20° C. to 100° C., particularly preferably at from 0° C. to 20° C. (Organikum, Heidelberg, 1993, pages 553-557).

Suitable nitrating agents are mixtures of $H_2SO_{4\ conc}$ and $HNO_{3\ conc}$, preferably in a range of 50:1 to 1:50, more preferably 20:1 to 1:20, especially preferred in a range of 10:1 to 1:10.

Work up can be carried out in a known manner.

Those nitro compounds III, wherein $R^2$ is $C_3$-$C_6$-alkenyl, $C_3$-$C_6$-haloalkenyl, $C_3$-$C_6$-alkynyl or $C_3$-$C_6$-haloalkynyl, preferably $C_3$-$C_6$-alkynyl, can also be prepared by alkylation of nitro compounds III, wherein $R^2$ is H:

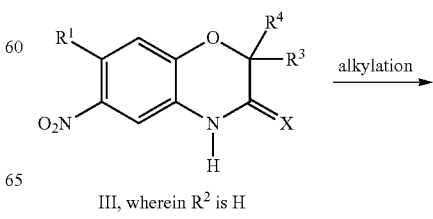

III, wherein $R^2$ is H

-continued

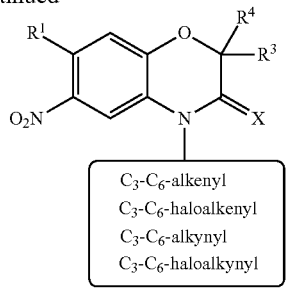

III, wherein R² is

C₃-C₆-alkenyl,   C₃-C₆-haloalkenyl
C₃-C₆-alkynyl,   C₃-C₆-haloalkynyl

This reaction is usually carried out at from −78° C. to the boiling point of the reaction mixture, preferably at from −40° C. to 100° C., particularly preferably at from −20° C. to 30° C., in an inert organic solvent in the presence of a base [WO 02/066471].

Suitable solvents are aliphatic hydrocarbons such as pentane, hexane, cyclohexane and mixtures of $C_5$-$C_8$-alkanes, aromatic hydrocarbons such as toluene, o-, m- and p-xylene, halogenated hydrocarbons such as dichloromethane, 1,2-dichloroethane, chloroform and chlorobenzene, ethers such as diethyl ether, diisopropyl ether, tert.-butyl methyl ether, dioxane, anisole and tetrahydrofuran, glycol ethers such as dimethyl glycol ether, diethyl glycol ether, diethylene glycol dimethyl ether, esters such as ethyl acetate, propyl acetate, methyl isobutyrate, isobutyl acetate, carboxamides such as N,N-dimethylformamide, N-methylpyrrolidone, N,N-dimethylacetamide, nitriles such as acetonitrile and propionitrile, ketones such as acetone, methyl ethyl ketone, diethyl ketone and tert-butyl methyl ketone, as well as dimethylsulfoxide. Particular preference is given to ethers such as diethyl ether, diisopropyl ether, tert.-butyl methyl ether, dioxane, anisole and tetrahydrofuran. It is also possible to use mixtures of the solvents mentioned.

Suitable bases are, in general inorganic compounds such as alkali metal and alkaline earth metal hydrides such as lithium hydride, sodium hydride, potassium hydride and calcium hydride, alkali metal and alkaline earth metal carbonates such as lithium carbonate, potassium carbonate and calcium carbonate, as well as alkali metal bicarbonates such as sodium bicarbonate, alkali metal and alkaline earth metal alkoxides such as sodium methoxide, sodium ethoxide, potassium ethoxide, potassium tert-butoxide, potassium tert-pentoxide and dimethoxymagnesium, and furthermore organic bases, such as tertiary amines such as trimethylamine, triethylamine, diisopropylethyl-amine and N-methylpiperidine, pyridine, substituted pyridines such as collidine, lutidine, N-methylmorpholine and 4-dimethylaminopyridine and also bicyclic amines. Particular preference is given to tertiary amines such as trimethylamine, triethylamine, diisopropyl-ethyl-amine and alkali metal and alkaline earth metal alkoxides such as sodium methoxide, sodium ethoxide, potassium ethoxide, The bases are generally employed in catalytic amounts; however they can also be employed in equimolar amounts, in excess or, if appropriate, be used as solvent.

Work up can be carried out in a known manner.

The phenyl compounds IV in turn can be obtained from the corresponding acetamides V:

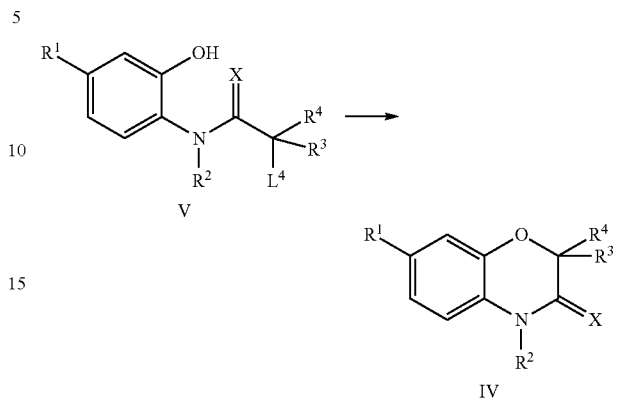

The cyclisation of the acetamide V is usually carried out at from 0° C. to the boiling point of the reaction mixture, preferably at from 0° C. to 140° C., particularly preferably at from 20° C. to 120° C., in an inert organic solvent in the presence of a base [WO 02/066471].

$L^4$ is halogen selected from Cl, Br, I; preferably Cl or Br; most preferably Cl, also most preferably Br.

Suitable solvents are aliphatic hydrocarbons such as pentane, hexane, cyclohexane and mixtures of $C_5$-$C_8$-alkanes, aromatic hydrocarbons such as toluene, o-, m- and p-xylene, halogenated hydrocarbons such as dichloromethane, 1,2-dichloroethane, chloroform and chlorobenzene, ethers such as diethyl ether, diisopropyl ether, tert.-butyl methyl ether, dioxane, anisole and tetrahydrofuran, glycol ethers such as dimethyl glycol ether, diethyl glycol ether, diethylene glycol dimethyl ether, esters such as ethyl acetate, propyl acetate, methyl isobutyrate, isobutyl acetate, carboxamides such as N,N-dimethylformamide, N-methylpyrrolidone, N,N-dimethylacetamide, nitriles such as acetonitrile and propionitrile, as well as dimethylsulfoxide.

It is also possible to use mixtures of the solvents mentioned.

Suitable bases are, in general Inorganic compounds such as alkali metal and alkaline earth metal hydroxides such as lithium hydroxide, sodium hydroxide, potassium hydroxide and calcium hydroxide, alkali metal and alkaline earth metal oxide such as lithium oxide, sodium oxide, calcium oxide and magnesium oxide, alkali metal and alkaline earth metal hydrides such as lithium hydride, sodium hydride, potassium hydride and calcium hydride, alkali metal and alkaline earth metal carbonates such as lithium carbonate, potassium carbonate and calcium carbonate, as well as alkali metal bicarbonates such as sodium bicarbonate, metal organic compounds, preferably alkali metal alkyls such as methyl lithium, butyl lithium and phenyl lithium, alkyl magnesium halides such as methyl magnesium chloride as well as alkali metal and alkaline earth metal alkoxides such as sodium methoxide, sodium ethoxide, potassium ethoxide, potassium tert-butoxide, potassium tert-pentoxide and dimethoxymagnesium, and furthermore organic bases, such as tertiary amines such as trimethylamine, triethylamine, diisopropylethyl-amine and N-methylpiperidine, pyridine, substituted pyridines such as collidine, lutidine, N-methylmorpholine and 4-dimethylaminopyridine and also bicyclic amines. Particular preference is given to 1,8-Diazabicyclo[5.4.0]undec-7-en (DBU).

The bases are generally employed in catalytic amounts, however they can also be employed in equimolar amounts, in excess or, if appropriate, be used as solvent.

Work up can be carried out in a known manner.

The acetamides V in turn can be obtained from the corresponding phenol VI:

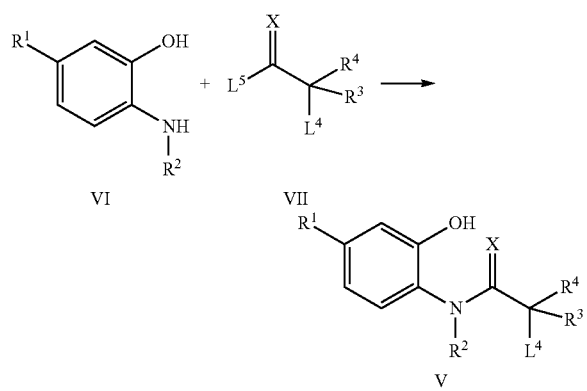

This reaction is usually carried out at from −78° C. to the boiling point of the reaction mixture, preferably at from −40° C. to 100° C., particularly preferably at from −20° C. to 30° C., in an inert organic solvent in the presence of a base [WO 02/066471].

$L^4$ is halogen selected from Cl, Br, I; preferably Cl or Br; most preferably Cl, also most preferably Br.

$L^5$ is a known activating group for acylations, e.g. halogen or $C_1$-$C_6$-alkoxy, preferably Cl or $C_1$-$C_6$-alkoxy, most preferably Cl, $OCH_3$ or $OC_2H_5$.

Suitable solvents are aliphatic hydrocarbons such as pentane, hexane, cyclohexane and mixtures of $C_3$-$C_8$-alkanes, aromatic hydrocarbons such as toluene, o-, m- and p-xylene, halogenated hydrocarbons such as dichloromethane, 1,2-dichloroethane, chloroform and chlorobenzene, ethers such as diethyl ether, diisopropyl ether, tert.-butyl methyl ether, dioxane, anisole and tetrahydrofuran, glycol ethers such as dimethyl glycol ether, diethyl glycol ether, diethylene glycol dimethyl ether, esters such as ethyl acetate, propyl acetate, methyl isobutyrate, isobutyl acetate, carboxamides such as N,N-dimethylformamide, N-methylpyrrolidone, N,N-dimethylacetamide, nitriles such as acetonitrile and propionitrile, ketones such as acetone, methyl ethyl ketone, diethyl ketone and tert-butyl methyl ketone, as well as dimethylsulfoxide.

Particular preference is given to ethers such as diethyl ether, diisopropyl ether, tert.-butyl methyl ether, dioxane, anisole and tetrahydrofuran.

It is also possible to use mixtures of the solvents mentioned.

Suitable bases are, in general inorganic compounds such as alkali metal and alkaline earth metal hydrides such as lithium hydride, sodium hydride, potassium hydride and calcium hydride, alkali metal and alkaline earth metal carbonates such as lithium carbonate, potassium carbonate and calcium carbonate, as well as alkali metal bicarbonates such as sodium bicarbonate, alkali metal and alkaline earth metal alkoxides such as sodium methoxide, sodium ethoxide, potassium ethoxide, potassium tert-butoxide, potassium tert-pentoxide and dimethoxymagnesium, and furthermore organic bases, such as tertiary amines such as trimethylamine, triethylamine, diisopropylethyl-amine and N-methylpiperidine, pyridine, substituted pyridines such as collidine, lutidine, N-methylmorpholine and 4-dimethylaminopyridine and also bicyclic amines.

Particular preference is given to tertiary amines such as trimethylamine, triethylamine, diisopropylethylamine and alkali metal and alkaline earth metal alkoxides such as sodium methoxide, sodium ethoxide, potassium ethoxide, The bases are generally employed in catalytic amounts, however they can also be employed in equimolar amounts, in excess or, if appropriate, be used as solvent.

Work up can be carried out in a known manner.

The phenols VI required for the preparation of the acetamides V are known from the literature (WO 02/066471) or they can be prepared in accordance with the literature cited and/or are commercially available.

The compounds VII required for the preparation of the acetamides V are commercially available.

The benzoxazinones of formula I and compositions comprising them are suitable as herbicides. They are suitable as such or as an appropriately formulated composition The herbicidal compositions comprising the benzoxazinones of formula I control vegetation on non-crop areas very efficiently, especially at high rates of application. They act against broad-leaved weeds and grass weeds in crops such as wheat, rice, maize, soya and cotton without causing any significant damage to the crop plants. This effect is mainly observed at low rates of application.

Depending on the application method in question, the benzoxazinones of formula I or compositions comprising them can additionally be employed in a further number of crop plants for eliminating undesirable plants. Examples of suitable crops are the following:

*Allium cepa, Ananas comosus, Arachis hypogaea, Asparagus officinalis, Avena sativa, Beta vulgaris* spec. *altissima, Beta vulgaris* spec. *rapa, Brassica napus* var. *napus, Brassica napus* var. *napobrassica, Brassica rapa* var. *silvestris, Brassica oleracea, Brassica nigra, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum, Malus* spec., *Manihot esculenta, Medicago sativa, Musa* spec., *Nicotiana tabacum (N. rustica), Olea europaea, Oryza sativa, Phaseolus lunatus, Phaseolus vulgaris, Picea abies, Pinus* spec., *Pistacia vera, Pisum sativum, Prunus avium, Prunus persica, Pyrus communis, Prunus armeniaca, Prunus cerasus, Prunus dulcis* and *Prunus domestica, Ribes sylvestre, Ricinus communis, Saccharum officinarum, Secale cereale, Sinapis alba, Solanum tuberosum, Sorghum bicolor (s. vulgare), Theobroma cacao, Trifolium pratense, Triticum aestivum, Triticale, Triticum durum, Vicia faba, Vitis vinifera* and *Zea mays.*

Preferred crops are the following: *Arachis hypogaea, Beta vulgaris* spec. *altissima, Brassica napus* var. *napus, Brassica oleracea, Citrus limon, Citrus sinensis, Coffea arabica (Coffea canephora, Coffea liberica), Cynodon dactylon, Glycine max, Gossypium hirsutum, (Gossypium arboreum, Gossypium herbaceum, Gossypium vitifolium), Helianthus annuus, Hordeum vulgare, Juglans regia, Lens culinaris, Linum usitatissimum, Lycopersicon lycopersicum, Malus* spec., *Medicago sativa, Nicotiana tabacum (N. rustica), Olea*

*europaea, Oryza sativa, Phaseolus lunatus, Phaseolus vulgaris, Pistacia vera, Pisum sativum, Prunus dulcis, Saccharum officinarum, Secale cereale, Solanum tuberosum, Sorghum bicolor (s. vulgare), Triticale, Triticum aestivum, Triticum durum, Vicia faba, Vitis vinifera* and *Zea mays*.

The benzoxazinones of formula I according to the invention can also be used in genetically modified plants. The term "genetically modified plants" is to be understood as plants, which genetic material has been modified by the use of recombinant DNA techniques in a way that under natural circumstances it cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-translational modification of protein(s), oligo- or polypeptides e.g. by glycosylation or polymer additions such as prenylated, acetylated or farnesylated moieties or PEG moieties. Plants that have been modified by breeding, mutagenesis or genetic engineering, e.g. have been rendered tolerant to applications of specific classes of herbicides, such as hydroxyphenylpyruvate dioxygenase (HPPD) inhibitors; acetolactate synthase (ALS) inhibitors, such as sulfonyl ureas (see e.g. U.S. Pat. No. 6,222,100, WO 01/82685, WO 00/26390, WO 97/41218, WO 98/02526, WO 98/02527, WO 04/106529, WO 05/20673, WO 03/14357, WO 03/13225, WO 03/14356, WO 04/16073) or imidazolinones (see e.g. U.S. Pat. No. 6,222,100, WO 01/82685, WO 00/026390, WO 97/41218, WO 98/002526, WO 98/02527, WO 04/106529, WO 05/20673, WO 03/014357, WO 03/13225, WO 03/14356, WO 04/16073); enolpyruvylshikimate-3-phosphate synthase (EPSPS) inhibitors, such as glyphosate (see e.g. WO 92/00377); glutamine synthetase (GS) inhibitors, such as glufosinate (see e.g. EP-A 242 236, EP-A 242 246) or oxynil herbicides (see e.g. U.S. Pat. No. 5,559, 024) as a result of conventional methods of breeding or genetic engineering. Several cultivated plants have been rendered tolerant to herbicides by conventional methods of breeding (mutagenesis), e.g. Clearfield® summer rape (Canola, BASF SE, Germany) being tolerant to imidazolinones, e.g. imazamox. Genetic engineering methods have been used to render cultivated plants such as soybean, cotton, corn, beets and rape, tolerant to herbicides such as glyphosate and glufosinate, some of which are commercially available under the trade names Round-upReady® (glyphosate-tolerant, Monsanto, U.S.A.) and LibertyLink® (glufosinate-tolerant, Bayer CropScience, Germany).

Furthermore, plants are also covered that are by the use of recombinant DNA techniques capable to synthesize one or more insecticidal proteins, especially those known from the bacterial genus *Bacillus*, particularly from *Bacillus thuringiensis*, such as ä-endotoxins, e.g. CryIA(b), CryIA(c), CryIF, CryIF(a2), CryIIA(b), CryIIIA, CryIIIB(b1) or Cry9c; vegetative insecticidal proteins (VIP), e.g. VIP1, VIP2, VIP3 or VIP3A; insecticidal proteins of bacteria colonizing nematodes, e.g. *Photo-rhab-dus* spp. or *Xenorhabdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilbene synthase, bibenzyl synthase, chitinases or glucanases. In the context of the present invention these insecticidal proteins or toxins are to be under-stood expressly also as pre-toxins, hybrid proteins, truncated or otherwise modified proteins. Hybrid proteins are characterized by a new combination of protein domains, (see, e.g. WO 02/015701). Further examples of such toxins or genetically modified plants capable of synthesizing such toxins are disclosed, e.g., in EP-A 374 753, WO 93/007278, WO 95/34656, EP-A 427 529, EP-A 451 878, WO 03/18810 and WO 03/52073. The methods for producing such genetically modified plants are generally known to the person skilled in the art and are described, e.g. in the publications mentioned above. These insecticidal proteins contained in the genetically modified plants impart to the plants producing these proteins tolerance to harmful pests from all taxonomic groups of arthropods, especially to beetles (*Coleoptera*), two-winged insects (*Diptera*), and moths (*Lepidoptera*) and to nematodes (*Nematoda*). Genetically modified plants capable to synthesize one or more insecticidal proteins are, e.g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme Phosphinothricin-N-Acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Bt11 (e.g. Agrisure® CB) and Bt176 from Syngenta Seeds SAS, France, (corn cultivars producing the Cry1Ab toxin and PAT enzyme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the Cry1F toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e.g. EP-A 392 225), plant disease resistance genes (e.g. potato cultivars, which express resistance genes acting against *Phytophthora infestans* derived from the Mexican wild potato *Solanum bulbocastanum*) or T4-lysozyme (e.g. potato cultivars capable of synthesizing these proteins with increased resistance against bacteria such as *Erwinia amylvora*). The methods for producing such genetically modified plants are generally known to the person skilled in the art and are described, e.g. in the publications mentioned above.

Furthermore, plants are also covered that are by the use of recombinant DNA techniques capable to synthesize one or more proteins to increase the productivity (e.g. bio mass production, grain yield, starch content, oil content or protein content), tolerance to drought, salinity or other growth-limiting environ-mental factors or tolerance to pests and fungal, bacterial or viral pathogens of those plants.

Furthermore, plants are also covered that contain by the use of recombinant DNA techniques a modified amount of substances of content or new substances of content, specifically to improve human or animal nutrition, e.g. oil crops that produce health-promoting long-chain omega-3 fatty acids or unsaturated omega-9 fatty acids (e.g. Nexera® rape, DOW Agro Sciences, Canada).

Furthermore, plants are also covered that contain by the use of recombinant DNA techniques a modified amount of substances of content or new substances of content, specifically to improve raw material production, e.g. potatoes that produce increased amounts of amylopectin (e.g. Amflora® potato, BASF SE, Germany).

The benzoxazinones of formula I according to the invention can also be used in crop plants which are resistant to one or more herbicides owing to genetic engineering or breeding, which are resistant to one or more pathogens such as plant pathogenous fungi owing to genetic engineering or breeding, or which are resistant to attack by insects owing to genetic engineering or breeding.

Suitable are for example crop plants, preferably corn, wheat, sunflower, sugarcane, cotton, rice, canola, oilseed rape or soybeans, which crops are resistant to herbicidal PPO inhibitors, or crop plants which, owing to introduction of the gene for Bt toxin by genetic modification, are resistant to attack by certain insects.

Furthermore, it has been found that the benzoxazinones of the formula I are also suitable for the defoliation and/or desiccation of plant parts, for which crop plants such as cotton, potato, oilseed rape, sunflower, soybean or field beans, in particular cotton, are suitable. In this regard there have been found compositions for the desiccation and/or defoliation of plants, processes for preparing these compositions and methods for desiccating and/or defoliating plants using the benzoxazinones of the formula I. As desiccants, the benzoxazinones of the formula I are particularly suitable for desiccating the above-ground parts of crop plants such as potato, oilseed rape, sunflower and soybean, but also cereals. This makes possible the fully mechanical harvesting of these important crop plants.

Also of economic interest is to facilitate harvesting, which is made possible by concentrating within a certain period of time the dehiscence, or reduction of adhesion to the tree, in citrus fruit, olives and other species and varieties of pernicious fruit, stone fruit and nuts. The same mechanism, i.e. the promotion of the development of abscission tissue between fruit part or leaf part and shoot part of the plants is also essential for the controlled defoliation of useful plants, in particular cotton.

Moreover, a shortening of the time interval in which the individual cotton plants mature leads to an increased fiber quality after harvesting.

The benzoxazinones of formula I, or the herbicidal compositions comprising the benzoxazinones of formula I, can be used, for example, in the form of ready-to-spray aqueous solutions, powders, suspensions, also highly concentrated aqueous, oily or other suspensions or dispersions, emulsions, oil dispersions, pastes, dusts, materials for broadcasting, or granules, by means of spraying, atomizing, dusting, spreading, watering or treatment of the seed or mixing with the seed. The use forms depend on the intended purpose; in any case, they should ensure the finest possible distribution of the active ingredients according to the invention.

The herbicidal compositions comprise an herbicidal effective amount of at least one benzoxazinones of the formula I and auxiliaries which are customary for the formulation of crop protection agents.

Examples of auxiliaries customary for the formulation of crop protection agents are inert auxiliaries, solid carriers, surfactants (such as dispersants, protective colloids, emulsifiers, wetting agents and tackifiers), organic and inorganic thickeners, bactericides, antifreeze agents, antifoams, optionally colorants and, for seed formulations, adhesives.

The person skilled in the art is sufficiently familiar with the recipes for such formulations.

Examples of thickeners (i.e. compounds which impart to the formulation modified flow properties, i.e. high viscosity in the state of rest and low viscosity in motion) are polysaccharides, such as xanthan gum (Kelzan® from Kelco), Rhodopol® 23 (Rhone Poulenc) or Veegum® (from R.T. Vanderbilt), and also organic and inorganic sheet minerals, such as Attaclay® (from Engelhard).

Examples of antifoams are silicone emulsions (such as, for example, Silikon® SRE, Wacker or Rhodorsil® from Rhodia), long-chain alcohols, fatty acids, salts of fatty acids, organofluorine compounds and mixtures thereof.

Bactericides can be added for stabilizing the aqueous herbicidal formulations. Examples of bactericides are bactericides based on dichlorophen and benzyl alcohol hemiformal (Proxel® from ICI or Acticide® RS from Thori Chemie and Kathon® MK from Rohm & Haas), and also isothiazolinone derivates, such as alkylisothiazolinones and benzisothiazolinones (Acticide MBS from Thor Chemie).

Examples of antifreeze agents are ethylene glycol, propylene glycol, urea or glycerol.

Examples of colorants are both sparingly water-soluble pigments and water-soluble dyes. Examples which may be mentioned are the dyes known under the names Rhodamin B, C.I. Pigment Red 112 and C.I. Solvent Red 1, and also pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108.

Examples of adhesives are polyvinylpyrrolidone, polyvinyl acetate, polyvinyl alcohol and tylose.

Suitable inert auxiliaries are, for example, the following: mineral oil fractions of medium to high boiling point, such as kerosene and diesel oil, furthermore coal tar oils and oils of vegetable or animal origin, aliphatic, cyclic and aromatic hydrocarbons, for example paraffin, tetrahydronaphthalene, alkylated naphthalenes and their derivatives, alkylated benzenes and their derivatives, alcohols such as methanol, ethanol, propanol, butanol and cyclohexanol, ketones such as cyclohexanone or strongly polar solvents, for example amines such as N-methylpyrrolidone, and water.

Suitable carriers include liquid and solid carriers. Liquid carriers include e.g. non-aqueous solvents such as cyclic and aromatic hydrocarbons, e.g. paraffins, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, e.g. amines such as N-methylpyrrolidone, and water as well as mixtures thereof.

Solid carriers include e.g. mineral earths such as silicas, silica gels, silicates, talc, kaolin, limestone, lime, chalk, bole, loess, clay, dolomite, diatomaceous earth, calcium sulfate, magnesium sulfate and magnesium oxide, ground synthetic materials, fertilizers such as ammonium sulfate, ammonium phosphate, ammonium nitrate and ureas, and products of vegetable origin, such as cereal meal, tree bark meal, wood meal and nutshell meal, cellulose powders, or other solid carriers.

Suitable surfactants (adjuvants, wetting agents, tackifiers, dispersants and also emulsifiers) are the alkali metal salts, alkaline earth metal salts and ammonium salts of aromatic sulfonic acids, for example lignosulfonic acids (e.g. Borrespers-types, Borregaard), phenolsulfonic acids, naphthalenesulfonic acids (Morwet types, Akzo Nobel) and dibutylnaphthalenesulfonic acid (Nekal types, BASF SE), and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenyl or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors and proteins, denaturated proteins, polysaccharides (e.g. methylcellulose), hydrophobically modified starches, polyvinyl alcohol (Mowiol types Clariant), polycarboxylates (BASF SE, Sokalan types), polyalkoxylates, polyvinylamine (BASF SE, Lupamine types), polyethyleneimine (BASF SE, Lupasol types), polyvinylpyrrolidone and copolymers thereof.

Powders, materials for broadcasting and dusts can be prepared by mixing or concomitant grinding the active ingredients together with a solid carrier. Granules, for example coated granules, impregnated granules and homogeneous granules, can be prepared by binding the active ingredients to solid carriers.

Aqueous use forms can be prepared from emulsion concentrates, suspensions, pastes, wettable powders or water-dispersible granules by adding water.

To prepare emulsions, pastes or oil dispersions, the benzoxazinones of the formula I, either as such or dissolved in an oil or solvent, can be homogenized in water by means of a wetting agent, tackifier, dispersant or emulsifier. Alternatively, it is also possible to prepare concentrates comprising active compound, wetting agent, tackifier, dispersant or emulsifier and, if desired, solvent or oil, which are suitable for dilution with water.

The concentrations of the benzoxazinones of the formula I in the ready-to-use preparations (formulations) can be varied within wide ranges. In general, the formulations comprise approximately from 0.001 to 98% by weight, preferably 0.01 to 95% by weight of at least one active ingredient. The active ingredients are employed in a purity of from 90% to 100%, preferably 95% to 100% (according to NMR spectrum).

In the formulation of the benzoxazinones of formula I according to the present invention the active ingredients, e.g. the benzoxazinones of formula I, are present in suspended, emulsified or dissolved form. The formulation according to the invention can be in the form of aqueous solutions, powders, suspensions, also highly-concentrated aqueous, oily or other suspensions or dispersions, aqueous emulsions, aqueous microemulsions, aqueous suspo-emulsions, oil dispersions, pastes, dusts, materials for spreading or granules.

The benzoxazinones of formula I according to the present invention can, for example, be formulated as follows:

1. Products for Dilution with Water

A Water-Soluble Concentrates 10 parts by weight of active compound are dissolved in 90 parts by weight of water or a water-soluble solvent. As an alternative, wetters or other adjuvants are added. The active compound dissolves upon dilution with water. This gives a formulation with an active compound content of 10% by weight.

B Dispersible Concentrates 20 parts by weight of active compound are dissolved in 70 parts by weight of cyclohexanone with addition of 10 parts by weight of a dispersant, for example polyvinylpyrrolidone. Dilution with water gives a dispersion. The active compound content is 20% by weight.

C Emulsifiable Concentrates 15 parts by weight of active compound are dissolved in 75 parts by weight of an organic solvent (e.g. alkylaromatics) with addition of calcium dodecylbenzenesulfonate and castor oil ethoxylate (in each case 5 parts by weight). Dilution with water gives an emulsion. The formulation has an active compound content of 15% by weight.

D Emulsions 25 parts by weight of active compound are dissolved in 35 parts by weight of an organic solvent (e.g. alkylaromatics) with addition of calcium dodecylbenzenesulfonate and castor oil ethoxylate (in each case 5 parts by weight). This mixture is introduced into 30 parts by weight of water by means of an emulsifier (Ultraturrax) and made into a homogeneous emulsion. Dilution with water gives an emulsion. The formulation has an active compound content of 25% by weight.

E Suspensions

In an agitated ball mill, 20 parts by weight of active compound are comminuted with addition of 10 parts by weight of dispersants and wetters and 70 parts by weight of water or an organic solvent to give a fine active compound suspension. Dilution with water gives a stable suspension of the active compound. The active compound content in the formulation is 20% by weight.

F Water-Dispersible Granules and Water-Soluble Granules 50 parts by weight of active compound are ground finely with addition of 50 parts by weight of dispersants and wetters and made into water-dispersible or water-soluble granules by means of technical appliances (for example extrusion, spray tower, fluidized bed). Dilution with water gives a stable dispersion or solution of the active compound. The formulation has an active compound content of 50% by weight.

G Water-Dispersible Powders and Water-Soluble Powders 75 parts by weight of active compound are ground in a rotor-stator mill with addition of 25 parts by weight of dispersants, wetters and silica gel. Dilution with water gives a stable dispersion or solution of the active compound. The active compound content of the formulation is 75% by weight.

H Gel Formulations

In a ball mill, 20 parts by weight of active compound, 10 parts by weight of dispersant, 1 part by weight of gelling agent and 70 parts by weight of water or of an organic solvent are mixed to give a fine suspension. Dilution with water gives a stable suspension with active compound content of 20% by weight.

2. Products to be Applied Undiluted

I Dusts 5 parts by weight of active compound are ground finely and mixed intimately with 95 parts by weight of finely divided kaolin. This gives a dusting powder with an active compound content of 5% by weight.

J Granules (GR, FG, GG, MG)

0.5 parts by weight of active compound are ground finely and associated with 99.5 parts by weight of carriers. Current methods here are extrusion, spray-drying or the fluidized bed. This gives granules to be applied undiluted with an active compound content of 0.5% by weight.

K ULV Solutions (UL)

10 parts by weight of active compound are dissolved in 90 parts by weight of an organic solvent, for example xylene. This gives a product to be applied undiluted with an active compound content of 10% by weight.

Aqueous use forms can be prepared from emulsion concentrates, suspensions, pastes, wettable powders or water-dispersible granules by adding water.

The benzoxazinones of the formula I or the herbicidal compositions comprising them can be applied pre-, post-emergence or pre-plant, or together with the seed of a crop plant. It is also possible to apply the herbicidal composition or active compounds by applying seed, pretreated with the herbicidal compositions or active compounds, of a crop plant. If the active ingredients are less well tolerated by certain crop plants, application techniques may be used in which the herbicidal compositions are sprayed, with the aid of the spraying equipment, in such a way that as far as possible they do not come into contact with the leaves of the sensitive crop plants, while the active ingredients reach the leaves of undesirable plants growing underneath, or the bare soil surface (post-directed, lay-by).

In a further embodiment, the benzoxazinones of the formula I or the herbicidal compositions can be applied by treating seed. The treatment of seeds comprises essentially all procedures familiar to the person skilled in the art (seed dressing, seed coating, seed dusting, seed soaking, seed film coating, seed multilayer coating, seed encrusting, seed dripping and seed pelleting) based on the benzoxazinones of the formula I according to the invention or the compositions prepared therefrom. Here, the herbicidal compositions can be applied diluted or undiluted.

The term "seed" comprises seed of all types, such as, for example, corns, seeds, fruits, tubers, seedlings and similar forms. Here, preferably, the term seed describes corns and seeds. The seed used can be seed of the useful plants mentioned above, but also the seed of transgenic plants or plants obtained by customary breeding methods.

The rates of application of the active benzoxazinones of formula I according to the present invention (total amount of benzoxazinone I) are from 0.1 g/ha to 3000 g/ha, preferably 10 g/ha to 1000 g/ha of active substance (a.s.), depending on the control target, the season, the target plants and the growth stage.

In another preferred embodiment of the invention, the application rates of the benzoxazinones of formula I are in the range from 0.1 g/ha to 5000 g/ha and preferably in the range from 1 g/ha to 2500 g/ha or from 5 g/ha to 2000 g/ha of active substance (a.s.).

In another preferred embodiment of the invention, the application rate of the benzoxazinones of formula I is 0.1 to 1000 g/ha, preferably) to 750 g/ha, more preferably 5 to 500 g/ha, of active substance.

To treat the seed, the benzoxazinones of formula I are generally employed in amounts of from 0.001 to 10 kg per 100 kg of seed.

To broaden the spectrum of action and to achieve synergistic effects, the benzoxazinones of the formula I may be mixed with a large number of representatives of other herbicidal or growth-regulating active ingredient groups and then applied concomitantly. Suitable components for mixtures are, for example, 1,2,4-thiadiazoles, 1,3,4-thiadiazoles, amides, aminophosphoric acid and its derivatives, aminotriazoles, anilides, (het)aryloxyalkanoic acids and their derivatives, benzoic acid and its derivatives, benzothiadiazinones, 2-aroyl-1,3-cyclohexanediones, 2-hetaroyl-1,3-cyclohexanediones, hetaryl aryl ketones, benzylisoxazolidinones, meta-$CF_3$-phenyl derivatives, carbamates, quinolinecarboxylic acid and its derivatives, chloroacetanilides, cyclohexenone oxime ether derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyl-uracils, imidazoles, imidazolinones, N-phenyl-3,4,5,6-uracils, oxadiazoles, oxiranes, phenols, aryloxy- and hetaryloxyphenoxypropionic esters, phenylacetic acid and its derivatives, 2-phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides, uracils, phenyl pyrazolines and isoxazolines and derivatives thereof.

It may be beneficial to apply the benzoxazinones of the formula I alone or in combination with other herbicides, or else in the form of a mixture with other crop protection agents, for example together with agents for controlling pests or phytopathogenic fungi or bacteria.

Also of interest is the miscibility with mineral salt solutions, which are employed for treating nutritional and trace element deficiencies. Other additives such as non-phytotoxic oils and oil concentrates may also be added.

The further herbicidal active component B is preferably selected from the herbicides of class b1) to b15):

b1) lipid biosynthesis inhibitors;
b2) acetolactate synthase inhibitors (ALS inhibitors);
b3) photosynthesis inhibitors;
b4) protoporphyrinogen-IX oxidase inhibitors,
b5) bleacher herbicides;
b6) enolpyruvyl shikimate 3-phosphate synthase inhibitors (EPSP inhibitors);
b7) glutamine synthetase inhibitors;
b8) 7,8-dihydropteroate synthase inhibitors (DHP inhibitors);
b9) mitose inhibitors;
b10) inhibitors of the synthesis of very long chain fatty acids (VLCFA inhibitors);
b11) cellulose biosynthesis inhibitors;
b12) decoupler herbicides;

b13) auxin herbicides;
b14) auxin transport inhibitors; and
b15) other herbicides selected from the group consisting of bromobutide, chlorflurenol, chlorflurenol-methyl, cinmethylin, cumyluron, dalapon, dazomet, difenzoquat, difenzoquat-metilsulfate, dimethipin, DSMA, dymron, endothal and its salts, etobenzanid, flamprop, flamprop-isopropyl, flamprop-methyl, flamprop-M-isopropyl, flamprop-M-methyl, flurenol, flurenol-butyl, flurprimidol, fosamine, fosamine-ammonium, indanofan, indaziflam, maleic hydrazide, mefluidide, metam, methyl azide, methyl bromide, methyl-dymron, methyl iodide, MSMA, oleic acid, oxaziclomefone, pelargonic acid, pyributicarb, quinoclamine, triaziflam, tridiphane and 6-chloro-3-(2-cyclopropyl-6-methylphenoxy)-4-pyridazinol (CAS 499223-49-3) and its salts and esters;

Preference is given to those compositions according to the present invention comprising at least one herbicide B selected from herbicides of class b2, b3, b4, b5, b6, b7, b9, b10 and b13.

Particular preference is given to those compositions according to the present invention which comprise at least one herbicide B selected from the herbicides of class b4, b6 and b10.

Examples of herbicides B which can be used in combination with the benzoxazinones of the formula I according to the present invention are:

b1) from the group of the lipid biosynthesis inhibitors:
ACC-herbicides such as alloxydim, alloxydim-sodium, butroxydim, clethodim, clodinafop, clodinafop-propargyl, cycloxydim, cyhalofop, cyhalofop-butyl, diclofop, diclofop-methyl, fenoxaprop, fenoxaprop-ethyl, fenoxaprop-P, fenoxaprop-P-ethyl, fluazifop, fluazifop-butyl, fluazifop-P, fluazifop-P-butyl, haloxyfop, haloxyfop-methyl, haloxyfop-P, haloxyfop-P-methyl, metamifop, pinoxaden, profoxydim, propaquizafop, quizalofop, quizalofop-ethyl, quizalofop-tefuryl, quizalofop-P, quizalofop-P-ethyl, quizalofop-P-tefuryl, sethoxydim, tepraloxydim and tralkoxydim, and non ACC herbicides such as benfuresate, butylate, cycloate, dalapon, dimepiperate, EPTC, esprocarb, ethofumesate, flupropanate, molinate, orbencarb, pebulate, prosulfocarb, TCA, thiobencarb, tiocarbazil, triallate and vernolate;

b2) from the group of the ALS inhibitors:
Sulfonylureas such as amidosulfuron, azimsulfuron, bensulfuron, bensulfuron-methyl, chlorimuron, chlorimuron-ethyl, chlorsulfuron, cinosulfuron, cyclosulfamuron, ethametsulfuron, ethametsulfuron-methyl, ethoxysulfuron, flazasulfuron, flucetosulfuron, flupyrsulfuron, flupyrsulfuron-methyl-sodium, foramsulfuron, halosulfuron, halosulfuronmethyl, imazosulfuron, iodosulfuron, iodosulfuron-methyl-sodium, mesosulfuron, metazosulfuron, metsulfuron, metsulfuron-methyl, nicosulfuron, orthosulfamuron, oxasulfuron, primisulfuron, primisulfuron-methyl, propyrisulfuron, prosulfuron, pyrazosulfuron, pyrazosulfuron-ethyl, rimsulfuron, sulfometuron, sulfometuron-methyl, sulfosulfuron, thifensulfuron, thifensulfuron-methyl, triasulfuron, tribenuron, tribenuron-methyl, trifloxysulfuron, triflusulfuron, triflusulfuron-methyl and tritosulfuron, imidazolinones such as imazamethabenz, imazamethabenz-methyl, imazamox, imazapic, imazapyr, imazaquin and imazethapyr, triazolopyrimidine herbicides and sulfonanilides such as cloransulam, cloransulam-methyl, diclosulam, flumetsulam, florasulam, metosulam, penoxsulam, pyrimisulfan and pyroxsulam, pyrimidinylbenzoates such as bispyribac, bispyribac-sodium, pyribenzoxim, pyriftalid, pyriminobac, pyriminobac-methyl, pyrithiobac, pyrithiobac-sodium, 4-[[[2-[(4,6-dimethoxy-2-pyrimidinyl)oxy]phenyl]methyl]amino]-benzoic acid-1-methylethyl ester (CAS 420138-41-6), 4-[[[2-[(4,6-dimethoxy-2-pyrimidinyl)oxy]phenyl]methyl]amino]-benzoic acid propyl ester (CAS 420138-40-5), N-(4-bromophenyl)-2-[(4,6-dimethoxy-2-pyrimidinyl)oxy]benzenemethanamine (CAS 420138-01-8) and sulfonylaminocarbonyl-triazolinone herbicides such as flucarbazone, flucarbazone-sodium, propoxycarbazone, propoxycarbazone-sodium, thiencarbazone and thiencarbazone-methyl. Among these, a preferred embodiment of the invention relates to those compositions comprising at least one imidazolinone herbicide;

b3) from the group of the photosynthesis inhibitors:
amicarbazone, inhibitors of the photosystem II, e.g. triazine herbicides, including of chlorotriazine, triazinones, triazindiones, methylthiotriazines and pyridazinones such as ametryn, atrazine, chloridazon, cyanazine, desmetryn, dimethametryn, hexazinone, metribuzin, prometon, prometryn, propazine, simazine, simetryn, terbumeton, terbuthylazin, terbutryn and trietazin, aryl urea such as chlorobromuron, chlorotoluron, chloroxuron, dimefuron, diuron, fluometuron, isoproturon, isouron, linuron, metamitron, methabenzthiazuron, metobenzuron, metoxuron, monolinuron, neburon, siduron, tebuthiuron and thiadiazuron, phenyl carbamates such as desmedipham, karbutilat, phenmedipham, phenmedipham-ethyl, nitrile herbicides such as bromofenoxim, bromoxynil and its salts and esters, ioxynil and its salts and esters, uraciles such as bromacil, lenacil and terbacil, and bentazon and bentazon-sodium, pyridate, pyridafol, pentanochlor and propanil and inhibitors of the photosystem I such as diquat, diquat-dibromide, paraquat, paraquat-dichloride and paraquat-dimetilsulfate. Among these, a preferred embodiment of the invention relates to those compositions comprising at least one aryl urea herbicide. Among these, likewise a preferred embodiment of the invention relates to those compositions comprising at least one triazine herbicide. Among these, likewise a preferred embodiment of the invention relates to those compositions comprising at least one nitrile herbicide;

b4) from the group of the protoporphyrinogen-IX oxidase inhibitors:
acifluorfen, acifluorfen-sodium, azafenidin, bencarbazone, benzfendizone, bifenox, butafenacil, carfentrazone, carfentrazone-ethyl, chlomethoxyfen, cinidon-ethyl, fluazolate, flufenpyr, flufenpyr-ethyl, flumiclorac, flumiclorac-pentyl, flumioxazin, fluoroglycofen, fluoroglycofen-ethyl, fluthiacet, fluthiacet-methyl, fomesafen, halosafen, lactofen, oxadiargyl, oxadiazon, oxyfluorfen, pentoxazone, profluazol, pyraclonil, pyraflufen, pyraflufen-ethyl, saflufenacil, sulfentrazone, thidiazimin, ethyl[3-[2-chloro-4-fluoro-5-(1-methyl-6-trifluoromethyl-2,4-dioxo-1,2,3,4-tetrahydropyrimidin-3-yl)phenoxy]-2-pyridyloxy]acetate (CAS 353292-31-6; S-3100), N-ethyl-3-(2,6-dichloro-4-trifluoromethylphenoxy)-5-methyl-1H-pyrazole-1-carboxamide (CAS 452098-92-9), N-tetrahydrofurfuryl-3-(2,6-dichloro-4-trifluoromethylphenoxy)-5-methyl-1H-pyrazole-1-carboxamide (CAS 915396-43-9), N-ethyl-3-(2-chloro-6-fluoro-4-trifluoromethylphenoxy)-5-methyl-1H-pyrazole-1-carboxamide (CAS 452099-05-7), N-tetrahydrofurfuryl-3-(2-chloro-6-fluoro-4-trifluoromethylphenoxy)-5-methyl-1H-pyrazole-1-carboxamide (CAS 45100-03-7), 3-[7-fluoro-3-oxo-4-(prop-2-ynyl)-3,4-dihydro-2H-benzo[1,4]oxazin-6-yl]-1,5-dimethyl-6-thioxo-[1,3,5]triazinan-2,4-dione, 1,5-dimethyl-6-thioxo-3-(2,2,7-trifluoro-3-oxo-4-(prop-2-ynyl)-3,4-dihydro-2H-benzo[b][1,4]oxazin-6-yl)-1,3,5-triazinane-2,4-dione, 2-(2,2,7-Trifluoro-3-oxo-4-prop-2-ynyl-3,4-dihydro-2H-benzo[1,4]oxazin-6-yl)-4,5,6,7-tetrahydro-isoindole-1,3-dione, and 1-Methyl-6- trifluoromethyl-3-(2,2,7-trifluoro-3-oxo-4-prop-2-ynyl-3,4-dihydro-2H-benzo[1,4]oxazin-6-yl)-1H-pyrimidine-2,4-dione;
b5) from the group of the bleacher herbicides:
PDS inhibitors: beflubutamid, diflufenican, fluridone, fluorochloridone, flurtamone, norflurazon, picolinafen, and 4-(3-trifluoromethylphenoxy)-2-(4-trifluoromethylphenyl)pyrimidine (CAS 180608-33-7), HPPD inhibitors: benzobicyclon, benzofenap, clomazone, isoxaflutole, mesotrione, pyrasulfotole, pyrazolynate, pyrazoxyfen, sulcotrione, tefuryltrione, tembotrione, topramezone and bicyclopyrone, bleacher, unknown target: aclonifen, amitrole and flumeturon;
b6) from the group of the EPSP synthase inhibitors:
glyphosate, glyphosate-isopropylammonium, glyposate-potassium and glyphosate-trimesium (sulfosate);
b7) from the group of the glutamine synthase inhibitors:
bilanaphos (bialaphos), bilanaphos-sodium, glufosinate, glufosinate-P and glufosinate-ammonium;
b8) from the group of the DHP synthase inhibitors:
asulam;
b9) from the group of the mitosis inhibitors:
compounds of group K1: dinitroanilines such as benfluralin, butralin, dinitramine, ethalfluralin, fluchloralin, oryzalin, pendimethalin, prodiamine and trifluralin, phosphoramidates such as amiprophos, amiprophos-methyl, and butamiphos, benzoic acid herbicides such as chlorthal, chlorthal-dimethyl, pyridines such as dithiopyr and thiazopyr, benzamides such as propyzamide and tebutam; compounds of group K2: chlorpropham, propham and carbetamide, among these, compounds of group K1, in particular dinitroanilines are preferred;
b10) from the group of the VLCFA inhibitors:
chloroacetamides such as acetochlor, alachlor, butachlor, dimethachlor, dimethenamid, dimethenamid-P, metazachlor, metolachlor, metolachlor-S, pethoxamid, pretilachlor, propachlor, propisochlor and thenylchlor, oxyacetanilides such as flufenacet and mefenacet, acetanilides such as diphenamid, naproanilide and napropamide, tetrazolinones such fentrazamide, and other herbicides such as anilofos, cafenstrole, fenoxasulfone, ipfencarbazone, piperophos, pyroxasulfone and isoxazoline compounds of the formula II#,

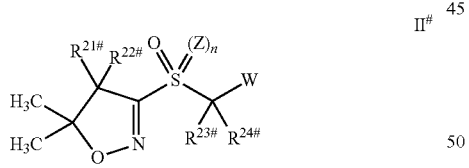

wherein $R^{21\#}$, $R^{22\#}$, $R^{23\#}$, $R^{24\#}$, W, Z and n have the following meanings:
$R^{21\#}$, $R^{22\#}$, $R^{23\#}$, $R^{24\#}$ independently of one another hydrogen, halogen or $C_1$-$C_4$-alkyl;
W phenyl or monocyclic 5-, 6-, 7-, 8-, 9- or 10-membered heterocyclyl containing, in addition to carbon ring members one, two or three same or different heteroatoms selected from oxygen, nitrogen and sulfur as ring members, wherein phenyl and heterocyclyl are unsubstituted or carry 1, 2 or 3 substituents $R^{yy}$ selected from halogen, $C_1$-$C_4$-alkyl, $C_1$-$C_4$-alkoxy, $C_1$-$C_4$-haloalkyl and $C_1$-$C_4$-haloalkoxy;
preferably phenyl or 5- or 6-membered aromatic heterocyclyl (hetaryl) which contains, in addition to carbon ring members, one, two or three nitrogen atoms as ring members, wherein phenyl and hetaryl are unsubstituted or carry 1, 2 or 3 substituents $R^{yy}$;
Z oxygen or NH; and
n zero or one;
among the isoxazoline compounds of the formula II#, preference is given to isoxazoline compounds of the formula II#, wherein
$R^{21\#}$, $R^{22\#}$, $R^{23\#}$, $R^{24\#}$ independently of one another are H, F, Cl or methyl;
Z is oxygen;
n is 0 or 1; and
W is phenyl, pyrazolyl or 1,2,3-triazolyl, wherein the three last-mentioned radicals are unsubstituted or carry one, two or three substituents $R^{yy}$, especially one of the following radicals

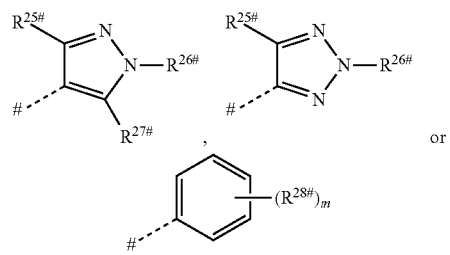

wherein
$R^{25\#}$ is halogen, $C_1$-$C_4$-alkyl or $C_1$-$C_4$-haloalkyl;
$R^{26\#}$ is $C_1$-$C_4$-alkyl;
$R^{27\#}$ is halogen, $C_1$-$C_4$-alkoxy or $C_1$-$C_4$-haloalkoxy;
$R^{28\#}$ is halogen, $C_1$-$C_4$-alkyl, $C_1$-$C_4$-haloalkyl or $C_1$-$C_4$-haloalkoxy;
m is 0, 1, 2 or 3; and
# denotes the point of attachment to the group $CR^{23\#}R^{24\#}$;
among the isoxazoline compounds of the formula II#, particular preference is given to those isoxazoline compounds of the formula II#, wherein
$R^{21\#}$ is hydrogen;
$R^{22\#}$ is fluorine;
$R^{23\#}$ is hydrogen or fluorine;
$R^{24\#}$ is hydrogen or fluorine;
W is one of the radicals of the formulae $W^1$, $W^2$, $W^3$ or $W^4$

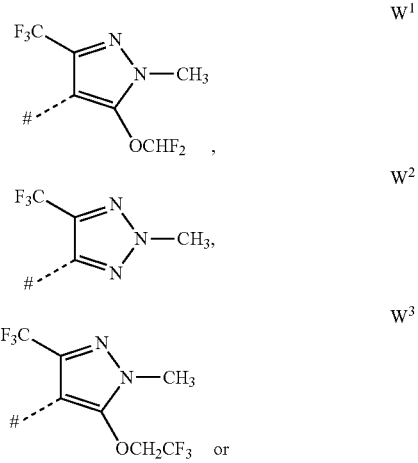

-continued

W⁴ (2,6-difluorophenyl structure)

wherein # denotes the point of attachment to the group $CR^{23\#}R^{24\#}$;
Z is oxygen;
n is zero or 1, in particular 1; and
among these, especially preferred are the isoxazoline compounds of the formulae II#0.1, II⁴⁰0.2, II⁴⁰0.3, II⁴⁰0.4, II⁴⁰0.5, II⁴⁰0.6, II⁴⁰0.7, II⁴⁰0.8 and II⁴⁰0.9

II#.1
II#.2
II#.3
II#.4
II#.5
II#.6
II#.7
II#.8
II#.9 the isoxazoline compounds of the formula II# are known in the art, e.g. from WO 2006/024820, WO 2006/037945, WO 2007/071900 and WO 2007/096576;
among the VLCFA inhibitors, preference is given to chloroacetamides and oxyacetamides;
b11) from the group of the cellulose biosynthesis inhibitors: chlorthiamid, dichlobenil, flupoxam, isoxaben, 1-Cyclohexyl-5-pentafluorphenyloxy-1⁴-[1,2,4,6]thiatriazin-3-ylamine and piperazine compounds of formula III,

III# in which
A is phenyl or pyridyl where $R^{a\#}$ is attached in the ortho-position to the point of attachment of A to a carbon atom;
$R^{a\#}$ is CN, NO$_2$, C$_1$-C$_4$-alkyl, D-C$_3$-C$_6$-cycloalkyl, C$_1$-C$_4$-haloalkyl, C$_1$-C$_4$-alkoxy, C$_1$-C$_4$-haloalkoxy, O-D-C$_3$-C$_6$-cycloalkyl, S(O)$_q$R$^y$, C$_2$-C$_6$-alkenyl, D-C$_3$-C$_6$-cycloalkenyl, C$_3$-C$_6$-alkenyloxy, C$_2$-C$_6$-alkynyl, C$_3$-C$_6$-alkynyloxy, NR$^A$R$^B$, tri-C$_1$-C$_4$-alkylsilyl, D-C(=O)—R$^{a1}$, D-P(=O)(R$^{a1}$)$_2$, phenyl, naphthyl, a 3- to 7-membered monocyclic or 9- or 10-membered bicyclic saturated, unsaturated or aromatic heterocycle which is attached via carbon or nitrogen, which contains 1, 2, 3 or 4 heteroatoms selected from the group consisting of O, N and S, and which may be partially or fully substituted by groups R$^{aa}$ and/or R$^{a1}$, and, if R$^a$ is attached to a carbon atom, additionally halogen;
R$^y$ is C$_1$-C$_6$-alkyl, C$_3$-C$_4$-alkenyl, C$_3$-C$_4$-alkynyl, NR$^A$R$^B$ or C$_1$-C$_4$-haloalkyl and q is 0, 1 or 2;
R$^A$,R$^B$ independently of one another are hydrogen, C$_1$-C$_6$-alkyl, C$_3$-C$_6$-alkenyl and C$_3$-C$_6$-alkynyl; together with the nitrogen atom to which they are attached, R$^A$,R$^B$ may also form a five- or six-membered saturated, partially or fully unsaturated ring which, in addition to carbon atoms, may contain 1, 2 or 3 heteroatoms selected from the group consisting of O, N and S, which ring may be substituted by 1 to 3 groups $R^{aa}$;

D is a covalent bond, $C_1$-$C_4$-alkylene, $C_2$-$C_6$-alkenyl or $C_2$-$C_6$-alkynyl;

$R^{a1}$ is hydrogen, OH, $C_1$-$C_8$-Alkyl, $C_1$-$C_4$-haloalkyl, $C_3$-$C_6$-cycloalkyl, $C_2$-$C_8$-alkenyl, $C_5$-$C_6$-cycloalkenyl, $C_2$-$C_8$-alkynyl, $C_1$-$C_6$-alkoxy, $C_1$-$C_4$-haloalkoxy, $C_3$-$C_8$-alkenyloxy, $C_3$-$C_8$-alkynyloxy, $NR^A R^B$, $C_1$-$C_6$-alkoxyamino, $C_1$-$C_6$-alkylsulfonylamino, $C_1$-$C_6$-alkylaminosulfonylamino, [di-($C_1$-$C_6$)alkylamino]sulfonylamino, $C_3$-$C_6$-alkenylamino, $C_3$-$C_6$-alkynylamino, N—($C_2$-$C_6$-alkenyl)-N—($C_1$-$C_6$-alkyl)amino, N—($C_2$-$C_6$-alkynyl)-N—($C_1$-$C_6$-alkyl)amino, N—($C_1$-$C_6$-alkoxy)-N—($C_1$-$C_6$-alkyl) amino, N—($C_2$-$C_6$-alkenyl)-N—($C_1$-$C_6$-alkoxy) amino, N—($C_2$-$C_6$-alkynyl)-N—($C_1$-$C_6$-alkoxy)-amino, $C_1$-$C_6$-alkylsulfonyl, tri-$C_1$-$C_4$-alkylsilyl; phenyl, phenoxy, phenylamino or a 5- or 6-membered monocyclic or 9- or 10-membered bicyclic heterocycle which contains 1, 2, 3 or 4 heteroatoms selected from the group consisting of O, N and S, where the cyclic groups are unsubstituted or substituted by 1, 2, 3 or 4 groups $R^{aa}$;

$R^{aa}$ is halogen, OH, CN, $NO_2$, $C_1$-$C_4$-alkyl, $C_1$-$C_4$-haloalkyl, $C_1$-$C_4$-alkoxy, $C_1$-$C_4$-haloalkoxy, $S(O)_q R^y$, D-C(=O)—$R^{a1}$ and tri-$C_1$-$C_4$-alkylsilyl;

$R^{b\#}$ independently of one another are hydrogen, CN, $NO_2$, halogen, $C_1$-$C_4$-alkyl, $C_1$-$C_4$-haloalkyl, $C_2$-$C_4$-alkenyl, $C_3$-$C_6$-alkynyl, $C_1$-$C_4$-alkoxy, $C_1$-$C_4$-haloalkoxy, benzyl or $S(O)_q R^y$, $R^b$ together with the group $R^a$ or $R^b$ attached to the adjacent ring atom may also form a five- or six-membered saturated or partially or fully unsaturated ring which, in addition to carbon atoms, may contain 1, 2 or 3 heteroatoms selected from the group consisting of O, N and S, which ring may be partially or fully substituted by $R^{aa}$;

p is 0, 1, 2 or 3;

$R^{30\#}$ is hydrogen, OH, CN, $C_1$-$C_{12}$-alkyl, $C_3$-$C_{12}$-alkenyl, $C_3$-$C_{12}$-alkynyl, $C_1$-$C_4$-alkoxy, $C_3$-$C_6$-cycloalkyl, $C_5$-$C_6$-cycloalkenyl, $NR^A R^B$, $S(O)_n R^y$, $S(O)_n NR^A R^B$, $C(=O)R^{40\#}$, $CONR^A R^B$, phenyl or a 5- or 6-membered monocyclic or 9- or 10-membered bicyclic aromatic heterocycle which contains 1, 2, 3 or 4 heteroatoms selected from the group consisting of O, N and S, where the cyclic groups are attached via $D^1$ and are unsubstituted or substituted by 1, 2, 3 or 4 groups $R^{aa}$, and also the following partially or fully $R^{aa}$-substituted groups: $C_1$-$C_4$-alkyl, $C_3$-$C_4$-alkenyl, $C_3$-$C_4$-alkynyl, $C_1$-$C_4$-alkoxy, $C_3$-$C_6$-cycloalkyl, $C_5$-$C_6$-cycloalkenyl, $NR^A R^B$, $S(O)_n R_y$, $S(O)_n NR^A R^B$, $C(=O)R^{40}$ and $CONR^A R^B$;

$R^{40\#}$ is hydrogen, $C_1$-$C_4$-alkyl, $C_1$-$C_4$-haloalkyl, $C_1$-$C_4$-alkoxy or $C_1$-$C_4$-haloalkoxy;

$D^1$ is carbonyl or a group D;

where in groups $R^{15}$, $R^a$ and their sub-substituents the carbon chains and/or the cyclic groups may carry 1, 2, 3 or 4 substituents $R^{aa}$ and/or $R^{a1}$;

$R^{31\#}$ is $C_1$-$C_4$-alkyl, $C_3$-$C_4$-alkenyl or $C_3$-$C_4$-alkynyl;

$R^{32\#}$ is OH, $NH_2$, $C_1$-$C_4$-alkyl, $C_3$-$C_6$-cycloalkyl, $C_3$-$C_6$-alkenyl, $C_3$-$C_6$-alkynyl, $C_1$-$C_4$-hydroxyalkyl, $C_1$-$C_4$-cyanoalkyl, $C_1$-$C_4$-haloalkyl, $C_1$-$C_4$-alkoxy-$C_1$-$C_4$-alkyl or $C(=O)R^{40}$;

$R^{33\#}$ is hydrogen, halogen, $C_1$-$C_4$-alkyl or $C_1$-$C_4$-haloalkyl, or $R^{33\#}$ and $R^{34\#}$ together are a covalent bond;

$R^{34\#}$, $R^{35\#}$, $R^{36\#}$, $R^{37\#}$ independently of one another are hydrogen, halogen, OH, CN, $NO_2$, $C_1$-$C_4$-alkyl, $C_1$-$C_4$-haloalkyl, $C_2$-$C_6$-alkenyl, $C_2$-$C_6$-alkynyl, $C_1$-$C_4$-alkoxy, $C_1$-$C_4$-haloalkoxy, $C_3$-$C_6$-cycloalkyl, $C_3$-$C_6$-cycloalkenyl and $C_3$-$C_6$-cycloalkynyl;

$R^{38\#}$, $R^{39\#}$ independently of one another are hydrogen, halogen, OH, haloalkyl, $NR^A R^B$, $NR^A C(O)R^{41}$, CN, $NO_2$, $C_1$-$C_4$-alkyl, $C_1$-$C_4$-haloalkyl, $C_2$-$C_4$-alkenyl, $C_3$-$C_6$-alkynyl, $C_1$-$C_4$-alkoxy, $C_1$-$C_4$-haloalkoxy, O—C(O)$R^{41}$, phenoxy or benzyloxy, where in groups $R^{38\#}$ and $R^{39\#}$ the carbon chains and/or the cyclic groups may carry 1, 2, 3 or 4 substituents $R^{aa}$;

$R^{41\#}$ is $C_1$-$C_4$-alkyl or $NR^A R^B$;

among the piperazine compounds of formula III$^\#$, preference is given to the piperazine compounds of the formula III$^\#$, wherein A is phenyl or pyridyl where $R^a$ is attached in the ortho-position to the point of attachment of A to a carbon atom;

$R^{a\#}$ is CN, $NO_2$, $C_1$-$C_4$-alkyl, $C_1$-$C_4$-haloalkyl, $C_1$-$C_4$-alkoxy, $C_1$-$C_4$-haloalkoxy or D-C(=O)—$R^{a1}$;

$R^y$ is $C_1$-$C_6$-alkyl, $C_3$-$C_4$-alkenyl, $C_3$-$C_4$-alkynyl, $NR^A R^B$ or $C_1$-$C_4$-haloalkyl and q is 0, 1 or 2;

$R^A, R^B$ independently of one another are hydrogen, $C_1$-$C_6$-alkyl, $C_3$-$C_6$-alkenyl and $C_3$-$C_6$-alkynyl; together with the nitrogen atom to which they are attached, $R^A, R^B$ may also form a five- or six-membered saturated, partially or fully unsaturated ring which, in addition to carbon atoms, may contain 1, 2 or 3 heteroatoms selected from the group consisting of O, N and S, which ring may be substituted by 1 to 3 groups $R^{aa}$;

D is a covalent bond or $C_1$-$C_4$-alkylene;

$R^{a1}$ is hydrogen, OH, $C_1$-$C_8$-Alkyl, $C_1$-$C_4$-haloalkyl, $C_3$-$C_6$-cycloalkyl;

$R^{aa}$ is halogen, OH, CN, $NO_2$, $C_1$-$C_4$-alkyl, $C_1$-$C_4$-haloalkyl, $C_1$-$C_4$-alkoxy, $C_1$-$C_4$-haloalkoxy, $S(O)_q R^y$, D-C(=O)—$R^{a1}$ and tri-$C_1$-$C_4$-alkylsilyl;

$R^{b\#}$ independently of one another is CN, $NO_2$, halogen, $C_1$-$C_4$-alkyl, $C_1$-$C_4$-haloalkyl, $C_2$-$C_4$-alkenyl, $C_3$-$C_6$-alkynyl, $C_1$-$C_4$-alkoxy, $C_1$-$C_4$-haloalkoxy, benzyl or $S(O)_q R^y$, $R^b$ together with the group $R^a$ or $R^b$ attached to the adjacent ring atom may also form a five- or six-membered saturated or partially or fully unsaturated ring which, in addition to carbon atoms, may contain 1, 2 or 3 heteroatoms selected from the group consisting of O, N and S, which ring may be partially or fully substituted by $R^{aa}$;

p is 0 or 1;

$R^{30\#}$ is hydrogen, $C_1$-$C_{12}$-alkyl, $C_3$-$C_{12}$-alkenyl, $C_3$-$C_{12}$-alkynyl, $C_1$-$C_4$-alkoxy or $C(=O)R^{40\#}$, which can be partially or fully be substituted by $R^{aa}$ groups;

$R^{40\#}$ is hydrogen, $C_1$-$C_4$-alkyl, $C_1$-$C_4$-haloalkyl, $C_1$-$C_4$-alkoxy or $C_1$-$C_4$-haloalkoxy;

where in groups $R^{30\#}$, $R^{a\#}$ and their sub-substituents the carbon chains and/or the cyclic groups may carry 1, 2, 3 or 4 substituents $R^{aa}$ and/or $R^{a1}$;

$R^{31\#}$ is $C_1$-$C_4$-alkyl;

$R^{32\#}$ is OH, $NH_2$, $C_1$-$C_4$-alkyl, $C_3$-$C_6$-cycloalkyl, $C_1$-$C_4$-haloalkyl or $C(=O)R^{25}$;

$R^{33\#}$ is hydrogen, or $R^{33}$ and $R^{34}$ together are a covalent bond;

$R^{34\#}$, $R^{35\#}$, $R^{36\#}$, $R^{37\#}$ independently of one another are hydrogen;

$R^{38\#}$, $R^{39\#}$ independently of one another are hydrogen, halogen or OH;

b12) from the group of the decoupler herbicides:
dinoseb, dinoterb and DNOC and its salts;
b13) from the group of the auxinic herbicides:
2,4-D and its salts and esters, 2,4-DB and its salts and esters, aminopyralid and its salts such as aminopyralid-tris(2-hydroxypropyl)ammonium and its esters, benazolin, benazolin-ethyl, chloramben and its salts and esters, clomeprop, clopyralid and its salts and esters, dicamba and its salts and esters, dichlorprop and its salts and esters, dichlorprop-P and its salts and esters, fluoroxypyr, fluoroxypyr-butomethyl, fluoroxypyr-meptyl, MCPA and its salts and esters, MCPA-thioethyl, MCPB and its salts and esters, mecoprop and its salts and esters, mecoprop-P and its salts and esters, picloram and its salts and esters, quinclorac, quinmerac, TBA (2,3,6) and its salts and esters, triclopyr and its salts and esters, and aminocyclopyrachlor and its salts and esters;

b14) from the group of the auxin transport inhibitors: diflufenzopyr, diflufenzopyr-sodium, naptalam and naptalam-sodium;

b15) from the group of the other herbicides: bromobutide, chlorflurenol, chlorflurenol-methyl, cinmethylin, cumyluron, dalapon, dazomet, difenzoquat, difenzoquat-metilsulfate, dimethipin, DSMA, dymron, endothal and its salts, etobenzanid, flamprop, flamprop-isopropyl, flamprop-methyl, flamprop-M-isopropyl, flamprop-M-methyl, flurenol, flurenol-butyl, flurprimidol, fosamine, fosamine-ammonium, indanofan, indaziflam, maleic hydrazide, mefluidide, metam, methiozolin (CAS 403640-27-7), methyl azide, methyl bromide, methyl-dymron, methyl iodide, MSMA, oleic acid, oxaziclomefone, pelargonic acid, pyributicarb, quinoclamine, triaziflam, tridiphane and 6-chloro-3-(2-cyclopropyl-6-methylphenoxy)-4-pyridazinol (CAS 499223-49-3) and its salts and esters.

Moreover, it may be useful to apply the benzoxazinones of the formula I in combination with safeners. Safeners are chemical compounds which prevent or reduce damage on useful plants without having a major impact on the herbicidal action of the benzoxazinones of the formula I towards unwanted plants. They can be applied either before sowings (e.g. on seed treatments, shoots or seedlings) or in the pre-emergence application or post-emergence application of the useful plant. The safeners and the benzoxazinones of the formula I can be applied simultaneously or in succession.

Suitable safeners are e.g. (quinolin-8-oxy)acetic acids, 1-phenyl-5-haloalkyl-1H-1,2,4-triazol-3-carboxylic acids, 1-phenyl-4,5-dihydro-5-alkyl-1H-pyrazol-3,5-dicarboxylic acids, 4,5-dihydro-5,5-diaryl-3-isoxazol carboxylic acids, dichloroacetamides, alpha-oximinophenylacetonitriles, acetophenonoximes, 4,6-dihalo-2-phenylpyrimidines, N-[[4-(aminocarbonyl)phenyl]sulfonyl]-2-benzoic amides, 1,8-naphthalic anhydride, 2-halo-4-(haloalkyl)-5-thiazol carboxylic acids, phosphorthiolates and N-alkyl-O-phenylcarbamates and their agriculturally acceptable salts and their agriculturally acceptable derivatives such amides, esters, and thioesters, provided they have an acid group.

Examples of preferred safeners C are benoxacor, cloquintocet, cyometrinil, cyprosulfamide, dichlormid, dicyclonon, dietholate, fenchlorazole, fenclorim, flurazole, fluxofenim, furilazole, isoxadifen, mefenpyr, mephenate, naphthalic anhydride, oxabetrinil, 4-(dichloroacetyl)-1-oxa-4-azaspiro[4.5]decane (MON4660, CAS 71526-07-3) and 2,2,5-trimethyl-3-(dichloroacetyl)-1,3-oxazolidine (R-29148, CAS 52836-31-4).

Especially preferred safeners C are benoxacor, cloquintocet, cyprosulfamide, dichlormid, fenchlorazole, fenclorim, flurazole, fluxofenim, furilazole, isoxadifen, mefenpyr, naphthalic anhydride, oxabetrinil, 4-(dichloroacetyl)-1-oxa-4-azaspiro[4.5]decane (MON4660, CAS 71526-07-3) and 2,2,5-trimethyl-3-(dichloroacetyl)-1,3-oxazolidine (R-29148, CAS 52836-31-4).

Particularly preferred safeners C are benoxacor, cloquintocet, cyprosulfamide, dichlormid, fenchlorazole, fenclorim, furilazole, isoxadifen, mefenpyr, naphthalic anhydride, 4-(dichloroacetyl)-1-oxa-4-azaspiro[4.5]decane (MON4660, CAS 71526-07-3) and 2,2,5-trimethyl-3-(dichloroacetyl)-1,3-oxazolidine (R-29148, CAS 52836-31-4).

The active compounds of groups b1) to b15) and the safeners C are known herbicides and safeners, see, for example, The Compendium of Pesticide Common Names (http://www.alanwood.net/pesticides/); B. Hock, C. Fedtke, R. R. Schmidt, Herbizide [Herbicides], Georg Thieme Verlag, Stuttgart, 1995. Further herbicidal active compounds are known from WO 96/26202, WO 97/41116, WO 97/41117, WO 97/41118, WO 01/83459 and WO 2008/074991 and from W. Krämer et al. (ed.) "Modern Crop Protection Compounds", Vol. 1, Wiley VCH, 2007 and the literature quoted therein.

The invention also relates to compositions in the form of a crop protection composition formulated as a 1-component composition comprising an active compound combination comprising at least one benzoxazinone of the formula I and at least one further active compound, preferably selected from the active compounds of groups b1 to b15, and at least one solid or liquid carrier and/or one or more surfactants and, if desired, one or more further auxiliaries customary for crop protection compositions.

The invention also relates to compositions in the form of a crop protection composition formulated as a 2-component composition comprising a first component comprising at least one benzoxazinone of the formula I, a solid or liquid carrier and/or one or more surfactants and a second component comprising at least one further active compound selected from the active compounds of groups b1 to b15, a solid or liquid carrier and/or one or more surfactants, where additionally both components may also comprise further auxiliaries customary for crop protection compositions.

In binary compositions comprising at least one compound of the formula I as component A and at least one herbicide B, the weight ratio of the active compounds A:B is generally in the range of from 1:1000 to 1000:1, preferably in the range of from 1:500 to 500:1, in particular in the range of from 1:250 to 250:1 and particularly preferably in the range of from 1:75 to 75:1.

In binary compositions comprising at least one compound of the formula I as component A and at least one safener C, the weight ratio of the active compounds A:C is generally in the range of from 1:1000 to 1000:1, preferably in the range of from 1:500 to 500:1, in particular in the range of from 1:250 to 250:1 and particularly preferably in the range of from 1:75 to 75:1.

In ternary compositions comprising both at least one compound of the formula I as component A, at least one herbicide B and at least one safener C, the relative parts by weight of the components A:B are generally in the range of from 1:1000 to 1000:1, preferably in the range of from 1:500 to 500:1, in particular in the range of from 1:250 to 250:1 and particularly preferably in the range of from 1:75 to 75:1; the weight ratio of the components A:C is generally in the range of from 1:1000 to 1000:1, preferably in the range of from 1:500 to 500:1, in particular in the range of from 1:250 to 250:1 and particularly preferably in the range of from 1:75 to 75:1; and the weight ratio of the components B:C is generally in the range of from 1:1000 to 1000:1, preferably in the range of from 1:500 to 500:1, in particular in the range of from 1:250 to 250:1 and particularly preferably in the range of from 1:75 to 75:1. Preferably, the weight ratio of the components A+B to the component C is in the range of from 1:500 to 500:1, in particular in the range of from 1:250 to 250:1 and particularly preferably in the range of from 1:75 to 75:1.

Particularly preferred herbicides B are the herbicides B as defined above; in particular the herbicides B.1-B.144 listed below in table B:

TABLE B

| | Herbicide B |
|---|---|
| B.1 | clethodim |
| B.2 | clodinafop-propargyl |
| B.3 | cycloxydim |
| B.4 | cyhalofop-butyl |
| B.5 | fenoxaprop-P-ethyl |
| B.6 | metamifop |
| B.7 | pinoxaden |
| B.8 | profoxydim |
| B.9 | sethoxydim |
| B.10 | tepraloxydim |
| B.11 | tralkoxydim |
| B.12 | esprocarb |
| B.13 | ethofumesate |
| B.14 | molinate |
| B.15 | prosulfocarb |
| B.16 | thiobencarb |
| B.17 | triallate |
| B.18 | bensulfuron-methyl |
| B.19 | bispyribac-sodium |
| B.20 | cloransulam |
| B.21 | chlorsulfuron |
| B.22 | clorimuron |
| B.23 | cyclosulfamuron |
| B.24 | diclosulam |
| B.25 | florasulam |
| B.26 | flumetsulam |
| B.27 | flupyrsulfuron-methyl-sodium |
| B.28 | foramsulfuron |
| B.29 | imazamox |
| B.30 | imazapic |
| B.31 | imazapyr |
| B.32 | imazaquin |
| B.33 | imazethapyr |
| B.34 | imazosulfuron |
| B.35 | iodosulfuron-methyl-sodium |
| B.36 | mesosulfuron |
| B.37 | metazosulfuron |
| B.38 | metsulfuron |
| B.39 | metosulam |
| B.40 | nicosulfuron |
| B.41 | penoxsulam |
| B.42 | propoxycarbazon-sodium |
| B.43 | pyrazosulfuron-ethyl |
| B.44 | pyribenzoxim |
| B.45 | pyriftalid |
| B.46 | pyroxsulam |
| B.47 | rimsulfuron |
| B.48 | sulfosulfuron |
| B.49 | thiencarbazone-methyl |
| B.50 | thifensulfuron |
| B.51 | tribenuron |
| B.52 | tritosulfuron |
| B.53 | ametryne |
| B.54 | atrazine |
| B.55 | bentazon |
| B.56 | bromoxynil |
| B.57 | Diuron |
| B.58 | fluometuron |
| B.59 | hexazinone |
| B.60 | isoproturon |
| B.61 | Linuron |
| B.62 | metamitron |
| B.63 | metribuzin |
| B.64 | propanil |
| B.65 | simazin |
| B.66 | terbuthylazine |
| B.67 | terbutryn |
| B.68 | paraquat-dichloride |
| B.69 | acifluorfen |
| B.70 | butafenacil |
| B.71 | carfentrazone-ethyl |
| B.72 | flumioxazin |
| B.73 | fomesafen |
| B.74 | oxadiargyl |
| B.75 | oxyfluorfen |
| B.76 | saflufenacil |
| B.77 | sulfentrazone |
| B.78 | ethyl [3-[2-chloro-4-fluoro-5-(1-methyl-6-trifluoromethyl-2,4-di-oxo-1,2,3,4-tetrahydropyrimidin-3-yl)phenoxy]-2-pyridyl-oxy]acetate (CAS 353292-31-) |
| B.79 | 3-[7-fluoro-3-oxo-4-(prop-2-yn-yl)-3,4-dihydro-2H-benzo[1,4]-oxazin-6-yl]-1,5-dimethyl-6-thi-oxo-[1,3,5]triazinan-2,4-dione |
| B.80 | 1,5-dimethyl-6-thioxo-3-(2,2,7-trifluoro-3-oxo-4-(prop-2-ynyl)-3,4-dihydro-2H-benzo[b][1,4]-oxazin-6-yl)-1,3,5-triazinane-2,4-dione |
| B.81 | 2-(2,2,7-Trifluoro-3-oxo-4-prop-2-ynyl-3,4-dihydro-2H-benzo[1,4]oxazin-6-yl)-4,5,6,7-tetrahydro-isoindole-1,3-dione |
| B.82 | 1-Methyl-6-trifluoromethyl-3-(2,2,7-trifluoro-3-oxo-4-prop-2-ynyl-3,4-dihydro-2H-benzo[1,4]oxazin-6-yl)-1H-pyrimidine-2,4-dione |
| B.83 | benzobicyclon |
| B.84 | clomazone |
| B.85 | diflufenican |
| B.86 | flurochloridone |
| B.87 | isoxaflutole |
| B.88 | mesotrione |
| B.89 | norflurazone |
| B.90 | picolinafen |
| B.91 | sulcotrione |
| B.92 | tefuryltrione |
| B.93 | tembotrione |
| B.94 | topramezone |
| B.95 | bicyclopyrone |
| B.96 | amitrole |
| B.97 | fluometuron |
| B.98 | glyphosate |
| B.99 | glyphosate-isopropylammonium |
| B.100 | glyphosate-trimesium (sulfosate) |
| B.101 | glufosinate |
| B.102 | glufosinate-P |
| B.103 | glufosinate-ammonium |
| B.104 | pendimethalin |
| B.105 | trifluralin |
| B.106 | acetochlor |
| B.107 | butachlor |
| B.108 | cafenstrole |
| B.109 | dimethenamid-P |
| B.110 | fentrazamide |
| B.111 | flufenacet |
| B.112 | mefenacet |
| B.113 | metazachlor |
| B.114 | metolachlor |
| 8.115 | S-metolachlor |
| B.116 | pretilachlor |
| B.117 | fenoxasulfone |
| B.118 | isoxaben |
| B.119 | pyroxasulfone |
| B.120 | 2,4-D |
| B.121 | aminopyralid |
| B.122 | clopyralid |
| B.123 | dicamba |
| B.124 | fluroxypyr-meptyl |
| B.125 | MCPA |
| B.126 | quinclorac |
| B.127 | quinmerac |
| B.128 | aminocyclopyrachlor |
| B.129 | diflufenzopyr |
| B.130 | diflufenzopyr-sodium |
| B.131 | dymron |
| B.132 | indanofan |
| B.133 | indaziflam |
| B.134 | oxaziclomefone |
| B.135 | triaziflam |
| B.136 | II.1 |
| B.137 | II.2 |
| B.138 | II.3 |
| B.139 | II.4 |
| B.140 | II.5 |

TABLE B-continued

| | Herbicide B |
|---|---|
| B.141 | II.6 |
| B.142 | II.7 |
| B.143 | II.8 |
| B.144 | II.9 |

Particularly preferred safeners C, which, as component C, are constituent of the composition according to the invention are the safeners C as defined above; in particular the safeners C.1-C.13 listed below in table C:

TABLE C

| | Safener C |
|---|---|
| C.1 | benoxacor |
| C.2 | cloquintocet |
| C.3 | cyprosulfamide |
| C.4 | dichlormid |
| C.5 | fenchlorazole |
| C.6 | fenclorim |
| C.7 | furilazole |
| C.8 | isoxadifen |
| C.9 | mefenpyr |
| C.10 | naphtalic acid anhydride |
| C.11 | 4-(dichloroacetyl)-1-oxa-4-azaspiro[4.5]decane (MON4660, CAS 71526-07-3) |
| C.12 | 2,2,5-trimethyl-3-(dichloroacetyl)-1,3-oxazolidine (R-29148, CAS 52836-31-4) |
| C.13 | N-(2-Methoxybenzoyl)-4-[(methylaminocarbonyl)amino]benzenesulfonamide (CAS 129531-12-012-0) |

The weight ratios of the individual components in the preferred mixtures mentioned below are within the limits given above, in particular within the preferred limits.

Particularly preferred are the compositions mentioned below comprising the benzoxazinone of formula I as defined and the substance(s) as defined in the respective row of table 1;

especially preferred comprising as only herbicidal active compounds the benzoxazinone of formula I as defined and the substance(s) as defined in the respective row of table 1;

most preferably comprising as only active compounds the benzoxazinone of formula I as defined and the substance(s) as defined in the respective row of table 1.

Particularly preferred are compositions 1.1 to 1.2029, comprising the benzoxazinone Ia48 and the substance(s) as defined in the respective row of table 1:

TABLE 1

(compositions 1.1 to 1.2029):

| comp. no. | herbicide B | safener C |
|---|---|---|
| 1.1 | B.1 | — |
| 1.2 | B.2 | — |
| 1.3 | B.3 | — |
| 1.4 | B.4 | — |
| 1.5 | B.5 | — |
| 1.6 | B.6 | — |
| 1.7 | B.7 | — |
| 1.8 | B.8 | — |
| 1.9 | B.9 | — |
| 1.10 | B.10 | — |
| 1.11 | B.11 | — |
| 1.12 | B.12 | — |
| 1.13 | B.13 | — |
| 1.14 | B.14 | — |
| 1.15 | B.15 | — |
| 1.16 | B.16 | — |
| 1.17 | B.17 | — |
| 1.18 | B.18 | — |
| 1.19 | B.19 | — |
| 1.20 | B.20 | — |
| 1.21 | B.21 | — |
| 1.22 | B.22 | — |
| 1.23 | B.23 | — |
| 1.24 | B.24 | — |
| 1.25 | B.25 | — |
| 1.26 | B.26 | — |
| 1.27 | B.27 | — |
| 1.28 | B.28 | — |
| 1.29 | B.29 | — |
| 1.30 | B.30 | — |
| 1.31 | B.31 | — |
| 1.32 | B.32 | — |
| 1.33 | B.33 | — |
| 1.34 | B.34 | — |
| 1.35 | B.35 | — |
| 1.36 | B.36 | — |
| 1.37 | B.37 | — |
| 1.38 | B.38 | — |
| 1.39 | B.39 | — |
| 1.40 | B.40 | — |
| 1.41 | B.41 | — |
| 1.42 | B.42 | — |
| 1.43 | B.43 | — |
| 1.44 | B.44 | — |
| 1.45 | B.45 | — |
| 1.46 | B.46 | — |
| 1.47 | B.47 | — |
| 1.48 | B.48 | — |
| 1.49 | B.49 | — |
| 1.50 | B.50 | — |
| 1.51 | B.51 | — |
| 1.52 | B.52 | — |
| 1.53 | B.53 | — |
| 1.54 | B.54 | — |
| 1.55 | B.55 | — |
| 1.56 | B.56 | — |
| 1.57 | B.57 | — |
| 1.58 | B.58. | — |
| 1.59 | B.59 | — |
| 1.60 | B.60 | — |
| 1.61 | B.61 | — |
| 1.62 | B.62 | — |
| 1.63 | B.63 | — |
| 1.64 | B.64 | — |
| 1.65 | B.65 | — |
| 1.66 | B.66 | — |
| 1.67 | B.67 | — |
| 1.68 | B.68 | — |
| 1.69 | B.69 | — |
| 1.70 | B.70 | — |
| 1.71 | B.71 | — |
| 1.72 | B.72 | — |
| 1.73 | B.73 | — |
| 1.74 | B.74 | — |
| 1.75 | B.75 | — |
| 1.76 | B.76 | — |
| 1.77 | B.77 | — |
| 1.78 | B.78 | — |
| 1.79 | B.79 | — |
| 1.80 | B.80 | — |
| 1.81 | B.81 | — |
| 1.82 | B.82 | — |
| 1.83 | B.83 | — |
| 1.84 | B.84 | — |
| 1.85 | B.85 | — |
| 1.86 | B.86 | — |
| 1.87 | B.87 | — |
| 1.88 | B.88 | — |
| 1.89 | B.89 | — |
| 1.90 | B.90 | — |
| 1.91 | B.91 | — |
| 1.92 | B.92 | — |

TABLE 1-continued (compositions 1.1 to 1.2029):

| comp. no. | herbicide B | safener C |
|---|---|---|
| 1.93 | B.93 | — |
| 1.94 | B.94 | — |
| 1.95 | B.95 | — |
| 1.96 | B.96 | — |
| 1.97 | B.97 | — |
| 1.98 | B.98 | — |
| 1.99 | B.99 | — |
| 1.100 | B.100 | — |
| 1.101 | B.101 | — |
| 1.102 | B.102 | — |
| 1.103 | B.103 | — |
| 1.104 | B.104 | — |
| 1.105 | B.105 | — |
| 1.106 | B.106 | — |
| 1.107 | B.107 | — |
| 1.108 | B.108 | — |
| 1.109 | B.109 | — |
| 1.110 | B.110 | — |
| 1.111 | B.111 | — |
| 1.112 | B.112 | — |
| 1.113 | B.113 | — |
| 1.114 | B.114 | — |
| 1.115 | B.115 | — |
| 1.116 | B.116 | — |
| 1.117 | B.117 | — |
| 1.118 | B.118 | — |
| 1.119 | B.119 | — |
| 1.120 | B.120 | — |
| 1.121 | B.121 | — |
| 1.122 | B.122 | — |
| 1.123 | B.123 | — |
| 1.124 | B.124 | — |
| 1.125 | B.125 | — |
| 1.126 | B.126 | — |
| 1.127 | B.127 | — |
| 1.128 | B.128 | — |
| 1.129 | B.129 | — |
| 1.130 | B.130 | — |
| 1.131 | B.131 | — |
| 1.132 | B.132 | — |
| 1.133 | B.133 | — |
| 1.134 | B.134 | — |
| 1.135 | B.135 | — |
| 1.136 | B.136 | — |
| 1.137 | B.137 | — |
| 1.138 | B.138 | — |
| 1.139 | B.139 | — |
| 1.140 | B.140 | — |
| 1.141 | B.141 | — |
| 1.142 | B.142 | — |
| 1.143 | B.143 | — |
| 1.144 | B.144 | — |
| 1.145 | B.1 | C.1 |
| 1.146 | B.2 | C.1 |
| 1.147 | B.3 | C.1 |
| 1.148 | B.4 | C.1 |
| 1.149 | B.5 | C.1 |
| 1.150 | B.6 | C.1 |
| 1.151 | B.7 | C.1 |
| 1.152 | B.8 | C.1 |
| 1.153 | B.9 | C.1 |
| 1.154 | B.10 | C.1 |
| 1.155 | B.11 | C.1 |
| 1.156 | B.12 | C.1 |
| 1.157 | B.13 | C.1 |
| 1.158 | B.14 | C.1 |
| 1.159 | B.15 | C.1 |
| 1.160 | B.16 | C.1 |
| 1.161 | B.17 | C.1 |
| 1.162 | B.18 | C.1 |
| 1.163 | B.19 | C.1 |
| 1.164 | B.20 | C.1 |
| 1.165 | B.21 | C.1 |
| 1.166 | B.22 | C.1 |
| 1.167 | B.23 | C.1 |
| 1.168 | B.24 | C.1 |
| 1.169 | B.25 | C.1 |
| 1.170 | B.26 | C.1 |
| 1.171 | B.27 | C.1 |
| 1.172 | B.28 | C.1 |
| 1.173 | B.29 | C.1 |
| 1.174 | B.30 | C.1 |
| 1.175 | B.31 | C.1 |
| 1.176 | B.32 | C.1 |
| 1.177 | B.33 | C.1 |
| 1.178 | B.34 | C.1 |
| 1.179 | B.35 | C.1 |
| 1.180 | B.36 | C.1 |
| 1.181 | B.37 | C.1 |
| 1.182 | B.38 | C.1 |
| 1.183 | B.39 | C.1 |
| 1.184 | B.40 | C.1 |
| 1.185 | B.41 | C.1 |
| 1.186 | B.42 | C.1 |
| 1.187 | B.43 | C.1 |
| 1.188 | B.44 | C.1 |
| 1.189 | B.45 | C.1 |
| 1.190 | B.46 | C.1 |
| 1.191 | B.47 | C.1 |
| 1.192 | B.48 | C.1 |
| 1.193 | B.49 | C.1 |
| 1.194 | B.50 | C.1 |
| 1.195 | B.51 | C.1 |
| 1.196 | B.52 | C.1 |
| 1.197 | B.53 | C.1 |
| 1.198 | B.54 | C.1 |
| 1.199 | B.55 | C.1 |
| 1.200 | B.56 | C.1 |
| 1.201 | B.57 | C.1 |
| 1.202 | B.58. | C.1 |
| 1.203 | B.59 | C.1 |
| 1.204 | B.60 | C.1 |
| 1.205 | B.61 | C.1 |
| 1.206 | B.62 | C.1 |
| 1.207 | B.63 | C.1 |
| 1.208 | B.64 | C.1 |
| 1.209 | B.65 | C.1 |
| 1.210 | B.66 | C.1 |
| 1.211 | B.67 | C.1 |
| 1.212 | B.68 | C.1 |
| 1.213 | B.69 | C.1 |
| 1.214 | B.70 | C.1 |
| 1.215 | B.71 | C.1 |
| 1.216 | B.72 | C.1 |
| 1.217 | B.73 | C.1 |
| 1.218 | B.74 | C.1 |
| 1.219 | B.75 | C.1 |
| 1.220 | B.76 | C.1 |
| 1.221 | B.77 | C.1 |
| 1.222 | B.78 | C.1 |
| 1.223 | B.79 | C.1 |
| 1.224 | B.80 | C.1 |
| 1.225 | B.81 | C.1 |
| 1.226 | B.82 | C.1 |
| 1.227 | B.83 | C.1 |
| 1.228 | B.84 | C.1 |
| 1.229 | B.85 | C.1 |
| 1.230 | B.86 | C.1 |
| 1.231 | B.87 | C.1 |
| 1.232 | B.88 | C.1 |
| 1.233 | B.89 | C.1 |
| 1.234 | B.90 | C.1 |
| 1.235 | B.91 | C.1 |
| 1.236 | B.92 | C.1 |
| 1.237 | B.93 | C.1 |
| 1.238 | B.94 | C.1 |
| 1.239 | B.95 | C.1 |
| 1.240 | B.96 | C.1 |
| 1.241 | B.97 | C.1 |
| 1.242 | B.98 | C.1 |
| 1.243 | B.99 | C.1 |
| 1.244 | B.100 | C.1 |

TABLE 1-continued (compositions 1.1 to 1.2029):

| comp. no. | herbicide B | safener C |
|---|---|---|
| 1.245 | B.101 | C.1 |
| 1.246 | B.102 | C.1 |
| 1.247 | B.103 | C.1 |
| 1.248 | B.104 | C.1 |
| 1.249 | B.105 | C.1 |
| 1.250 | B.106 | C.1 |
| 1.251 | B.107 | C.1 |
| 1.252 | B.108 | C.1 |
| 1.253 | B.109 | C.1 |
| 1.254 | B.110 | C.1 |
| 1.255 | B.111 | C.1 |
| 1.256 | B.112 | C.1 |
| 1.257 | B.113 | C.1 |
| 1.258 | B.114 | C.1 |
| 1.259 | B.115 | C.1 |
| 1.260 | B.116 | C.1 |
| 1.261 | B.117 | C.1 |
| 1.262 | B.118 | C.1 |
| 1.263 | B.119 | C.1 |
| 1.264 | B.120 | C.1 |
| 1.265 | B.121 | C.1 |
| 1.266 | B.122 | C.1 |
| 1.267 | B.123 | C.1 |
| 1.268 | B.124 | C.1 |
| 1.269 | B.125 | C.1 |
| 1.270 | B.126 | C.1 |
| 1.271 | B.127 | C.1 |
| 1.272 | B.128 | C.1 |
| 1.273 | B.129 | C.1 |
| 1.274 | B.130 | C.1 |
| 1.275 | B.131 | C.1 |
| 1.276 | B.132 | C.1 |
| 1.277 | B.133 | C.1 |
| 1.278 | B.134 | C.1 |
| 1.279 | B.135 | C.1 |
| 1.280 | B.136 | C.1 |
| 1.281 | B.137 | C.1 |
| 1.282 | B.138 | C.1 |
| 1.283 | B.139 | C.1 |
| 1.284 | B.140 | C.1 |
| 1.285 | B.141 | C.1 |
| 1.286 | B.142 | C.1 |
| 1.287 | B.143 | C.1 |
| 1.288 | B.144 | C.1 |
| 1.289 | B.1 | C.2 |
| 1.290 | B.2 | C.2 |
| 1.291 | B.3 | C.2 |
| 1.292 | B.4 | C.2 |
| 1.293 | B.5 | C.2 |
| 1.294 | B.6 | C.2 |
| 1.295 | B.7 | C.2 |
| 1.296 | B.8 | C.2 |
| 1.297 | B.9 | C.2 |
| 1.298 | B.10 | C.2 |
| 1.299 | B.11 | C.2 |
| 1.300 | B.12 | C.2 |
| 1.301 | B.13 | C.2 |
| 1.302 | B.14 | C.2 |
| 1.303 | B.15 | C.2 |
| 1.304 | B.16 | C.2 |
| 1.305 | B.17 | C.2 |
| 1.306 | B.18 | C.2 |
| 1.307 | B.19 | C.2 |
| 1.308 | B.20 | C.2 |
| 1.309 | B.21 | C.2 |
| 1.310 | B.22 | C.2 |
| 1.311 | B.23 | C.2 |
| 1.312 | B.24 | C.2 |
| 1.313 | B.25 | C.2 |
| 1.314 | B.26 | C.2 |
| 1.315 | B.27 | C.2 |
| 1.316 | B.28 | C.2 |
| 1.317 | B.29 | C.2 |
| 1.318 | B.30 | C.2 |
| 1.319 | B.31 | C.2 |
| 1.320 | B.32 | C.2 |
| 1.321 | B.33 | C.2 |
| 1.322 | B.34 | C.2 |
| 1.323 | B.35 | C.2 |
| 1.324 | B.36 | C.2 |
| 1.325 | B.37 | C.2 |
| 1.326 | B.38 | C.2 |
| 1.327 | B.39 | C.2 |
| 1.328 | B.40 | C.2 |
| 1.329 | B.41 | C.2 |
| 1.330 | B.42 | C.2 |
| 1.331 | B.43 | C.2 |
| 1.332 | B.44 | C.2 |
| 1.333 | B.45 | C.2 |
| 1.334 | B.46 | C.2 |
| 1.335 | B.47 | C.2 |
| 1.336 | B.48 | C.2 |
| 1.337 | B.49 | C.2 |
| 1.338 | B.50 | C.2 |
| 1.339 | B.51 | C.2 |
| 1.340 | B.52 | C.2 |
| 1.341 | B.53 | C.2 |
| 1.342 | B.54 | C.2 |
| 1.343 | B.55 | C.2 |
| 1.344 | B.56 | C.2 |
| 1.345 | B.57 | C.2 |
| 1.346 | B.58. | C.2 |
| 1.347 | B.59 | C.2 |
| 1.348 | B.60 | C.2 |
| 1.349 | B.61 | C.2 |
| 1.350 | B.62 | C.2 |
| 1.351 | B.63 | C.2 |
| 1.352 | B.64 | C.2 |
| 1.353 | B.65 | C.2 |
| 1.354 | B.66 | C.2 |
| 1.355 | B.67 | C.2 |
| 1.356 | B.68 | C.2 |
| 1.357 | B.69 | C.2 |
| 1.358 | B.70 | C.2 |
| 1.359 | B.71 | C.2 |
| 1.360 | B.72 | C.2 |
| 1.361 | B.73 | C.2 |
| 1.362 | B.74 | C.2 |
| 1.363 | B.75 | C.2 |
| 1.364 | B.76 | C.2 |
| 1.365 | B.77 | C.2 |
| 1.366 | B.78 | C.2 |
| 1.367 | B.79 | C.2 |
| 1.368 | B.80 | C.2 |
| 1.369 | B.81 | C.2 |
| 1.370 | B.82 | C.2 |
| 1.371 | B.83 | C.2 |
| 1.372 | B.84 | C.2 |
| 1.373 | B.85 | C.2 |
| 1.374 | B.86 | C.2 |
| 1.375 | B.87 | C.2 |
| 1.376 | B.88 | C.2 |
| 1.377 | B.89 | C.2 |
| 1.378 | B.90 | C.2 |
| 1.379 | B.91 | C.2 |
| 1.380 | B.92 | C.2 |
| 1.381 | B.93 | C.2 |
| 1.382 | B.94 | C.2 |
| 1.383 | B.95 | C.2 |
| 1.384 | B.96 | C.2 |
| 1.385 | B.97 | C.2 |
| 1.386 | B.98 | C.2 |
| 1.387 | B.99 | C.2 |
| 1.388 | B.100 | C.2 |
| 1.389 | B.101 | C.2 |
| 1.390 | B.102 | C.2 |
| 1.391 | B.103 | C.2 |
| 1.392 | B.104 | C.2 |
| 1.393 | B.105 | C.2 |
| 1.394 | B.106 | C.2 |
| 1.395 | B.107 | C.2 |
| 1.396 | B.108 | C.2 |

TABLE 1-continued (compositions 1.1 to 1.2029):

| comp. no. | herbicide B | safener C |
|---|---|---|
| 1.397 | B.109 | C.2 |
| 1.398 | B.110 | C.2 |
| 1.399 | B.111 | C.2 |
| 1.400 | B.112 | C.2 |
| 1.401 | B.113 | C.2 |
| 1.402 | B.114 | C.2 |
| 1.403 | B.115 | C.2 |
| 1.404 | B.116 | C.2 |
| 1.405 | B.117 | C.2 |
| 1.406 | B.118 | C.2 |
| 1.407 | B.119 | C.2 |
| 1.408 | B.120 | C.2 |
| 1.409 | B.121 | C.2 |
| 1.410 | B.122 | C.2 |
| 1.411 | B.123 | C.2 |
| 1.412 | B.124 | C.2 |
| 1.413 | B.125 | C.2 |
| 1.414 | B.126 | C.2 |
| 1.415 | B.127 | C.2 |
| 1.416 | B.128 | C.2 |
| 1.417 | B.129 | C.2 |
| 1.418 | B.130 | C.2 |
| 1.419 | B.131 | C.2 |
| 1.420 | B.132 | C.2 |
| 1.421 | B.133 | C.2 |
| 1.422 | B.134 | C.2 |
| 1.423 | B.135 | C.2 |
| 1.424 | B.136 | C.2 |
| 1.425 | B.137 | C.2 |
| 1.426 | B.138 | C.2 |
| 1.427 | B.139 | C.2 |
| 1.428 | B.140 | C.2 |
| 1.429 | B.141 | C.2 |
| 1.430 | B.142 | C.2 |
| 1.431 | B.143 | C.2 |
| 1.432 | B.144 | C.2 |
| 1.433 | B.1 | C.3 |
| 1.434 | B.2 | C.3 |
| 1.435 | B.3 | C.3 |
| 1.436 | B.4 | C.3 |
| 1.437 | B.5 | C.3 |
| 1.438 | B.6 | C.3 |
| 1.439 | B.7 | C.3 |
| 1.440 | B.8 | C.3 |
| 1.441 | B.9 | C.3 |
| 1.442 | B.10 | C.3 |
| 1.443 | B.11 | C.3 |
| 1.444 | B.12 | C.3 |
| 1.445 | B.13 | C.3 |
| 1.446 | B.14 | C.3 |
| 1.447 | B.15 | C.3 |
| 1.448 | B.16 | C.3 |
| 1.449 | B.17 | C.3 |
| 1.450 | B.18 | C.3 |
| 1.451 | B.19 | C.3 |
| 1.452 | B.20 | C.3 |
| 1.453 | B.21 | C.3 |
| 1.454 | B.22 | C.3 |
| 1.455 | B.23 | C.3 |
| 1.456 | B.24 | C.3 |
| 1.457 | B.25 | C.3 |
| 1.458 | B.26 | C.3 |
| 1.459 | B.27 | C.3 |
| 1.460 | B.28 | C.3 |
| 1.461 | B.29 | C.3 |
| 1.462 | B.30 | C.3 |
| 1.463 | B.31 | C.3 |
| 1.464 | B.32 | C.3 |
| 1.465 | B.33 | C.3 |
| 1.466 | B.34 | C.3 |
| 1.467 | B.35 | C.3 |
| 1.468 | B.36 | C.3 |
| 1.469 | B.37 | C.3 |
| 1.470 | B.38 | C.3 |
| 1.471 | B.39 | C.3 |
| 1.472 | B.40 | C.3 |
| 1.473 | B.41 | C.3 |
| 1.474 | B.42 | C.3 |
| 1.475 | B.43 | C.3 |
| 1.476 | B.44 | C.3 |
| 1.477 | B.45 | C.3 |
| 1.478 | B.46 | C.3 |
| 1.479 | B.47 | C.3 |
| 1.480 | B.48 | C.3 |
| 1.481 | B.49 | C.3 |
| 1.482 | B.50 | C.3 |
| 1.483 | B.51 | C.3 |
| 1.484 | B.52 | C.3 |
| 1.485 | B.53 | C.3 |
| 1.486 | B.54 | C.3 |
| 1.487 | B.55 | C.3 |
| 1.488 | B.56 | C.3 |
| 1.489 | B.57 | C.3 |
| 1.490 | B.58. | C.3 |
| 1.491 | B.59 | C.3 |
| 1.492 | B.60 | C.3 |
| 1.493 | B.61 | C.3 |
| 1.494 | B.62 | C.3 |
| 1.495 | B.63 | C.3 |
| 1.496 | B.64 | C.3 |
| 1.497 | B.65 | C.3 |
| 1.498 | B.66 | C.3 |
| 1.499 | B.67 | C.3 |
| 1.500 | B.68 | C.3 |
| 1.501 | B.69 | C.3 |
| 1.502 | B.70 | C.3 |
| 1.503 | B.71 | C.3 |
| 1.504 | B.72 | C.3 |
| 1.505 | B.73 | C.3 |
| 1.506 | B.74 | C.3 |
| 1.507 | B.75 | C.3 |
| 1.508 | B.76 | C.3 |
| 1.509 | B.77 | C.3 |
| 1.510 | B.78 | C.3 |
| 1.511 | B.79 | C.3 |
| 1.512 | B.80 | C.3 |
| 1.513 | B.81 | C.3 |
| 1.514 | B.82 | C.3 |
| 1.515 | B.83 | C.3 |
| 1.516 | B.84 | C.3 |
| 1.517 | B.85 | C.3 |
| 1.518 | B.86 | C.3 |
| 1.519 | B.87 | C.3 |
| 1.520 | B.88 | C.3 |
| 1.521 | B.89 | C.3 |
| 1.522 | B.90 | C.3 |
| 1.523 | B.91 | C.3 |
| 1.524 | B.92 | C.3 |
| 1.525 | B.93 | C.3 |
| 1.526 | B.94 | C.3 |
| 1.527 | B.95 | C.3 |
| 1.528 | B.96 | C.3 |
| 1.529 | B.97 | C.3 |
| 1.530 | B.98 | C.3 |
| 1.531 | B.99 | C.3 |
| 1.532 | B.100 | C.3 |
| 1.533 | B.101 | C.3 |
| 1.534 | B.102 | C.3 |
| 1.535 | B.103 | C.3 |
| 1.536 | B.104 | C.3 |
| 1.537 | B.105 | C.3 |
| 1.538 | B.106 | C.3 |
| 1.539 | B.107 | C.3 |
| 1.540 | B.108 | C.3 |
| 1.541 | B.109 | C.3 |
| 1.542 | B.110 | C.3 |
| 1.543 | B.111 | C.3 |
| 1.544 | B.112 | C.3 |
| 1.545 | B.113 | C.3 |
| 1.546 | B.114 | C.3 |
| 1.547 | B.115 | C.3 |
| 1.548 | B.116 | C.3 |

TABLE 1-continued (compositions 1.1 to 1.2029):

| comp. no. | herbicide B | safener C |
|---|---|---|
| 1.549 | B.117 | C.3 |
| 1.550 | B.118 | C.3 |
| 1.551 | B.119 | C.3 |
| 1.552 | B.120 | C.3 |
| 1.553 | B.121 | C.3 |
| 1.554 | B.122 | C.3 |
| 1.555 | B.123 | C.3 |
| 1.556 | B.124 | C.3 |
| 1.557 | B.125 | C.3 |
| 1.558 | B.126 | C.3 |
| 1.559 | B.127 | C.3 |
| 1.560 | B.128 | C.3 |
| 1.561 | B.129 | C.3 |
| 1.562 | B.130 | C.3 |
| 1.563 | B.131 | C.3 |
| 1.564 | B.132 | C.3 |
| 1.565 | B.133 | C.3 |
| 1.566 | B.134 | C.3 |
| 1.567 | B.135 | C.3 |
| 1.568 | B.136 | C.3 |
| 1.569 | B.137 | C.3 |
| 1.570 | B.138 | C.3 |
| 1.571 | B.139 | C.3 |
| 1.572 | B.140 | C.3 |
| 1.573 | B.141 | C.3 |
| 1.574 | B.142 | C.3 |
| 1.575 | B.143 | C.3 |
| 1.576 | B.144 | C.3 |
| 1.577 | B.1 | C.4 |
| 1.578 | B.2 | C.4 |
| 1.579 | B.3 | C.4 |
| 1.580 | B.4 | C.4 |
| 1.581 | B.5 | C.4 |
| 1.582 | B.6 | C.4 |
| 1.583 | B.7 | C.4 |
| 1.584 | B.8 | C.4 |
| 1.585 | B.9 | C.4 |
| 1.586 | B.10 | C.4 |
| 1.587 | B.11 | C.4 |
| 1.588 | B.12 | C.4 |
| 1.589 | B.13 | C.4 |
| 1.590 | B.14 | C.4 |
| 1.591 | B.15 | C.4 |
| 1.592 | B.16 | C.4 |
| 1.593 | B.17 | C.4 |
| 1.594 | B.18 | C.4 |
| 1.595 | B.19 | C.4 |
| 1.596 | B.20 | C.4 |
| 1.597 | B.21 | C.4 |
| 1.598 | B.22 | C.4 |
| 1.599 | B.23 | C.4 |
| 1.600 | B.24 | C.4 |
| 1.601 | B.25 | C.4 |
| 1.602 | B.26 | C.4 |
| 1.603 | B.27 | C.4 |
| 1.604 | B.28 | C.4 |
| 1.605 | B.29 | C.4 |
| 1.606 | B.30 | C.4 |
| 1.607 | B.31 | C.4 |
| 1.608 | B.32 | C.4 |
| 1.609 | B.33 | C.4 |
| 1.610 | B.34 | C.4 |
| 1.611 | B.35 | C.4 |
| 1.612 | B.36 | C.4 |
| 1.613 | B.37 | C.4 |
| 1.614 | B.38 | C.4 |
| 1.615 | B.39 | C.4 |
| 1.616 | B.40 | C.4 |
| 1.617 | B.41 | C.4 |
| 1.618 | B.42 | C.4 |
| 1.619 | B.43 | C.4 |
| 1.620 | B.44 | C.4 |
| 1.621 | B.45 | C.4 |
| 1.622 | B.46 | C.4 |
| 1.623 | B.47 | C.4 |
| 1.624 | B.48 | C.4 |
| 1.625 | B.49 | C.4 |
| 1.626 | B.50 | C.4 |
| 1.627 | B.51 | C.4 |
| 1.628 | B.52 | C.4 |
| 1.629 | B.53 | C.4 |
| 1.630 | B.54 | C.4 |
| 1.631 | B.55 | C.4 |
| 1.632 | B.56 | C.4 |
| 1.633 | B.57 | C.4 |
| 1.634 | B.58. | C.4 |
| 1.635 | B.59 | C.4 |
| 1.636 | B.60 | C.4 |
| 1.637 | B.61 | C.4 |
| 1.638 | B.62 | C.4 |
| 1.639 | B.63 | C.4 |
| 1.640 | B.64 | C.4 |
| 1.641 | B.65 | C.4 |
| 1.642 | B.66 | C.4 |
| 1.643 | B.67 | C.4 |
| 1.644 | B.68 | C.4 |
| 1.645 | B.69 | C.4 |
| 1.646 | B.70 | C.4 |
| 1.647 | B.71 | C.4 |
| 1.648 | B.72 | C.4 |
| 1.649 | B.73 | C.4 |
| 1.650 | B.74 | C.4 |
| 1.651 | B.75 | C.4 |
| 1.652 | B.76 | C.4 |
| 1.653 | B.77 | C.4 |
| 1.654 | B.78 | C.4 |
| 1.655 | B.79 | C.4 |
| 1.656 | B.80 | C.4 |
| 1.657 | B.81 | C.4 |
| 1.658 | B.82 | C.4 |
| 1.659 | B.83 | C.4 |
| 1.660 | B.84 | C.4 |
| 1.661 | B.85 | C.4 |
| 1.662 | B.86 | C.4 |
| 1.663 | B.87 | C.4 |
| 1.664 | B.88 | C.4 |
| 1.665 | B.89 | C.4 |
| 1.666 | B.90 | C.4 |
| 1.667 | B.91 | C.4 |
| 1.668 | B.92 | C.4 |
| 1.669 | B.93 | C.4 |
| 1.670 | B.94 | C.4 |
| 1.671 | B.95 | C.4 |
| 1.672 | B.96 | C.4 |
| 1.673 | B.97 | C.4 |
| 1.674 | B.98 | C.4 |
| 1.675 | B.99 | C.4 |
| 1.676 | B.100 | C.4 |
| 1.677 | B.101 | C.4 |
| 1.678 | B.102 | C.4 |
| 1.679 | B.103 | C.4 |
| 1.680 | B.104 | C.4 |
| 1.681 | B.105 | C.4 |
| 1.682 | B.106 | C.4 |
| 1.683 | B.107 | C.4 |
| 1.684 | B.108 | C.4 |
| 1.685 | B.109 | C.4 |
| 1.686 | B.110 | C.4 |
| 1.687 | B.111 | C.4 |
| 1.688 | B.112 | C.4 |
| 1.689 | B.113 | C.4 |
| 1.690 | B.114 | C.4 |
| 1.691 | B.115 | C.4 |
| 1.692 | B.116 | C.4 |
| 1.693 | B.117 | C.4 |
| 1.694 | B.118 | C.4 |
| 1.695 | B.119 | C.4 |
| 1.696 | B.120 | C.4 |
| 1.697 | B.121 | C.4 |
| 1.698 | B.122 | C.4 |
| 1.699 | B.123 | C.4 |
| 1.700 | B.124 | C.4 |

TABLE 1-continued (compositions 1.1 to 1.2029):

| comp. no. | herbicide B | safener C |
|---|---|---|
| 1.701 | B.125 | C.4 |
| 1.702 | B.126 | C.4 |
| 1.703 | B.127 | C.4 |
| 1.704 | B.128 | C.4 |
| 1.705 | B.129 | C.4 |
| 1.706 | B.130 | C.4 |
| 1.707 | B.131 | C.4 |
| 1.708 | B.132 | C.4 |
| 1.709 | B.133 | C.4 |
| 1.710 | B.134 | C.4 |
| 1.711 | B.135 | C.4 |
| 1.712 | B.136 | C.4 |
| 1.713 | B.137 | C.4 |
| 1.714 | B.138 | C.4 |
| 1.715 | B.139 | C.4 |
| 1.716 | B.140 | C.4 |
| 1.717 | B.141 | C.4 |
| 1.718 | B.142 | C.4 |
| 1.719 | B.143 | C.4 |
| 1.720 | B.144 | C.4 |
| 1.721 | B.1 | C.5 |
| 1.722 | B.2 | C.5 |
| 1.723 | B.3 | C.5 |
| 1.724 | B.4 | C.5 |
| 1.725 | B.5 | C.5 |
| 1.726 | B.6 | C.5 |
| 1.727 | B.7 | C.5 |
| 1.728 | B.8 | C.5 |
| 1.729 | B.9 | C.5 |
| 1.730 | B.10 | C.5 |
| 1.731 | B.11 | C.5 |
| 1.732 | B.12 | C.5 |
| 1.733 | B.13 | C.5 |
| 1.734 | B.14 | C.5 |
| 1.735 | B.15 | C.5 |
| 1.736 | B.16 | C.5 |
| 1.737 | B.17 | C.5 |
| 1.738 | B.18 | C.5 |
| 1.739 | B.19 | C.5 |
| 1.740 | B.20 | C.5 |
| 1.741 | B.21 | C.5 |
| 1.742 | B.22 | C.5 |
| 1.743 | B.23 | C.5 |
| 1.744 | B.24 | C.5 |
| 1.745 | B.25 | C.5 |
| 1.746 | B.26 | C.5 |
| 1.747 | B.27 | C.5 |
| 1.748 | B.28 | C.5 |
| 1.749 | B.29 | C.5 |
| 1.750 | B.30 | C.5 |
| 1.751 | B.31 | C.5 |
| 1.752 | B.32 | C.5 |
| 1.753 | B.33 | C.5 |
| 1.754 | B.34 | C.5 |
| 1.755 | B.35 | C.5 |
| 1.756 | B.36 | C.5 |
| 1.757 | B.37 | C.5 |
| 1.758 | B.38 | C.5 |
| 1.759 | B.39 | C.5 |
| 1.760 | B.40 | C.5 |
| 1.761 | B.41 | C.5 |
| 1.762 | B.42 | C.5 |
| 1.763 | B.43 | C.5 |
| 1.764 | B.44 | C.5 |
| 1.765 | B.45 | C.5 |
| 1.766 | B.46 | C.5 |
| 1.767 | B.47 | C.5 |
| 1.768 | B.48 | C.5 |
| 1.769 | B.49 | C.5 |
| 1.770 | B.50 | C.5 |
| 1.771 | B.51 | C.5 |
| 1.772 | B.52 | C.5 |
| 1.773 | B.53 | C.5 |
| 1.774 | B.54 | C.5 |
| 1.775 | B.55 | C.5 |
| 1.776 | B.56 | C.5 |
| 1.777 | B.57 | C.5 |
| 1.778 | B.58. | C.5 |
| 1.779 | B.59 | C.5 |
| 1.780 | B.60 | C.5 |
| 1.781 | B.61 | C.5 |
| 1.782 | B.62 | C.5 |
| 1.783 | B.63 | C.5 |
| 1.784 | B.64 | C.5 |
| 1.785 | B.65 | C.5 |
| 1.786 | B.66 | C.5 |
| 1.787 | B.67 | C.5 |
| 1.788 | B.68 | C.5 |
| 1.789 | B.69 | C.5 |
| 1.790 | B.70 | C.5 |
| 1.791 | B.71 | C.5 |
| 1.792 | B.72 | C.5 |
| 1.793 | B.73 | C.5 |
| 1.794 | B.74 | C.5 |
| 1.795 | B.75 | C.5 |
| 1.796 | B.76 | C.5 |
| 1.797 | B.77 | C.5 |
| 1.798 | B.78 | C.5 |
| 1.799 | B.79 | C.5 |
| 1.800 | B.80 | C.5 |
| 1.801 | B.81 | C.5 |
| 1.802 | B.82 | C.5 |
| 1.803 | B.83 | C.5 |
| 1.804 | B.84 | C.5 |
| 1.805 | B.85 | C.5 |
| 1.806 | B.86 | C.5 |
| 1.807 | B.87 | C.5 |
| 1.808 | B.88 | C.5 |
| 1.809 | B.89 | C.5 |
| 1.810 | B.90 | C.5 |
| 1.811 | B.91 | C.5 |
| 1.812 | B.92 | C.5 |
| 1.813 | B.93 | C.5 |
| 1.814 | B.94 | C.5 |
| 1.815 | B.95 | C.5 |
| 1.816 | B.96 | C.5 |
| 1.817 | B.97 | C.5 |
| 1.818 | B.98 | C.5 |
| 1.819 | B.99 | C.5 |
| 1.820 | B.100 | C.5 |
| 1.821 | B.101 | C.5 |
| 1.822 | B.102 | C.5 |
| 1.823 | B.103 | C.5 |
| 1.824 | B.104 | C.5 |
| 1.825 | B.105 | C.5 |
| 1.826 | B.106 | C.5 |
| 1.827 | B.107 | C.5 |
| 1.828 | B.108 | C.5 |
| 1.829 | B.109 | C.5 |
| 1.830 | B.110 | C.5 |
| 1.831 | B.111 | C.5 |
| 1.832 | B.112 | C.5 |
| 1.833 | B.113 | C.5 |
| 1.834 | B.114 | C.5 |
| 1.835 | B.115 | C.5 |
| 1.836 | B.116 | C.5 |
| 1.837 | B.117 | C.5 |
| 1.838 | B.118 | C.5 |
| 1.839 | B.119 | C.5 |
| 1.840 | B.120 | C.5 |
| 1.841 | B.121 | C.5 |
| 1.842 | B.122 | C.5 |
| 1.843 | B.123 | C.5 |
| 1.844 | B.124 | C.5 |
| 1.845 | B.125 | C.5 |
| 1.846 | B.126 | C.5 |
| 1.847 | B.127 | C.5 |
| 1.848 | B.128 | C.5 |
| 1.849 | B.129 | C.5 |
| 1.850 | B.130 | C.5 |
| 1.851 | B.131 | C.5 |
| 1.852 | B.132 | C.5 |

TABLE 1-continued (compositions 1.1 to 1.2029):

| comp. no. | herbicide B | safener C |
|---|---|---|
| 1.853 | B.133 | C.5 |
| 1.854 | B.134 | C.5 |
| 1.855 | B.135 | C.5 |
| 1.856 | B.136 | C.5 |
| 1.857 | B.137 | C.5 |
| 1.858 | B.138 | C.5 |
| 1.859 | B.139 | C.5 |
| 1.860 | B.140 | C.5 |
| 1.861 | B.141 | C.5 |
| 1.862 | B.142 | C.5 |
| 1.863 | B.143 | C.5 |
| 1.864 | B.144 | C.5 |
| 1.865 | B.1 | C.6 |
| 1.866 | B.2 | C.6 |
| 1.867 | B.3 | C.6 |
| 1.868 | B.4 | C.6 |
| 1.869 | B.5 | C.6 |
| 1.870 | B.6 | C.6 |
| 1.871 | B.7 | C.6 |
| 1.872 | B.8 | C.6 |
| 1.873 | B.9 | C.6 |
| 1.874 | B.10 | C.6 |
| 1.875 | B.11 | C.6 |
| 1.876 | B.12 | C.6 |
| 1.877 | B.13 | C.6 |
| 1.878 | B.14 | C.6 |
| 1.879 | B.15 | C.6 |
| 1.880 | B.16 | C.6 |
| 1.881 | B.17 | C.6 |
| 1.882 | B.18 | C.6 |
| 1.883 | B.19 | C.6 |
| 1.884 | B.20 | C.6 |
| 1.885 | B.21 | C.6 |
| 1.886 | B.22 | C.6 |
| 1.887 | B.23 | C.6 |
| 1.888 | B.24 | C.6 |
| 1.889 | B.25 | C.6 |
| 1.890 | B.26 | C.6 |
| 1.891 | B.27 | C.6 |
| 1.892 | B.28 | C.6 |
| 1.893 | B.29 | C.6 |
| 1.894 | B.30 | C.6 |
| 1.895 | B.31 | C.6 |
| 1.896 | B.32 | C.6 |
| 1.897 | B.33 | C.6 |
| 1.898 | B.34 | C.6 |
| 1.899 | B.35 | C.6 |
| 1.900 | B.36 | C.6 |
| 1.901 | B.37 | C.6 |
| 1.902 | B.38 | C.6 |
| 1.903 | B.39 | C.6 |
| 1.904 | B.40 | C.6 |
| 1.905 | B.41 | C.6 |
| 1.906 | B.42 | C.6 |
| 1.907 | B.43 | C.6 |
| 1.908 | B.44 | C.6 |
| 1.909 | B.45 | C.6 |
| 1.910 | B.46 | C.6 |
| 1.911 | B.47 | C.6 |
| 1.912 | B.48 | C.6 |
| 1.913 | B.49 | C.6 |
| 1.914 | B.50 | C.6 |
| 1.915 | B.51 | C.6 |
| 1.916 | B.52 | C.6 |
| 1.917 | B.53 | C.6 |
| 1.918 | B.54 | C.6 |
| 1.919 | B.55 | C.6 |
| 1.920 | B.56 | C.6 |
| 1.921 | B.57 | C.6 |
| 1.922 | B.58. | C.6 |
| 1.923 | B.59 | C.6 |
| 1.924 | B.60 | C.6 |
| 1.925 | B.61 | C.6 |
| 1.926 | B.62 | C.6 |
| 1.927 | B.63 | C.6 |
| 1.928 | B.64 | C.6 |
| 1.929 | B.65 | C.6 |
| 1.930 | B.66 | C.6 |
| 1.931 | B.67 | C.6 |
| 1.932 | B.68 | C.6 |
| 1.933 | B.69 | C.6 |
| 1.934 | B.70 | C.6 |
| 1.935 | B.71 | C.6 |
| 1.936 | B.72 | C.6 |
| 1.937 | B.73 | C.6 |
| 1.938 | B.74 | C.6 |
| 1.939 | B.75 | C.6 |
| 1.940 | B.76 | C.6 |
| 1.941 | B.77 | C.6 |
| 1.942 | B.78 | C.6 |
| 1.943 | B.79 | C.6 |
| 1.944 | B.80 | C.6 |
| 1.945 | B.81 | C.6 |
| 1.946 | B.82 | C.6 |
| 1.947 | B.83 | C.6 |
| 1.948 | B.84 | C.6 |
| 1.949 | B.85 | C.6 |
| 1.950 | B.86 | C.6 |
| 1.951 | B.87 | C.6 |
| 1.952 | B.88 | C.6 |
| 1.953 | B.89 | C.6 |
| 1.954 | B.90 | C.6 |
| 1.955 | B.91 | C.6 |
| 1.956 | B.92 | C.6 |
| 1.957 | B.93 | C.6 |
| 1.958 | B.94 | C.6 |
| 1.959 | B.95 | C.6 |
| 1.960 | B.96 | C.6 |
| 1.961 | B.97 | C.6 |
| 1.962 | B.98 | C.6 |
| 1.963 | B.99 | C.6 |
| 1.964 | B.100 | C.6 |
| 1.965 | B.101 | C.6 |
| 1.966 | B.102 | C.6 |
| 1.967 | B.103 | C.6 |
| 1.968 | B.104 | C.6 |
| 1.969 | B.105 | C.6 |
| 1.970 | B.106 | C.6 |
| 1.971 | B.107 | C.6 |
| 1.972 | B.108 | C.6 |
| 1.973 | B.109 | C.6 |
| 1.974 | B.110 | C.6 |
| 1.975 | B.111 | C.6 |
| 1.976 | B.112 | C.6 |
| 1.977 | B.113 | C.6 |
| 1.978 | B.114 | C.6 |
| 1.979 | B.115 | C.6 |
| 1.980 | B.116 | C.6 |
| 1.981 | B.117 | C.6 |
| 1.982 | B.118 | C.6 |
| 1.983 | B.119 | C.6 |
| 1.984 | B.120 | C.6 |
| 1.985 | B.121 | C.6 |
| 1.986 | B.122 | C.6 |
| 1.987 | B.123 | C.6 |
| 1.988 | B.124 | C.6 |
| 1.989 | B.125 | C.6 |
| 1.990 | B.126 | C.6 |
| 1.991 | B.127 | C.6 |
| 1.992 | B.128 | C.6 |
| 1.993 | B.129 | C.6 |
| 1.994 | B.130 | C.6 |
| 1.995 | B.131 | C.6 |
| 1.996 | B.132 | C.6 |
| 1.997 | B.133 | C.6 |
| 1.998 | B.134 | C.6 |
| 1.999 | B.135 | C.6 |
| 1.1000 | B.136 | C.6 |
| 1.1001 | B.137 | C.6 |
| 1.1002 | B.138 | C.6 |
| 1.1003 | B.139 | C.6 |
| 1.1004 | B.140 | C.6 |

TABLE 1-continued (compositions 1.1 to 1.2029):

| comp. no. | herbicide B | safener C |
|---|---|---|
| 1.1005 | B.141 | C.6 |
| 1.1006 | B.142 | C.6 |
| 1.1007 | B.143 | C.6 |
| 1.1008 | B.144 | C.6 |
| 1.1009 | B.1 | C.7 |
| 1.1010 | B.2 | C.7 |
| 1.1011 | B.3 | C.7 |
| 1.1012 | B.4 | C.7 |
| 1.1013 | B.5 | C.7 |
| 1.1014 | B.6 | C.7 |
| 1.1015 | B.7 | C.7 |
| 1.1016 | B.8 | C.7 |
| 1.1017 | B.9 | C.7 |
| 1.1018 | B.10 | C.7 |
| 1.1019 | B.11 | C.7 |
| 1.1020 | B.12 | C.7 |
| 1.1021 | B.13 | C.7 |
| 1.1022 | B.14 | C.7 |
| 1.1023 | B.15 | C.7 |
| 1.1024 | B.16 | C.7 |
| 1.1025 | B.17 | C.7 |
| 1.1026 | B.18 | C.7 |
| 1.1027 | B.19 | C.7 |
| 1.1028 | B.20 | C.7 |
| 1.1029 | B.21 | C.7 |
| 1.1030 | B.22 | C.7 |
| 1.1031 | B.23 | C.7 |
| 1.1032 | B.24 | C.7 |
| 1.1033 | B.25 | C.7 |
| 1.1034 | B.26 | C.7 |
| 1.1035 | B.27 | C.7 |
| 1.1036 | B.28 | C.7 |
| 1.1037 | B.29 | C.7 |
| 1.1038 | B.30 | C.7 |
| 1.1039 | B.31 | C.7 |
| 1.1040 | B.32 | C.7 |
| 1.1041 | B.33 | C.7 |
| 1.1042 | B.34 | C.7 |
| 1.1043 | B.35 | C.7 |
| 1.1044 | B.36 | C.7 |
| 1.1045 | B.37 | C.7 |
| 1.1046 | B.38 | C.7 |
| 1.1047 | B.39 | C.7 |
| 1.1048 | B.40 | C.7 |
| 1.1049 | B.41 | C.7 |
| 1.1050 | B.42 | C.7 |
| 1.1051 | B.43 | C.7 |
| 1.1052 | B.44 | C.7 |
| 1.1053 | B.45 | C.7 |
| 1.1054 | B.46 | C.7 |
| 1.1055 | B.47 | C.7 |
| 1.1056 | B.48 | C.7 |
| 1.1057 | B.49 | C.7 |
| 1.1058 | B.50 | C.7 |
| 1.1059 | B.51 | C.7 |
| 1.1060 | B.52 | C.7 |
| 1.1061 | B.53 | C.7 |
| 1.1062 | B.54 | C.7 |
| 1.1063 | B.55 | C.7 |
| 1.1064 | B.56 | C.7 |
| 1.1065 | B.57 | C.7 |
| 1.1066 | B.58. | C.7 |
| 1.1067 | B.59 | C.7 |
| 1.1068 | B.60 | C.7 |
| 1.1069 | B.61 | C.7 |
| 1.1070 | B.62 | C.7 |
| 1.1071 | B.63 | C.7 |
| 1.1072 | B.64 | C.7 |
| 1.1073 | B.65 | C.7 |
| 1.1074 | B.66 | C.7 |
| 1.1075 | B.67 | C.7 |
| 1.1076 | B.68 | C.7 |
| 1.1077 | B.69 | C.7 |
| 1.1078 | B.70 | C.7 |
| 1.1079 | B.71 | C.7 |
| 1.1080 | B.72 | C.7 |
| 1.1081 | B.73 | C.7 |
| 1.1082 | B.74 | C.7 |
| 1.1083 | B.75 | C.7 |
| 1.1084 | B.76 | C.7 |
| 1.1085 | B.77 | C.7 |
| 1.1086 | B.78 | C.7 |
| 1.1087 | B.79 | C.7 |
| 1.1088 | B.80 | C.7 |
| 1.1089 | B.81 | C.7 |
| 1.1090 | B.82 | C.7 |
| 1.1091 | B.83 | C.7 |
| 1.1092 | B.84 | C.7 |
| 1.1093 | B.85 | C.7 |
| 1.1094 | B.86 | C.7 |
| 1.1095 | B.87 | C.7 |
| 1.1096 | B.88 | C.7 |
| 1.1097 | B.89 | C.7 |
| 1.1098 | B.90 | C.7 |
| 1.1099 | B.91 | C.7 |
| 1.1100 | B.92 | C.7 |
| 1.1101 | B.93 | C.7 |
| 1.1102 | B.94 | C.7 |
| 1.1103 | B.95 | C.7 |
| 1.1104 | B.96 | C.7 |
| 1.1105 | B.97 | C.7 |
| 1.1106 | B.98 | C.7 |
| 1.1107 | B.99 | C.7 |
| 1.1108 | B.100 | C.7 |
| 1.1109 | B.101 | C.7 |
| 1.1110 | B.102 | C.7 |
| 1.1111 | B.103 | C.7 |
| 1.1112 | B.104 | C.7 |
| 1.1113 | B.105 | C.7 |
| 1.1114 | B.106 | C.7 |
| 1.1115 | B.107 | C.7 |
| 1.1116 | B.108 | C.7 |
| 1.1117 | B.109 | C.7 |
| 1.1118 | B.110 | C.7 |
| 1.1119 | B.111 | C.7 |
| 1.1120 | B.112 | C.7 |
| 1.1121 | B.113 | C.7 |
| 1.1122 | B.114 | C.7 |
| 1.1123 | B.115 | C.7 |
| 1.1124 | B.116 | C.7 |
| 1.1125 | B.117 | C.7 |
| 1.1126 | B.118 | C.7 |
| 1.1127 | B.119 | C.7 |
| 1.1128 | B.120 | C.7 |
| 1.1129 | B.121 | C.7 |
| 1.1130 | B.122 | C.7 |
| 1.1131 | B.123 | C.7 |
| 1.1132 | B.124 | C.7 |
| 1.1133 | B.125 | C.7 |
| 1.1134 | B.126 | C.7 |
| 1.1135 | B.127 | C.7 |
| 1.1136 | B.128 | C.7 |
| 1.1137 | B.129 | C.7 |
| 1.1138 | B.130 | C.7 |
| 1.1139 | B.131 | C.7 |
| 1.1140 | B.132 | C.7 |
| 1.1141 | B.133 | C.7 |
| 1.1142 | B.134 | C.7 |
| 1.1143 | B.135 | C.7 |
| 1.1144 | B.136 | C.7 |
| 1.1145 | B.137 | C.7 |
| 1.1146 | B.138 | C.7 |
| 1.1147 | B.139 | C.7 |
| 1.1148 | B.140 | C.7 |
| 1.1149 | B.141 | C.7 |
| 1.1150 | B.142 | C.7 |
| 1.1151 | B.143 | C.7 |
| 1.1152 | B.144 | C.7 |
| 1.1153 | B.1 | C.8 |
| 1.1154 | B.2 | C.8 |
| 1.1155 | B.3 | C.8 |
| 1.1156 | B.4 | C.8 |

TABLE 1-continued (compositions 1.1 to 1.2029):

| comp. no. | herbicide B | safener C |
|---|---|---|
| 1.1157 | B.5 | C.8 |
| 1.1158 | B.6 | C.8 |
| 1.1159 | B.7 | C.8 |
| 1.1160 | B.8 | C.8 |
| 1.1161 | B.9 | C.8 |
| 1.1162 | B.10 | C.8 |
| 1.1163 | B.11 | C.8 |
| 1.1164 | B.12 | C.8 |
| 1.1165 | B.13 | C.8 |
| 1.1166 | B.14 | C.8 |
| 1.1167 | B.15 | C.8 |
| 1.1168 | B.16 | C.8 |
| 1.1169 | B.17 | C.8 |
| 1.1170 | B.18 | C.8 |
| 1.1171 | B.19 | C.8 |
| 1.1172 | B.20 | C.8 |
| 1.1173 | B.21 | C.8 |
| 1.1174 | B.22 | C.8 |
| 1.1175 | B.23 | C.8 |
| 1.1176 | B.24 | C.8 |
| 1.1177 | B.25 | C.8 |
| 1.1178 | B.26 | C.8 |
| 1.1179 | B.27 | C.8 |
| 1.1180 | B.28 | C.8 |
| 1.1181 | B.29 | C.8 |
| 1.1182 | B.30 | C.8 |
| 1.1183 | B.31 | C.8 |
| 1.1184 | B.32 | C.8 |
| 1.1185 | B.33 | C.8 |
| 1.1186 | B.34 | C.8 |
| 1.1187 | B.35 | C.8 |
| 1.1188 | B.36 | C.8 |
| 1.1189 | B.37 | C.8 |
| 1.1190 | B.38 | C.8 |
| 1.1191 | B.39 | C.8 |
| 1.1192 | B.40 | C.8 |
| 1.1193 | B.41 | C.8 |
| 1.1194 | B.42 | C.8 |
| 1.1195 | B.43 | C.8 |
| 1.1196 | B.44 | C.8 |
| 1.1197 | B.45 | C.8 |
| 1.1198 | B.46 | C.8 |
| 1.1199 | B.47 | C.8 |
| 1.1200 | B.48 | C.8 |
| 1.1201 | B.49 | C.8 |
| 1.1202 | B.50 | C.8 |
| 1.1203 | B.51 | C.8 |
| 1.1204 | B.52 | C.8 |
| 1.1205 | B.53 | C.8 |
| 1.1206 | B.54 | C.8 |
| 1.1207 | B.55 | C.8 |
| 1.1208 | B.56 | C.8 |
| 1.1209 | B.57 | C.8 |
| 1.1210 | B.58. | C.8 |
| 1.1211 | B.59 | C.8 |
| 1.1212 | B.60 | C.8 |
| 1.1213 | B.61 | C.8 |
| 1.1214 | B.62 | C.8 |
| 1.1215 | B.63 | C.8 |
| 1.1216 | B.64 | C.8 |
| 1.1217 | B.65 | C.8 |
| 1.1218 | B.66 | C.8 |
| 1.1219 | B.67 | C.8 |
| 1.1220 | B.68 | C.8 |
| 1.1221 | B.69 | C.8 |
| 1.1222 | B.70 | C.8 |
| 1.1223 | B.71 | C.8 |
| 1.1224 | B.72 | C.8 |
| 1.1225 | B.73 | C.8 |
| 1.1226 | B.74 | C.8 |
| 1.1227 | B.75 | C.8 |
| 1.1228 | B.76 | C.8 |
| 1.1229 | B.77 | C.8 |
| 1.1230 | B.78 | C.8 |
| 1.1231 | B.79 | C.8 |
| 1.1232 | B.80 | C.8 |
| 1.1233 | B.81 | C.8 |
| 1.1234 | B.82 | C.8 |
| 1.1235 | B.83 | C.8 |
| 1.1236 | B.84 | C.8 |
| 1.1237 | B.85 | C.8 |
| 1.1238 | B.86 | C.8 |
| 1.1239 | B.87 | C.8 |
| 1.1240 | B.88 | C.8 |
| 1.1241 | B.89 | C.8 |
| 1.1242 | B.90 | C.8 |
| 1.1243 | B.91 | C.8 |
| 1.1244 | B.92 | C.8 |
| 1.1245 | B.93 | C.8 |
| 1.1246 | B.94 | C.8 |
| 1.1247 | B.95 | C.8 |
| 1.1248 | B.96 | C.8 |
| 1.1249 | B.97 | C.8 |
| 1.1250 | B.98 | C.8 |
| 1.1251 | B.99 | C.8 |
| 1.1252 | B.100 | C.8 |
| 1.1253 | B.101 | C.8 |
| 1.1254 | B.102 | C.8 |
| 1.1255 | B.103 | C.8 |
| 1.1256 | B.104 | C.8 |
| 1.1257 | B.105 | C.8 |
| 1.1258 | B.106 | C.8 |
| 1.1259 | B.107 | C.8 |
| 1.1260 | B.108 | C.8 |
| 1.1261 | B.109 | C.8 |
| 1.1262 | B.110 | C.8 |
| 1.1263 | B.111 | C.8 |
| 1.1264 | B.112 | C.8 |
| 1.1265 | B.113 | C.8 |
| 1.1266 | B.114 | C.8 |
| 1.1267 | B.115 | C.8 |
| 1.1268 | B.116 | C.8 |
| 1.1269 | B.117 | C.8 |
| 1.1270 | B.118 | C.8 |
| 1.1271 | B.119 | C.8 |
| 1.1272 | B.120 | C.8 |
| 1.1273 | B.121 | C.8 |
| 1.1274 | B.122 | C.8 |
| 1.1275 | B.123 | C.8 |
| 1.1276 | B.124 | C.8 |
| 1.1277 | B.125 | C.8 |
| 1.1278 | B.126 | C.8 |
| 1.1279 | B.127 | C.8 |
| 1.1280 | B.128 | C.8 |
| 1.1281 | B.129 | C.8 |
| 1.1282 | B.130 | C.8 |
| 1.1283 | B.131 | C.8 |
| 1.1284 | B.132 | C.8 |
| 1.1285 | B.133 | C.8 |
| 1.1286 | B.134 | C.8 |
| 1.1287 | B.135 | C.8 |
| 1.1288 | B.136 | C.8 |
| 1.1289 | B.137 | C.8 |
| 1.1290 | B.138 | C.8 |
| 1.1291 | B.139 | C.8 |
| 1.1292 | B.140 | C.8 |
| 1.1293 | B.141 | C.8 |
| 1.1294 | B.142 | C.8 |
| 1.1295 | B.143 | C.8 |
| 1.1296 | B.144 | C.8 |
| 1.1297 | B.1 | C.9 |
| 1.1298 | B.2 | C.9 |
| 1.1299 | B.3 | C.9 |
| 1.1300 | B.4 | C.9 |
| 1.1301 | B.5 | C.9 |
| 1.1302 | B.6 | C.9 |
| 1.1303 | B.7 | C.9 |
| 1.1304 | B.8 | C.9 |
| 1.1305 | B.9 | C.9 |
| 1.1306 | B.10 | C.9 |
| 1.1307 | B.11 | C.9 |
| 1.1308 | B.12 | C.9 |

TABLE 1-continued (compositions 1.1 to 1.2029):

| comp. no. | herbicide B | safener C |
|---|---|---|
| 1.1309 | B.13 | C.9 |
| 1.1310 | B.14 | C.9 |
| 1.1311 | B.15 | C.9 |
| 1.1312 | B.16 | C.9 |
| 1.1313 | B.17 | C.9 |
| 1.1314 | B.18 | C.9 |
| 1.1315 | B.19 | C.9 |
| 1.1316 | B.20 | C.9 |
| 1.1317 | B.21 | C.9 |
| 1.1318 | B.22 | C.9 |
| 1.1319 | B.23 | C.9 |
| 1.1320 | B.24 | C.9 |
| 1.1321 | B.25 | C.9 |
| 1.1322 | B.26 | C.9 |
| 1.1323 | B.27 | C.9 |
| 1.1324 | B.28 | C.9 |
| 1.1325 | B.29 | C.9 |
| 1.1326 | B.30 | C.9 |
| 1.1327 | B.31 | C.9 |
| 1.1328 | B.32 | C.9 |
| 1.1329 | B.33 | C.9 |
| 1.1330 | B.34 | C.9 |
| 1.1331 | B.35 | C.9 |
| 1.1332 | B.36 | C.9 |
| 1.1333 | B.37 | C.9 |
| 1.1334 | B.38 | C.9 |
| 1.1335 | B.39 | C.9 |
| 1.1336 | B.40 | C.9 |
| 1.1337 | B.41 | C.9 |
| 1.1338 | B.42 | C.9 |
| 1.1339 | B.43 | C.9 |
| 1.1340 | B.44 | C.9 |
| 1.1341 | B.45 | C.9 |
| 1.1342 | B.46 | C.9 |
| 1.1343 | B.47 | C.9 |
| 1.1344 | B.48 | C.9 |
| 1.1345 | B.49 | C.9 |
| 1.1346 | B.50 | C.9 |
| 1.1347 | B.51 | C.9 |
| 1.1348 | B.52 | C.9 |
| 1.1349 | B.53 | C.9 |
| 1.1350 | B.54 | C.9 |
| 1.1351 | B.55 | C.9 |
| 1.1352 | B.56 | C.9 |
| 1.1353 | B.57 | C.9 |
| 1.1354 | B.58. | C.9 |
| 1.1355 | B.59 | C.9 |
| 1.1356 | B.60 | C.9 |
| 1.1357 | B.61 | C.9 |
| 1.1358 | B.62 | C.9 |
| 1.1359 | B.63 | C.9 |
| 1.1360 | B.64 | C.9 |
| 1.1361 | B.65 | C.9 |
| 1.1362 | B.66 | C.9 |
| 1.1363 | B.67 | C.9 |
| 1.1364 | B.68 | C.9 |
| 1.1365 | B.69 | C.9 |
| 1.1366 | B.70 | C.9 |
| 1.1367 | B.71 | C.9 |
| 1.1368 | B.72 | C.9 |
| 1.1369 | B.73 | C.9 |
| 1.1370 | B.74 | C.9 |
| 1.1371 | B.75 | C.9 |
| 1.1372 | B.76 | C.9 |
| 1.1373 | B.77 | C.9 |
| 1.1374 | B.78 | C.9 |
| 1.1375 | B.79 | C.9 |
| 1.1376 | B.80 | C.9 |
| 1.1377 | B.81 | C.9 |
| 1.1378 | B.82 | C.9 |
| 1.1379 | B.83 | C.9 |
| 1.1380 | B.84 | C.9 |
| 1.1381 | B.85 | C.9 |
| 1.1382 | B.86 | C.9 |
| 1.1383 | B.87 | C.9 |
| 1.1384 | B.88 | C.9 |
| 1.1385 | B.89 | C.9 |
| 1.1386 | B.90 | C.9 |
| 1.1387 | B.91 | C.9 |
| 1.1388 | B.92 | C.9 |
| 1.1389 | B.93 | C.9 |
| 1.1390 | B.94 | C.9 |
| 1.1391 | B.95 | C.9 |
| 1.1392 | B.96 | C.9 |
| 1.1393 | B.97 | C.9 |
| 1.1394 | B.98 | C.9 |
| 1.1395 | B.99 | C.9 |
| 1.1396 | B.100 | C.9 |
| 1.1397 | B.101 | C.9 |
| 1.1398 | B.102 | C.9 |
| 1.1399 | B.103 | C.9 |
| 1.1400 | B.104 | C.9 |
| 1.1401 | B.105 | C.9 |
| 1.1402 | B.106 | C.9 |
| 1.1403 | B.107 | C.9 |
| 1.1404 | B.108 | C.9 |
| 1.1405 | B.109 | C.9 |
| 1.1406 | B.110 | C.9 |
| 1.1407 | B.111 | C.9 |
| 1.1408 | B.112 | C.9 |
| 1.1409 | B.113 | C.9 |
| 1.1410 | B.114 | C.9 |
| 1.1411 | B.115 | C.9 |
| 1.1412 | B.116 | C.9 |
| 1.1413 | B.117 | C.9 |
| 1.1414 | B.118 | C.9 |
| 1.1415 | B.119 | C.9 |
| 1.1416 | B.120 | C.9 |
| 1.1417 | B.121 | C.9 |
| 1.1418 | B.122 | C.9 |
| 1.1419 | B.123 | C.9 |
| 1.1420 | B.124 | C.9 |
| 1.1421 | B.125 | C.9 |
| 1.1422 | B.126 | C.9 |
| 1.1423 | B.127 | C.9 |
| 1.1424 | B.128 | C.9 |
| 1.1425 | B.129 | C.9 |
| 1.1426 | B.130 | C.9 |
| 1.1427 | B.131 | C.9 |
| 1.1428 | B.132 | C.9 |
| 1.1429 | B.133 | C.9 |
| 1.1430 | B.134 | C.9 |
| 1.1431 | B.135 | C.9 |
| 1.1432 | B.136 | C.9 |
| 1.1433 | B.137 | C.9 |
| 1.1434 | B.138 | C.9 |
| 1.1435 | B.139 | C.9 |
| 1.1436 | B.140 | C.9 |
| 1.1437 | B.141 | C.9 |
| 1.1438 | B.142 | C.9 |
| 1.1439 | B.143 | C.9 |
| 1.1440 | B.144 | C.9 |
| 1.1441 | B.1 | C.10 |
| 1.1442 | B.2 | C.10 |
| 1.1443 | B.3 | C.10 |
| 1.1444 | B.4 | C.10 |
| 1.1445 | B.5 | C.10 |
| 1.1446 | B.6 | C.10 |
| 1.1447 | B.7 | C.10 |
| 1.1448 | B.8 | C.10 |
| 1.1449 | B.9 | C.10 |
| 1.1450 | B.10 | C.10 |
| 1.1451 | B.11 | C.10 |
| 1.1452 | B.12 | C.10 |
| 1.1453 | B.13 | C.10 |
| 1.1454 | B.14 | C.10 |
| 1.1455 | B.15 | C.10 |
| 1.1456 | B.16 | C.10 |
| 1.1457 | B.17 | C.10 |
| 1.1458 | B.18 | C.10 |
| 1.1459 | B.19 | C.10 |
| 1.1460 | B.20 | C.10 |

TABLE 1-continued (compositions 1.1 to 1.2029):

| comp. no. | herbicide B | safener C |
|---|---|---|
| 1.1461 | B.21 | C.10 |
| 1.1462 | B.22 | C.10 |
| 1.1463 | B.23 | C.10 |
| 1.1464 | B.24 | C.10 |
| 1.1465 | B.25 | C.10 |
| 1.1466 | B.26 | C.10 |
| 1.1467 | B.27 | C.10 |
| 1.1468 | B.28 | C.10 |
| 1.1469 | B.29 | C.10 |
| 1.1470 | B.30 | C.10 |
| 1.1471 | B.31 | C.10 |
| 1.1472 | B.32 | C.10 |
| 1.1473 | B.33 | C.10 |
| 1.1474 | B.34 | C.10 |
| 1.1475 | B.35 | C.10 |
| 1.1476 | B.36 | C.10 |
| 1.1477 | B.37 | C.10 |
| 1.1478 | B.38 | C.10 |
| 1.1479 | B.39 | C.10 |
| 1.1480 | B.40 | C.10 |
| 1.1481 | B.41 | C.10 |
| 1.1482 | B.42 | C.10 |
| 1.1483 | B.43 | C.10 |
| 1.1484 | B.44 | C.10 |
| 1.1485 | B.45 | C.10 |
| 1.1486 | B.46 | C.10 |
| 1.1487 | B.47 | C.10 |
| 1.1488 | B.48 | C.10 |
| 1.1489 | B.49 | C.10 |
| 1.1490 | B.50 | C.10 |
| 1.1491 | B.51 | C.10 |
| 1.1492 | B.52 | C.10 |
| 1.1493 | B.53 | C.10 |
| 1.1494 | B.54 | C.10 |
| 1.1495 | B.55 | C.10 |
| 1.1496 | B.56 | C.10 |
| 1.1497 | B.57 | C.10 |
| 1.1498 | B.58. | C.10 |
| 1.1499 | B.59 | C.10 |
| 1.1500 | B.60 | C.10 |
| 1.1501 | B.61 | C.10 |
| 1.1502 | B.62 | C.10 |
| 1.1503 | B.63 | C.10 |
| 1.1504 | B.64 | C.10 |
| 1.1505 | B.65 | C.10 |
| 1.1506 | B.66 | C.10 |
| 1.1507 | B.67 | C.10 |
| 1.1508 | B.68 | C.10 |
| 1.1509 | B.69 | C.10 |
| 1.1510 | B.70 | C.10 |
| 1.1511 | B.71 | C.10 |
| 1.1512 | B.72 | C.10 |
| 1.1513 | B.73 | C.10 |
| 1.1514 | B.74 | C.10 |
| 1.1515 | B.75 | C.10 |
| 1.1516 | B.76 | C.10 |
| 1.1517 | B.77 | C.10 |
| 1.1518 | B.78 | C.10 |
| 1.1519 | B.79 | C.10 |
| 1.1520 | B.80 | C.10 |
| 1.1521 | B.81 | C.10 |
| 1.1522 | B.82 | C.10 |
| 1.1523 | B.83 | C.10 |
| 1.1524 | B.84 | C.10 |
| 1.1525 | B.85 | C.10 |
| 1.1526 | B.86 | C.10 |
| 1.1527 | B.87 | C.10 |
| 1.1528 | B.88 | C.10 |
| 1.1529 | B.89 | C.10 |
| 1.1530 | B.90 | C.10 |
| 1.1531 | B.91 | C.10 |
| 1.1532 | B.92 | C.10 |
| 1.1533 | B.93 | C.10 |
| 1.1534 | B.94 | C.10 |
| 1.1535 | B.95 | C.10 |
| 1.1536 | B.96 | C.10 |
| 1.1537 | B.97 | C.10 |
| 1.1538 | B.98 | C.10 |
| 1.1539 | B.99 | C.10 |
| 1.1540 | B.100 | C.10 |
| 1.1541 | B.101 | C.10 |
| 1.1542 | B.102 | C.10 |
| 1.1543 | B.103 | C.10 |
| 1.1544 | B.104 | C.10 |
| 1.1545 | B.105 | C.10 |
| 1.1546 | B.106 | C.10 |
| 1.1547 | B.107 | C.10 |
| 1.1548 | B.108 | C.10 |
| 1.1549 | B.109 | C.10 |
| 1.1550 | B.110 | C.10 |
| 1.1551 | B.111 | C.10 |
| 1.1552 | B.112 | C.10 |
| 1.1553 | B.113 | C.10 |
| 1.1554 | B.114 | C.10 |
| 1.1555 | B.115 | C.10 |
| 1.1556 | B.116 | C.10 |
| 1.1557 | B.117 | C.10 |
| 1.1558 | B.118 | C.10 |
| 1.1559 | B.119 | C.10 |
| 1.1560 | B.120 | C.10 |
| 1.1561 | B.121 | C.10 |
| 1.1562 | B.122 | C.10 |
| 1.1563 | B.123 | C.10 |
| 1.1564 | B.124 | C.10 |
| 1.1565 | B.125 | C.10 |
| 1.1566 | B.126 | C.10 |
| 1.1567 | B.127 | C.10 |
| 1.1568 | B.128 | C.10 |
| 1.1569 | B.129 | C.10 |
| 1.1570 | B.130 | C.10 |
| 1.1571 | B.131 | C.10 |
| 1.1572 | B.132 | C.10 |
| 1.1573 | B.133 | C.10 |
| 1.1574 | B.134 | C.10 |
| 1.1575 | B.135 | C.10 |
| 1.1576 | B.136 | C.10 |
| 1.1577 | B.137 | C.10 |
| 1.1578 | B.138 | C.10 |
| 1.1579 | B.139 | C.10 |
| 1.1580 | B.140 | C.10 |
| 1.1581 | B.141 | C.10 |
| 1.1582 | B.142 | C.10 |
| 1.1583 | B.143 | C.10 |
| 1.1584 | B.144 | C.10 |
| 1.1585 | B.1 | C.11 |
| 1.1586 | B.2 | C.11 |
| 1.1587 | B.3 | C.11 |
| 1.1588 | B.4 | C.11 |
| 1.1589 | B.5 | C.11 |
| 1.1590 | B.6 | C.11 |
| 1.1591 | B.7 | C.11 |
| 1.1592 | B.8 | C.11 |
| 1.1593 | B.9 | C.11 |
| 1.1594 | B.10 | C.11 |
| 1.1595 | B.11 | C.11 |
| 1.1596 | B.12 | C.11 |
| 1.1597 | B.13 | C.11 |
| 1.1598 | B.14 | C.11 |
| 1.1599 | B.15 | C.11 |
| 1.1600 | B.16 | C.11 |
| 1.1601 | B.17 | C.11 |
| 1.1602 | B.18 | C.11 |
| 1.1603 | B.19 | C.11 |
| 1.1604 | B.20 | C.11 |
| 1.1605 | B.21 | C.11 |
| 1.1606 | B.22 | C.11 |
| 1.1607 | B.23 | C.11 |
| 1.1608 | B.24 | C.11 |
| 1.1609 | B.25 | C.11 |
| 1.1610 | B.26 | C.11 |
| 1.1611 | B.27 | C.11 |
| 1.1612 | B.28 | C.11 |

TABLE 1-continued (compositions 1.1 to 1.2029):

| comp. no. | herbicide B | safener C |
|---|---|---|
| 1.1613 | B.29 | C.11 |
| 1.1614 | B.30 | C.11 |
| 1.1615 | B.31 | C.11 |
| 1.1616 | B.32 | C.11 |
| 1.1617 | B.33 | C.11 |
| 1.1618 | B.34 | C.11 |
| 1.1619 | B.35 | C.11 |
| 1.1620 | B.36 | C.11 |
| 1.1621 | B.37 | C.11 |
| 1.1622 | B.38 | C.11 |
| 1.1623 | B.39 | C.11 |
| 1.1624 | B.40 | C.11 |
| 1.1625 | B.41 | C.11 |
| 1.1626 | B.42 | C.11 |
| 1.1627 | B.43 | C.11 |
| 1.1628 | B.44 | C.11 |
| 1.1629 | B.45 | C.11 |
| 1.1630 | B.46 | C.11 |
| 1.1631 | B.47 | C.11 |
| 1.1632 | B.48 | C.11 |
| 1.1633 | B.49 | C.11 |
| 1.1634 | B.50 | C.11 |
| 1.1635 | B.51 | C.11 |
| 1.1636 | B.52 | C.11 |
| 1.1637 | B.53 | C.11 |
| 1.1638 | B.54 | C.11 |
| 1.1639 | B.55 | C.11 |
| 1.1640 | B.56 | C.11 |
| 1.1641 | B.57 | C.11 |
| 1.1642 | B.58. | C.11 |
| 1.1643 | B.59 | C.11 |
| 1.1644 | B.60 | C.11 |
| 1.1645 | B.61 | C.11 |
| 1.1646 | B.62 | C.11 |
| 1.1647 | B.63 | C.11 |
| 1.1648 | B.64 | C.11 |
| 1.1649 | B.65 | C.11 |
| 1.1650 | B.66 | C.11 |
| 1.1651 | B.67 | C.11 |
| 1.1652 | B.68 | C.11 |
| 1.1653 | B.69 | C.11 |
| 1.1654 | B.70 | C.11 |
| 1.1655 | B.71 | C.11 |
| 1.1656 | B.72 | C.11 |
| 1.1657 | B.73 | C.11 |
| 1.1658 | B.74 | C.11 |
| 1.1659 | B.75 | C.11 |
| 1.1660 | B.76 | C.11 |
| 1.1661 | B.77 | C.11 |
| 1.1662 | B.78 | C.11 |
| 1.1663 | B.79 | C.11 |
| 1.1664 | B.80 | C.11 |
| 1.1665 | B.81 | C.11 |
| 1.1666 | B.82 | C.11 |
| 1.1667 | B.83 | C.11 |
| 1.1668 | B.84 | C.11 |
| 1.1669 | B.85 | C.11 |
| 1.1670 | B.86 | C.11 |
| 1.1671 | B.87 | C.11 |
| 1.1672 | B.88 | C.11 |
| 1.1673 | B.89 | C.11 |
| 1.1674 | B.90 | C.11 |
| 1.1675 | B.91 | C.11 |
| 1.1676 | B.92 | C.11 |
| 1.1677 | B.93 | C.11 |
| 1.1678 | B.94 | C.11 |
| 1.1679 | B.95 | C.11 |
| 1.1680 | B.96 | C.11 |
| 1.1681 | B.97 | C.11 |
| 1.1682 | B.98 | C.11 |
| 1.1683 | B.99 | C.11 |
| 1.1684 | B.100 | C.11 |
| 1.1685 | B.101 | C.11 |
| 1.1686 | B.102 | C.11 |
| 1.1687 | B.103 | C.11 |
| 1.1688 | B.104 | C.11 |
| 1.1689 | B.105 | C.11 |
| 1.1690 | B.106 | C.11 |
| 1.1691 | B.107 | C.11 |
| 1.1692 | B.108 | C.11 |
| 1.1693 | B.109 | C.11 |
| 1.1694 | B.110 | C.11 |
| 1.1695 | B.111 | C.11 |
| 1.1696 | B.112 | C.11 |
| 1.1697 | B.113 | C.11 |
| 1.1698 | B.114 | C.11 |
| 1.1699 | B.115 | C.11 |
| 1.1700 | B.116 | C.11 |
| 1.1701 | B.117 | C.11 |
| 1.1702 | B.118 | C.11 |
| 1.1703 | B.119 | C.11 |
| 1.1704 | B.120 | C.11 |
| 1.1705 | B.121 | C.11 |
| 1.1706 | B.122 | C.11 |
| 1.1707 | B.123 | C.11 |
| 1.1708 | B.124 | C.11 |
| 1.1709 | B.125 | C.11 |
| 1.1710 | B.126 | C.11 |
| 1.1711 | B.127 | C.11 |
| 1.1712 | B.128 | C.11 |
| 1.1713 | B.129 | C.11 |
| 1.1714 | B.130 | C.11 |
| 1.1715 | B.131 | C.11 |
| 1.1716 | B.132 | C.11 |
| 1.1717 | B.133 | C.11 |
| 1.1718 | B.134 | C.11 |
| 1.1719 | B.135 | C.11 |
| 1.1720 | B.136 | C.11 |
| 1.1721 | B.137 | C.11 |
| 1.1722 | B.138 | C.11 |
| 1.1723 | B.139 | C.11 |
| 1.1724 | B.140 | C.11 |
| 1.1725 | B.141 | C.11 |
| 1.1726 | B.142 | C.11 |
| 1.1727 | B.143 | C.11 |
| 1.1728 | B.144 | C.11 |
| 1.1729 | B.1 | C.12 |
| 1.1730 | B.2 | C.12 |
| 1.1731 | B.3 | C.12 |
| 1.1732 | B.4 | C.12 |
| 1.1733 | B.5 | C.12 |
| 1.1734 | B.6 | C.12 |
| 1.1735 | B.7 | C.12 |
| 1.1736 | B.8 | C.12 |
| 1.1737 | B.9 | C.12 |
| 1.1738 | B.10 | C.12 |
| 1.1739 | B.11 | C.12 |
| 1.1740 | B.12 | C.12 |
| 1.1741 | B.13 | C.12 |
| 1.1742 | B.14 | C.12 |
| 1.1743 | B.15 | C.12 |
| 1.1744 | B.16 | C.12 |
| 1.1745 | B.17 | C.12 |
| 1.1746 | B.18 | C.12 |
| 1.1747 | B.19 | C.12 |
| 1.1748 | B.20 | C.12 |
| 1.1749 | B.21 | C.12 |
| 1.1750 | B.22 | C.12 |
| 1.1751 | B.23 | C.12 |
| 1.1752 | B.24 | C.12 |
| 1.1753 | B.25 | C.12 |
| 1.1754 | B.26 | C.12 |
| 1.1755 | B.27 | C.12 |
| 1.1756 | B.28 | C.12 |
| 1.1757 | B.29 | C.12 |
| 1.1758 | B.30 | C.12 |
| 1.1759 | B.31 | C.12 |
| 1.1760 | B.32 | C.12 |
| 1.1761 | B.33 | C.12 |
| 1.1762 | B.34 | C.12 |
| 1.1763 | B.35 | C.12 |
| 1.1764 | B.36 | C.12 |

TABLE 1-continued (compositions 1.1 to 1.2029):

| comp. no. | herbicide B | safener C |
|---|---|---|
| 1.1765 | B.37 | C.12 |
| 1.1766 | B.38 | C.12 |
| 1.1767 | B.39 | C.12 |
| 1.1768 | B.40 | C.12 |
| 1.1769 | B.41 | C.12 |
| 1.1770 | B.42 | C.12 |
| 1.1771 | B.43 | C.12 |
| 1.1772 | B.44 | C.12 |
| 1.1773 | B.45 | C.12 |
| 1.1774 | B.46 | C.12 |
| 1.1775 | B.47 | C.12 |
| 1.1776 | B.48 | C.12 |
| 1.1777 | B.49 | C.12 |
| 1.1778 | B.50 | C.12 |
| 1.1779 | B.51 | C.12 |
| 1.1780 | B.52 | C.12 |
| 1.1781 | B.53 | C.12 |
| 1.1782 | B.54 | C.12 |
| 1.1783 | B.55 | C.12 |
| 1.1784 | B.56 | C.12 |
| 1.1785 | B.57 | C.12 |
| 1.1786 | B.58. | C.12 |
| 1.1787 | B.59 | C.12 |
| 1.1788 | B.60 | C.12 |
| 1.1789 | B.61 | C.12 |
| 1.1790 | B.62 | C.12 |
| 1.1791 | B.63 | C.12 |
| 1.1792 | B.64 | C.12 |
| 1.1793 | B.65 | C.12 |
| 1.1794 | B.66 | C.12 |
| 1.1795 | B.67 | C.12 |
| 1.1796 | B.68 | C.12 |
| 1.1797 | B.69 | C.12 |
| 1.1798 | B.70 | C.12 |
| 1.1799 | B.71 | C.12 |
| 1.1800 | B.72 | C.12 |
| 1.1801 | B.73 | C.12 |
| 1.1802 | B.74 | C.12 |
| 1.1803 | B.75 | C.12 |
| 1.1804 | B.76 | C.12 |
| 1.1805 | B.77 | C.12 |
| 1.1806 | B.78 | C.12 |
| 1.1807 | B.79 | C.12 |
| 1.1808 | B.80 | C.12 |
| 1.1809 | B.81 | C.12 |
| 1.1810 | B.82 | C.12 |
| 1.1811 | B.83 | C.12 |
| 1.1812 | B.84 | C.12 |
| 1.1813 | B.85 | C.12 |
| 1.1814 | B.86 | C.12 |
| 1.1815 | B.87 | C.12 |
| 1.1816 | B.88 | C.12 |
| 1.1817 | B.89 | C.12 |
| 1.1818 | B.90 | C.12 |
| 1.1819 | B.91 | C.12 |
| 1.1820 | B.92 | C.12 |
| 1.1821 | B.93 | C.12 |
| 1.1822 | B.94 | C.12 |
| 1.1823 | B.95 | C.12 |
| 1.1824 | B.96 | C.12 |
| 1.1825 | B.97 | C.12 |
| 1.1826 | B.98 | C.12 |
| 1.1827 | B.99 | C.12 |
| 1.1828 | B.100 | C.12 |
| 1.1829 | B.101 | C.12 |
| 1.1830 | B.102 | C.12 |
| 1.1831 | B.103 | C.12 |
| 1.1832 | B.104 | C.12 |
| 1.1833 | B.105 | C.12 |
| 1.1834 | B.106 | C.12 |
| 1.1835 | B.107 | C.12 |
| 1.1836 | B.108 | C.12 |
| 1.1837 | B.109 | C.12 |
| 1.1838 | B.110 | C.12 |
| 1.1839 | B.111 | C.12 |
| 1.1840 | B.112 | C.12 |
| 1.1841 | B.113 | C.12 |
| 1.1842 | B.114 | C.12 |
| 1.1843 | B.115 | C.12 |
| 1.1844 | B.116 | C.12 |
| 1.1845 | B.117 | C.12 |
| 1.1846 | B.118 | C.12 |
| 1.1847 | B.119 | C.12 |
| 1.1848 | B.120 | C.12 |
| 1.1849 | B.121 | C.12 |
| 1.1850 | B.122 | C.12 |
| 1.1851 | B.123 | C.12 |
| 1.1852 | B.124 | C.12 |
| 1.1853 | B.125 | C.12 |
| 1.1854 | B.126 | C.12 |
| 1.1855 | B.127 | C.12 |
| 1.1856 | B.128 | C.12 |
| 1.1857 | B.129 | C.12 |
| 1.1858 | B.130 | C.12 |
| 1.1859 | B.131 | C.12 |
| 1.1860 | B.132 | C.12 |
| 1.1861 | B.133 | C.12 |
| 1.1862 | B.134 | C.12 |
| 1.1863 | B.135 | C.12 |
| 1.1864 | B.136 | C.12 |
| 1.1865 | B.137 | C.12 |
| 1.1866 | B.138 | C.12 |
| 1.1867 | B.139 | C.12 |
| 1.1868 | B.140 | C.12 |
| 1.1869 | B.141 | C.12 |
| 1.1870 | B.142 | C.12 |
| 1.1871 | B.143 | C.12 |
| 1.1872 | B.144 | C.12 |
| 1.1873 | B.1 | C.13 |
| 1.1874 | B.2 | C.13 |
| 1.1875 | B.3 | C.13 |
| 1.1876 | B.4 | C.13 |
| 1.1877 | B.5 | C.13 |
| 1.1878 | B.6 | C.13 |
| 1.1879 | B.7 | C.13 |
| 1.1880 | B.8 | C.13 |
| 1.1881 | B.9 | C.13 |
| 1.1882 | B.10 | C.13 |
| 1.1883 | B.11 | C.13 |
| 1.1884 | B.12 | C.13 |
| 1.1885 | B.13 | C.13 |
| 1.1886 | B.14 | C.13 |
| 1.1887 | B.15 | C.13 |
| 1.1888 | B.16 | C.13 |
| 1.1889 | B.17 | C.13 |
| 1.1890 | B.18 | C.13 |
| 1.1891 | B.19 | C.13 |
| 1.1892 | B.20 | C.13 |
| 1.1893 | B.21 | C.13 |
| 1.1894 | B.22 | C.13 |
| 1.1895 | B.23 | C.13 |
| 1.1896 | B.24 | C.13 |
| 1.1897 | B.25 | C.13 |
| 1.1898 | B.26 | C.13 |
| 1.1899 | B.27 | C.13 |
| 1.1900 | B.28 | C.13 |
| 1.1901 | B.29 | C.13 |
| 1.1902 | B.30 | C.13 |
| 1.1903 | B.31 | C.13 |
| 1.1904 | B.32 | C.13 |
| 1.1905 | B.33 | C.13 |
| 1.1906 | B.34 | C.13 |
| 1.1907 | B.35 | C.13 |
| 1.1908 | B.36 | C.13 |
| 1.1909 | B.37 | C.13 |
| 1.1910 | B.38 | C.13 |
| 1.1911 | B.39 | C.13 |
| 1.1912 | B.40 | C.13 |
| 1.1913 | B.41 | C.13 |
| 1.1914 | B.42 | C.13 |
| 1.1915 | B.43 | C.13 |
| 1.1916 | B.44 | C.13 |

TABLE 1-continued (compositions 1.1 to 1.2029):

| comp. no. | herbicide B | safener C |
|---|---|---|
| 1.1917 | B.45 | C.13 |
| 1.1918 | B.46 | C.13 |
| 1.1919 | B.47 | C.13 |
| 1.1920 | B.48 | C.13 |
| 1.1921 | B.49 | C.13 |
| 1.1922 | B.50 | C.13 |
| 1.1923 | B.51 | C.13 |
| 1.1924 | B.52 | C.13 |
| 1.1925 | B.53 | C.13 |
| 1.1926 | B.54 | C.13 |
| 1.1927 | B.55 | C.13 |
| 1.1928 | B.56 | C.13 |
| 1.1929 | B.57 | C.13 |
| 1.1930 | B.58. | C.13 |
| 1.1931 | B.59 | C.13 |
| 1.1932 | B.60 | C.13 |
| 1.1933 | B.61 | C.13 |
| 1.1934 | B.62 | C.13 |
| 1.1935 | B.63 | C.13 |
| 1.1936 | B.64 | C.13 |
| 1.1937 | B.65 | C.13 |
| 1.1938 | B.66 | C.13 |
| 1.1939 | B.67 | C.13 |
| 1.1940 | B.68 | C.13 |
| 1.1941 | B.69 | C.13 |
| 1.1942 | B.70 | C.13 |
| 1.1943 | B.71 | C.13 |
| 1.1944 | B.72 | C.13 |
| 1.1945 | B.73 | C.13 |
| 1.1946 | B.74 | C.13 |
| 1.1947 | B.75 | C.13 |
| 1.1948 | B.76 | C.13 |
| 1.1949 | B.77 | C.13 |
| 1.1950 | B.78 | C.13 |
| 1.1951 | B.79 | C.13 |
| 1.1952 | B.80 | C.13 |
| 1.1953 | B.81 | C.13 |
| 1.1954 | B.82 | C.13 |
| 1.1955 | B.83 | C.13 |
| 1.1956 | B.84 | C.13 |
| 1.1957 | B.85 | C.13 |
| 1.1958 | B.86 | C.13 |
| 1.1959 | B.87 | C.13 |
| 1.1960 | B.88 | C.13 |
| 1.1961 | B.89 | C.13 |
| 1.1962 | B.90 | C.13 |
| 1.1963 | B.91 | C.13 |
| 1.1964 | B.92 | C.13 |
| 1.1965 | B.93 | C.13 |
| 1.1966 | B.94 | C.13 |
| 1.1967 | B.95 | C.13 |
| 1.1968 | B.96 | C.13 |
| 1.1969 | B.97 | C.13 |
| 1.1970 | B.98 | C.13 |
| 1.1971 | B.99 | C.13 |
| 1.1972 | B.100 | C.13 |
| 1.1973 | B.101 | C.13 |
| 1.1974 | B.102 | C.13 |
| 1.1975 | B.103 | C.13 |
| 1.1976 | B.104 | C.13 |
| 1.1977 | B.105 | C.13 |
| 1.1978 | B.106 | C.13 |
| 1.1979 | B.107 | C.13 |
| 1.1980 | B.108 | C.13 |
| 1.1981 | B.109 | C.13 |
| 1.1982 | B.110 | C.13 |
| 1.1983 | B.111 | C.13 |
| 1.1984 | B.112 | C.13 |
| 1.1985 | B.113 | C.13 |
| 1.1986 | B.114 | C.13 |
| 1.1987 | B.115 | C.13 |
| 1.1988 | B.116 | C.13 |
| 1.1989 | B.117 | C.13 |
| 1.1990 | B.118 | C.13 |
| 1.1991 | B.119 | C.13 |
| 1.1992 | B.120 | C.13 |
| 1.1993 | B.121 | C.13 |
| 1.1994 | B.122 | C.13 |
| 1.1995 | B.123 | C.13 |
| 1.1996 | B.124 | C.13 |
| 1.1997 | B.125 | C.13 |
| 1.1998 | B.126 | C.13 |
| 1.1999 | B.127 | C.13 |
| 1.2000 | B.128 | C.13 |
| 1.2001 | B.129 | C.13 |
| 1.2002 | B.130 | C.13 |
| 1.2003 | B.131 | C.13 |
| 1.2004 | B.132 | C.13 |
| 1.2005 | B.133 | C.13 |
| 1.2006 | B.134 | C.13 |
| 1.2007 | B.135 | C.13 |
| 1.2008 | B.136 | C.13 |
| 1.2009 | B.137 | C.13 |
| 1.2010 | B.138 | C.13 |
| 1.2011 | B.139 | C.13 |
| 1.2012 | B.140 | C.13 |
| 1.2013 | B.141 | C.13 |
| 1.2014 | B.142 | C.13 |
| 1.2015 | B.143 | C.13 |
| 1.2016 | B.144 | C.13 |
| 1.2017 | — | C.1 |
| 1.2018 | — | C.2 |
| 1.2019 | — | C.3 |
| 1.2020 | — | C.4 |
| 1.2021 | — | C.5 |
| 1.2022 | — | C.6 |
| 1.2023 | — | C.7 |
| 1.2024 | — | C.8 |
| 1.2025 | — | C.9 |
| 1.2026 | — | C.10 |
| 1.2027 | — | C.11 |
| 1.2028 | — | C.12 |
| 1.2029 | — | C.13 |

The specific number for each single composition is deductible as follows:

Composition 1.777 for example comprises the benzoxazinone Ia48, diuron (B.57) and fenchlorazole (C.5) (see table 1, entry 1.777; as well as table B, entry B.57 and table C, entry C.5).

Composition 2.777 for example comprises the benzoxazinone Im48 (see the definition for compositions 2.1 to 2.2029 below), diuron (B.57) and fenchlorazole (C.5) (see table 1, entry 1.777; as well as table B, entry B.57 and table C, entry C.5).

Also especially preferred are compositions 2.1. to 2.2029 which differ from the corresponding compositions 1.1 to 1.2029 only in that they comprise as the active compound A the compound Im48.

Also especially preferred are compositions 3.1. to 3.2029 which differ from the corresponding compositions 1.1 to 1.2029 only in that they comprise as the active compound A the compound In48.

Also especially preferred are compositions 4.1. to 4.2029 which differ from the corresponding compositions 1.1 to 1.2029 only in that they comprise as the active compound A the compound Io48.

Also especially preferred are compositions 5.1. to 5.2029 which differ from the corresponding compositions 1.1 to 1.2029 only in that they comprise as the active compound A the compound Ip48.

Also especially preferred are compositions 6.1. to 6.2029 which differ from the corresponding compositions 1.1 to 1.2029 only in that they comprise as the active compound A the compound Iq48.

Also especially preferred are compositions 7.1. to 7.2029 which differ from the corresponding compositions 1.1 to 1.2029 only in that they additionally comprise B.31 as further herbicide B.

Also especially preferred are compositions 8.1. to 8.2029 which differ from the corresponding compositions 1.1 to 1.2029 only in that they additionally comprise B.32 as further herbicide B.

Also especially preferred are compositions 9.1. to 9.2029 which differ from the corresponding compositions 1.1 to 1.2029 only in that they additionally comprise B.33 as further herbicide B.

Also especially preferred are compositions 10.1. to 10.2029 which differ from the corresponding compositions 1.1 to 1.2029 only in that they additionally comprise B.40 as further herbicide B.

Also especially preferred are compositions 11.1. to 11.2029 which differ from the corresponding compositions 1.1 to 1.2029 only in that they additionally comprise B.44 as further herbicide B.

Also especially preferred are compositions 12.1. to 12.2029 which differ from the corresponding compositions 1.1 to 1.2029 only in that they additionally comprise B.45 as further herbicide B.

Also especially preferred are compositions 13.1. to 13.2029 which differ from the corresponding compositions 1.1 to 1.2029 only in that they additionally comprise B.52 as further herbicide B.

Also especially preferred are compositions 14.1. to 14.2029 which differ from the corresponding compositions 1.1 to 1.2029 only in that they additionally comprise B.53 as further herbicide B.

Also especially preferred are compositions 15.1. to 15.2029 which differ from the corresponding compositions 1.1 to 1.2029 only in that they additionally comprise B.54 as further herbicide B.

Also especially preferred are compositions 16.1. to 16.2029 which differ from the corresponding compositions 1.1 to 1.2029 only in that they additionally comprise B.55 as further herbicide B.

Also especially preferred are compositions 17.1. to 17.2029 which differ from the corresponding compositions 1.1 to 1.2029 only in that they additionally comprise B.56 as further herbicide B.

Also especially preferred are compositions 18.1. to 18.2029 which differ from the corresponding compositions 1.1 to 1.2029 only in that they additionally comprise B.57 as further herbicide B.

Also especially preferred are compositions 19.1. to 19.2029 which differ from the corresponding compositions 1.1 to 1.2029 only in that they additionally comprise B.60 as further herbicide B.

Also especially preferred are compositions 20.1. to 20.2029 which differ from the corresponding compositions 1.1 to 1.2029 only in that they additionally comprise B.65 as further herbicide B.

Also especially preferred are compositions 21.1. to 21.2029 which differ from the corresponding compositions 1.1 to 1.2029 only in that they additionally comprise B.66 as further herbicide B.

Also especially preferred are compositions 22.1. to 22.2029 which differ from the corresponding compositions 1.1 to 1.2029 only in that they additionally comprise B.69 as further herbicide B.

Also especially preferred are compositions 23.1. to 23.2029 which differ from the corresponding compositions 1.1 to 1.2029 only in that they additionally comprise B.72 as further herbicide B.

Also especially preferred are compositions 24.1. to 24.2029 which differ from the corresponding compositions 1.1 to 1.2029 only in that they additionally comprise B.73 as further herbicide B.

Also especially preferred are compositions 25.1. to 25.2029 which differ from the corresponding compositions 1.1 to 1.2029 only in that they additionally comprise B.76 as further herbicide B.

Also especially preferred are compositions 26.1. to 26.2029 which differ from the corresponding compositions 1.1 to 1.2029 only in that they additionally comprise B.77 as further herbicide B.

Also especially preferred are compositions 27.1. to 27.2029 which differ from the corresponding compositions 1.1 to 1.2029 only in that they additionally comprise B.83 as further herbicide B.

Also especially preferred are compositions 28.1. to 28.2029 which differ from the corresponding compositions 1.1 to 1.2029 only in that they additionally comprise B.84 as further herbicide B.

Also especially preferred are compositions 29.1. to 29.2029 which differ from the corresponding compositions 1.1 to 1.2029 only in that they additionally comprise B.87 as further herbicide B.

Also especially preferred are compositions 30.1. to 30.2029 which differ from the corresponding compositions 1.1 to 1.2029 only in that they additionally comprise B.87 and B.54 as further herbicides B.

Also especially preferred are compositions 31.1. to 31.2029 which differ from the corresponding compositions 1.1 to 1.2029 only in that they additionally comprise B.87 and B.60 as further herbicides B.

Also especially preferred are compositions 32.1. to 32.2029 which differ from the corresponding compositions 1.1 to 1.2029 only in that they additionally comprise B.87 and B.66 as further herbicides B.

Also especially preferred are compositions 33.1. to 33.2029 which differ from the corresponding compositions 1.1 to 1.2029 only in that they additionally comprise B.88 as further herbicide B.

Also especially preferred are compositions 34.1. to 34.2029 which differ from the corresponding compositions 1.1 to 1.2029 only in that they additionally comprise B.88 and B.54 as further herbicides B.

Also especially preferred are compositions 35.1. to 35.2029 which differ from the corresponding compositions 1.1 to 1.2029 only in that they additionally comprise B.88 and B.60 as further herbicides B.

Also especially preferred are compositions 36.1. to 36.2029 which differ from the corresponding compositions 1.1 to 1.2029 only in that they additionally comprise B.88 and B.66 as further herbicides B.

Also especially preferred are compositions 37.1. to 37.2029 which differ from the corresponding compositions 1.1 to 1.2029 only in that they additionally comprise B.90 as further herbicide B.

Also especially preferred are compositions 38.1. to 38.2029 which differ from the corresponding compositions 1.1 to 1.2029 only in that they additionally comprise B.91 as further herbicide B.

Also especially preferred are compositions 39.1. to 39.2029 which differ from the corresponding compositions 1.1 to 1.2029 only in that they additionally comprise B.91 and B.54 as further herbicides B.

Also especially preferred are compositions 40.1. to 40.2029 which differ from the corresponding compositions 1.1 to 1.2029 only in that they additionally comprise B.91 and B.60 as further herbicides B.

Also especially preferred are compositions 41.1. to 41.2029 which differ from the corresponding compositions 1.1 to 1.2029 only in that they additionally comprise B.91 and B.66 as further herbicides B.

Also especially preferred are compositions 42.1. to 42.2029 which differ from the corresponding compositions 1.1 to 1.2029 only in that they additionally comprise B.93 as further herbicide B.

Also especially preferred are compositions 43.1. to 43.2029 which differ from the corresponding compositions 1.1 to 1.2029 only in that they additionally comprise B.94 as further herbicide B.

Also especially preferred are compositions 44.1. to 44.2029 which differ from the corresponding compositions 1.1 to 1.2029 only in that they additionally comprise B.94 and B.54 as further herbicides B.

Also especially preferred are compositions 45.1. to 45.2029 which differ from the corresponding compositions 1.1 to 1.2029 only in that they additionally comprise B.94 and B.60 as further herbicides B.

Also especially preferred are compositions 46.1. to 46.2029 which differ from the corresponding compositions 1.1 to 1.2029 only in that they additionally comprise B.94 and B.66 as further herbicides B.

Also especially preferred are compositions 47.1. to 47.2029 which differ from the corresponding compositions 1.1 to 1.2029 only in that they additionally comprise B.98 as further herbicide B.

Also especially preferred are compositions 48.1. to 48.2029 which differ from the corresponding compositions 1.1 to 1.2029 only in that they additionally comprise B.98 and B.54 as further herbicides B.

Also especially preferred are compositions 49.1. to 49.2029 which differ from the corresponding compositions 1.1 to 1.2029 only in that they additionally comprise B.98 and B.76 as further herbicides B.

Also especially preferred are compositions 50.1. to 50.2029 which differ from the corresponding compositions 1.1 to 1.2029 only in that they additionally comprise B.98 and B.87 as further herbicides B.

Also especially preferred are compositions 51.1. to 51.2029 which differ from the corresponding compositions 1.1 to 1.2029 only in that they additionally comprise B.98 and B.106 as further herbicides B.

Also especially preferred are compositions 52.1. to 52.2029 which differ from the corresponding compositions 1.1 to 1.2029 only in that they additionally comprise B.98 and B.88 as further herbicides B.

Also especially preferred are compositions 53.1. to 53.2029 which differ from the corresponding compositions 1.1 to 1.2029 only in that they additionally comprise B.98 and B.91 as further herbicides B.

Also especially preferred are compositions 54.1. to 54.2029 which differ from the corresponding compositions 1.1 to 1.2029 only in that they additionally comprise B.98 and B.94 as further herbicides B.

Also especially preferred are compositions 55.1. to 55.2029 which differ from the corresponding compositions 1.1 to 1.2029 only in that they additionally comprise B.101 as further herbicide B.

Also especially preferred are compositions 56.1. to 56.2029 which differ from the corresponding compositions 1.1 to 1.2029 only in that they additionally comprise B.104 as further herbicide B.

Also especially preferred are compositions 57.1. to 57.2029 which differ from the corresponding compositions 1.1 to 1.2029 only in that they additionally comprise B.106 as further herbicide B.

Also especially preferred are compositions 58.1. to 58.2029 which differ from the corresponding compositions 1.1 to 1.2029 only in that they additionally comprise B.109 as further herbicide B.

Also especially preferred are compositions 59.1. to 59.2029 which differ from the corresponding compositions 1.1 to 1.2029 only in that they additionally comprise B.110 as further herbicide B.

Also especially preferred are compositions 60.1. to 60.2029 which differ from the corresponding compositions 1.1 to 1.2029 only in that they additionally comprise B.111 as further herbicide B.

Also especially preferred are compositions 61.1. to 61.2029 which differ from the corresponding compositions 1.1 to 1.2029 only in that they additionally comprise B.113 as further herbicide B.

Also especially preferred are compositions 62.1. to 62.2029 which differ from the corresponding compositions 1.1 to 1.2029 only in that they additionally comprise B.115 as further herbicide B.

Also especially preferred are compositions 63.1. to 63.2029 which differ from the corresponding compositions 11.1 to 1.2029 only in that they additionally comprise B.116 as further herbicide B.

Also especially preferred are compositions 64.1. to 64.2029 which differ from the corresponding compositions 1.1 to 1.2029 only in that they additionally comprise B.120 as further herbicide B.

Also especially preferred are compositions 65.1. to 65.2029 which differ from the corresponding compositions 1.1 to 1.2029 only in that they additionally comprise B.122 as further herbicide B.

Also especially preferred are compositions 66.1. to 66.2029 which differ from the corresponding compositions 1.1 to 1.2029 only in that they additionally comprise B.123 as further herbicide B.

Also especially preferred are compositions 67.1. to 67.2029 which differ from the corresponding compositions 1.1 to 1.2029 only in that they additionally comprise B.125 as further herbicide B.

Also especially preferred are compositions 68.1. to 68.2029 which differ from the corresponding compositions 1.1 to 1.2029 only in that they additionally comprise B.126 as further herbicide B.

Also especially preferred are compositions 69.1. to 69.2029 which differ from the corresponding compositions 1.1 to 1.2029 only in that they additionally comprise B.133 as further herbicide B.

Also especially preferred are compositions 70.1. to 70.2029 which differ from the corresponding compositions 1.1 to 1.2029 only in that they additionally comprise B.2 as further herbicide B.

Also especially preferred are compositions 71.1. to 71.2029 which differ from the corresponding compositions 1.1 to 1.2029 only in that they additionally comprise B.7 as further herbicide B.

Also especially preferred are compositions 72.1. to 72.2029 which differ from the corresponding compositions 1.1 to 1.2029 only in that they additionally comprise B.29 further herbicide B.

Also especially preferred are compositions 73.1. to 73.2029 which differ from the corresponding compositions 1.1 to 1.2029 only in that they additionally comprise B.30 as further herbicide B.

Hereinbelow, the preparation of the benzoxazinones of the formula I is illustrated by examples; however, the subject matter of the present invention is not limited to the examples given.

EXAMPLE 1

2,2,7-Trifluoro-6-(5-methyl-6-oxo-4-trifluoromethyl-6H-pyridazin-1-yl)-4-prop-2-ynyl-4H-benzo[1,4]oxazin-3-one (compound Ia48)

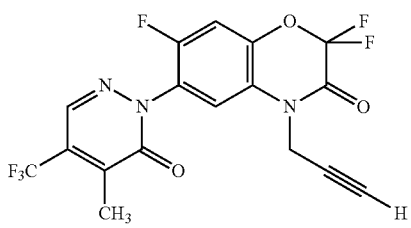 [SMILES: C#CCN1C(=O)C(F)(F)Oc2cc(F)c(-n3ncc(C(F)(F)F)c(C)c3=O)cc21]

Example 1.1

2-Amino-5-fluorophenol

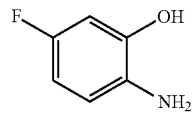

To 5-fluoro-2-nitrophenol (26.63 g, 170 mmol) in ethanol under $N_2$ atmosphere was added palladium on carbon (10 wt %, 250 mg, 0.235 mmol). The mixture was flushed with $H_2$ and stirred at RT under $H_2$ (balloon) until complete conversion according to thin layer chromatography (TLC) analysis. Pd/C was removed by filtration and the filtrate was concentrated to yield 21.6 g of the title compound.

$^1$H NMR (DMSO): 4.5 (br, 2H), 6.35 (dd, 1H), 6.45 (dd, 1H), 6.50 (dd, 1H), 9.5 (br, 1H).

Example 1.2

2-Bromo-2,2-difluoro-N-(4-fluoro-2-hydroxyphenyl)acetamide

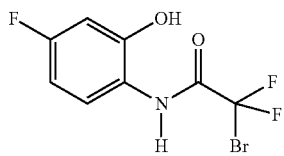 [SMILES: O=C(Nc1ccc(F)cc1O)C(F)(F)Br]

Alternative a)

To 2-amino-5-fluorophenol (14 g, 110 mmol) in dry tetrahydrofuran at 0° C. was added sodium hydride (55 wt % in mineral oil; 4.81 g, 110 mmol). The resulting mixture was stirred for 15 minutes at −15° C. Subsequently ethyl 2-bromo-2,2-difluoroacetate (24.59 g, 121 mmol) was added dropwise and the resulting mixture was stirred at 0° C. for two hours. The reaction mixture was quenched with saturated aqueous $NH_4Cl$ solution and extracted with ethyl acetate. The combined extracts were washed with brine, dried with $Na_2SO_4$ and concentrated to yield 33 g of the title compound.

$^1$H NMR (DMSO): 3.3 (br, 1H), 6.8 (m, 2H), 7.25 (dd, 1H), 10.4 (br, 1H).

Alternative b)

To 2-amino-5-fluorophenol (200 mg, 1.573 mmol) in dry tetrahydrofuran at 0° C. was added sodium hydride (55 wt % in mineral oil, 68.6 mg, 1.573 mmol). The resulting mixture was stirred for 15 minutes at −15° C. Subsequently methyl 2-bromo-2,2-difluoroacetate (327 mg, 1.731 mmol) was added dropwise and the resulting mixture was stirred at 0° C. for two hours. The reaction mixture was quenched in saturated aqueous $NH_4Cl$ solution and extracted with ethyl acetate. The combined extracts were washed with brine, dried with $Na_2SO_4$ and concentrated to yield 450 mg of the title compound $^1$H NMR (DMSO): 3.3 (br, 1H), 6.8 (m, 2H), 7.25 (dd, 1H), 10.4 (br, 1H).

Example 1.3

2,2,7-Trifluoro-2H-benzo[b][1,4]oxazin-3(4H)-one

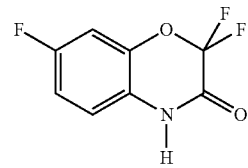

To 2-bromo-2,2-difluoro-N-(4-fluoro-2-hydroxyphenyl)acetamide (33 g, 116 mmol) in dry toluene was added 1,8-diazabicyclo[5.4.0]undec-7-en (DBU, 17.51 ml, 116 mmol). The resulting mixture was stirred overnight at 80° C. The reaction was quenched in saturated aqueous $NH_4Cl$ solution and extracted with ethyl acetate. The combined extracts were washed with brine, dried with $Na_2SO_4$ and concentrated to afford 24.94 g of the title compound.

GCMS m/e (M+)=203

Example 1.4

2,2,7-Trifluoro-6-nitro-2H-benzo[b][1,4]oxazin-3(4H)-one

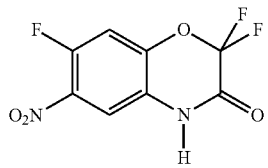

2,2,7-trifluoro-2H-benzo[b][1,4]oxazin-3(4H)-one (2.5 g, 12.31 mmol) was dissolved in sulfuric acid (40 ml, 750 mmol). The reaction mixture was cooled to 0-5° C. Slowly nitric acid (1.761 ml, 39.7 mmol) was added dropwise and the temperature was maintained between 0-5° C. The reaction mixture was stirred for 30 min at this temperature. Then the reaction mixture was added dropwise to vigorously stirred cold water. A solid was formed, which was extracted with dichloromethane. The combined extracts were dried over Na$_2$SO$_4$, and concentrated to yield 2.56 g of the title compound as a brown solid.

GC/MS m/e (M+)=248

$^1$H-NMR (CDCl$_3$): 2.90 (br, 1H), 7.15 (d, 1H), 7.80 (d, 1H).

Example 1.5

2,2,7-Trifluoro-6-nitro-4-(prop-2-ynyl)-2Hbenzo[b][1,4]oxazin-3(4H)-one

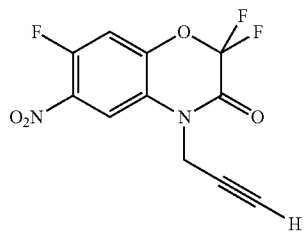 [SMILES: C#CCN1C(=O)C(F)(F)Oc2cc(F)c([N+](=O)[O-])cc21]

To 2,2,7-trifluoro-6-nitro-2H-benzo[b][1,4]oxazin-3(4H)-one (6.9 g, 27.8 mmol) and potassium carbonate (4.61 g, 33.4 mmol) in dry N,N-dimethylformamide at RT was dropwise added 3-bromoprop-1-yne (80 wt % in toluene; 4.96 g, 33.4 mmol). The resulting mixture was stirred at RT overnight. The reaction mixture was poured in saturated aqueous NH$_4$Cl solution and extracted with ethyl acetate. The combined extracts were washed with aqueous NaCl solution, dried with Na$_2$SO$_4$, concentrated and chased with toluene to yield 7.06 g of the title compound as a dark brown solid.

GCMS m/e (M+)=286

Example 1.6

6-Amino-2,2,7-trifluoro-4-(prop-2-ynyl)-2Hbenzo[b][1,4]oxazin-3(4H)-one

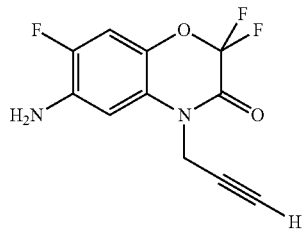

To ammonium chloride (3.96 g, 74.0 mmol) in water was added iron powder (325 mesh; 4.13 g, 74.0 mmol). To the resulting mixture was added 2,2,7-trifluoro-6-nitro-4-(prop-2-ynyl)-2Hbenzo[b][1,4]oxazin-3(4H)-one (7.06 g, 24.67 mmol) in methanol/tetrahydrofuran. The resulting mixture was stirred vigorously at 70° C. for 2 hours. The reaction was quenched in water/ethyl acetate under stirring. The resulting 2 phase system was filtered and the layers were separated. The water layer was subsequently extracted with ethyl acetate. The combined organic phases were washed with brine, dried with Na$_2$SO$_4$ and concentrated to yield 5.15 g of the title compound.

GCMS m/e (M+)=256

Example 1.7

2,2,7-Trifluoro-6-hydrazino-4-prop-2-ynyl-4H-benzo[1,4]oxazin-3-one

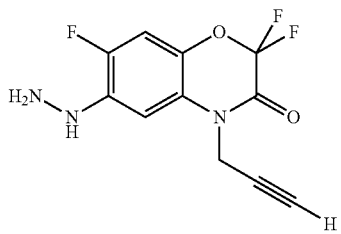 [SMILES: C#CCN1C(=O)C(F)(F)Oc2cc(F)c(NN)cc21]

To a mechanically stirred suspension of 6-amino-2,2,7-trifluoro-4-(prop-2-ynyl)-2H-benzo[b][1,4]oxazin-3(4H)-one (20 g, 78 mmol) in conc. hydrochloric acid (100 ml, 1218 mmol) at −5° C. was added dropwise, over a period of 30 minutes, a solution of sodium nitrite (5.82 g, 84 mmol) in water (40 ml), maintaining the temperature below −5° C. The resulting mixture was stirred at ~0° C. for 1 hour. Subsequently the stirred reaction mixture was cooled to −35° C. with a dry-ice/2-propanol cooling bath. A cooled solution (−10° C.) of tin(II) chloride (37.0 g, 195 mmol) in conc. hydrochloric acid (40 ml, 487 mmol) was added over the course of ca. 1 minute, during which time the temperature increased from −35 to −10° C. The resulting mixture was stirred at 0° C. for 1 hour. Then 80 g kieselguhr was added to the reaction mixture and the resulting mixture was neutralised to pH~7 by slow addition of 10% aqueous NaOH solution under stirring. The whole was filtered and the filter cake and filtrate were extracted twice with diethyl ether. The extracts were washed with brine, dried over Na$_2$SO$_4$ and concentrated in vacuo to yield 17 g of product, having a purity of ca. 85%. Trituration with diisopropyl ether gave 11.87 g of product. A further quantity of 3.6 g of product was obtained by concentration of the mother liquor.

$^1$H NMR (DMSO-d$_4$) δ 7.29-7.26 (m, 2H), 4.80-4.79 (d, 2H), 4.16 (s, 2H), 3.45-3.44 (t, 1H).

Example 1.8

(E)-2,2,7-Trifluoro-4-prop-2-ynyl-6-{N'-[3,3,3-trifluoro-2-oxo-prop-(Z)-ylidene]-hydrazino}-4H-benzo[1,4]oxazin-3-one

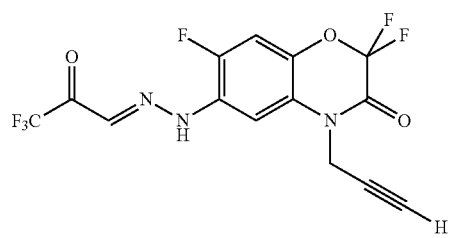 [SMILES: C#CCN1C(=O)C(F)(F)Oc2cc(F)c(N/N=C/C(=O)C(F)(F)F)cc21]

To a stirred solution of sodium acetate (0.865 g, 10.55 mmol) in water (10 ml) was added under ice cooling and under nitrogen atmosphere 3,3-dibromo-1,1,1-trifluoropropan-2-one (1.294 g, 4.79 mmol). Thereafter the reaction was allowed to proceed at 80° C. for one hour. Subsequently the reaction mixture was cooled to 0° C. and 2,2,7-trifluoro-6-hydrazinyl-4-(prop-2-ynyl)-2H-benzo[b][1,4]oxazin-3(4H)-one (1 g, 3.69 mmol) was added in one portion. The reaction mixture changed from a white/beige suspension to a hard yellow suspension. The reaction was continued at room temperature for two hours and the resulting precipitate was collected over a glass filter. The product (yellow powder) was washed with water and heptane and dried on filter. It was used without further purification in the following step.

Example 1.9

2,2,7-Trifluoro-6-(5-methyl-6-oxo-4-trifluoromethyl-6H-pyridazin-1-yl)-4-prop-2-ynyl-4H-benzo[1,4] oxazin-3-one

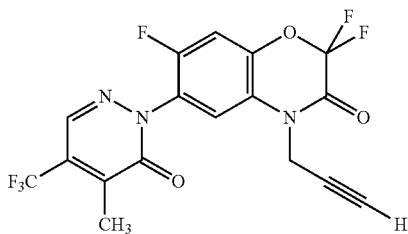 [SMILES: C#CCN1C(=O)C(F)(F)Oc2cc(F)c(-n3ncc(C(F)(F)F)c(C)c3=O)cc21]

To a stirred yellow suspension of (E)-2,2,7-trifluoro-4-(prop-2-ynyl)-6-(2-(3,3,3-trifluoro-2-oxopropylidene)hydrazinyl)-2H-benzo[b][1,4]oxazin-3-one (1399 mg, 3.69 mmol) in dry toluene (20 ml) was added (carbethoxyethylidene)triphenylphosphorane (1738 mg, 4.80 mmol), resulting in a clear orange/red solution. The reaction was continued overnight at reflux under Dean-Stark conditions, while conducting aezotropic dehydration. Thereupon the reaction mixture was concentrated in vacuo to yield 2.99 g of crude product containing ca. 50% triphenylphosphine oxide. The crude product was chromatographed over silica (9:1→1:1 heptane/ethyl acetate) to yield 1.08 g of product (ca. 89% purity). Recrystallisation from diisopropyl ether/heptane gave the title compound as a white powder (purity>99%).

$^1$H NMR (DMSO-d6) δ 8.37 (s, 1H), 7.82-7.78 (m, 2H), 4.82 (d, 2H), 3.47-3.46 (t, 1H), 2.33 (2, 3H).

EXAMPLE 2

(6S,7aR)-6-Fluoro-2-(2,2,7-trifluoro-3-oxo-4-prop-2-ynyl-3,4-dihydro-2H-benzo[1,4]-oxazin-6-yl)-tetrahydro-pyrrolo[1,2-c]imidazole-1,3-dione

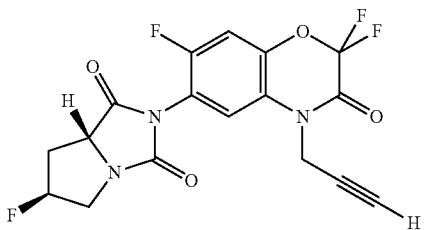 [SMILES: C#CCN1C(=O)C(F)(F)Oc2cc(F)c(N3C(=O)[C@H]4C[C@H](F)CN4C3=O)cc21]

Example 2.1

(1S,4R)-4-Fluoro-2-(2,2,7-trifluoro-3-oxo-4-prop-2-ynyl-3,4-dihydro-2H-benzo[1,4]oxazin-6-ylcarbamoyl)-cyclopentanecarboxylic acid

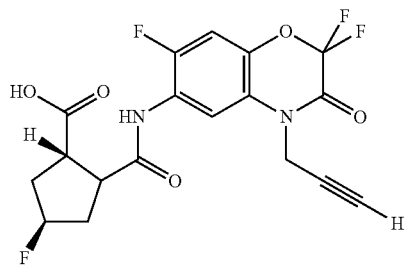 [SMILES: C#CCN1C(=O)C(F)(F)Oc2cc(F)c(NC(=O)C3C[C@@H](F)C[C@@H]3C(=O)O)cc21]

Carbonyl diimidazole (1519 mg, 9.37 mmol) was added to a stirred solution of 6-amino-2,2,7-trifluoro-4-(prop-2-ynyl)-2H-benzo[b][1,4]oxazin-3(4H)-one (the product of Step 1.6 above, 800 mg, 3.12 mmol) and triethylamine (0.457 ml, 3.28 mmol) in anhydrous acetonitrile (15 ml) at room temperature under nitrogen. The resulting mixture was heated to 80° C. Then (2R,4S)-4-fluoropyrrolidine-2-carboxylic acid (416 mg, 3.12 mmol) was added. The resulting suspension was stirred at reflux. After 2 hours a red/brown clear solution was obtained. LCMS analysis indicated that full conversion had occurred. The reaction mixture was gradually cooled to room temperature, poured into 1 N hydrochloric acid and extracted three times with ethyl acetate. The combined organic extracts were washed with brine, dried over anhydrous sodium sulfate and evaporated in vacuo to yield the desired compound (1.34 g, ca. 90% purity), which was used without further purification in the following step.

Example 2.2

(6S,7aR)-6-Fluoro-2-(2,2,7-trifluoro-3-oxo-4-prop-2-ynyl-3,4-dihydro-2H-benzo[1,4]oxazin-6-yl)-tetrahydro-pyrrolo[1,2-c]imidazole-1,3-dione

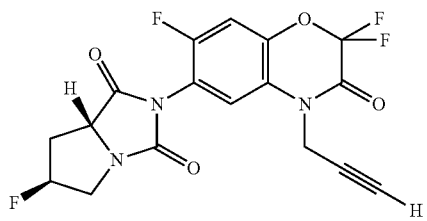 [SMILES: C#CCN1C(=O)C(F)(F)Oc2cc(F)c(N3C(=O)[C@H]4C[C@H](F)CN4C3=O)cc21]

A mixture of (1S,4R)-4-fluoro-2-(2,2,7-trifluoro-3-oxo-4-prop-2-ynyl-3,4-dihydro-2H-benzo[1,4]oxazin-6-ylcarbamoyl)-cyclopentanecarboxylic (1.296 g, 3.12 mmol) and hydrochloric acid (1.56 ml of a 4N solution in dioxane, 6.24 mmol) in dioxane (25 ml) under nitrogen was stirred at 70° C. for 2 hours, and then further overnight, after which time LCMS analysis indicated complete conversion. The reaction mixture was cooled to room temperature and evaporated in vacuo to yield ca. 1.3 g of crude product. This was triturated with di-isopropyl ether and crystallised from a mixture of dichloromethane and n-heptane. Column chromatography of the solid residue (9:1→1:1, n-heptane/ethyl acetate) yielded 868 mg of the title compound (purity>95%).

$^1$H NMR (CDCl$_3$) δ 7.25-7.23 (d, 1H), 7.17-7.15 (d, 1H), 5.60-5.47 (d, 1H, J=52), 4.83-4.72 (q, 2H), 4.67-4.63 (q, 1H), 4.17 (m, 1H), 3.70-3.60 (q, 4H), 2.78-2.69 (m, 1H), 2.40-2.39 (t, 1H), 2.07-1.90 (m, 1H).

EXAMPLE 3

2,2,7-Trifluoro-6-(3-oxo-5,6,7,8-tetrahydro-[1,2,4]triazolo[4,3-a]pyridin-2-yl)-4-prop-2-ynyl-4H-benzo[1,4]oxazin-3-one (compound Ic48)

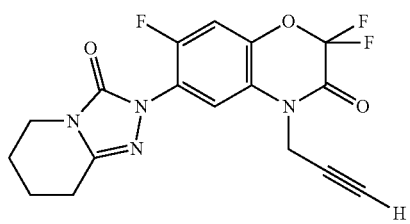 [SMILES: C#CCN1C(=O)C(F)(F)Oc2cc(F)c(-n3nc4n(c3=O)CCCC4)cc21]

Example 3.1

Formic acid N'-(2,2,7-trifluoro-3-oxo-4-prop-2-ynyl-3,4-dihydro-2H-benzo[1,4]oxazin-6-yl)-hydrazide

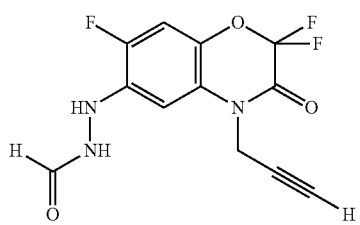 [SMILES: C#CCN1C(=O)C(F)(F)Oc2cc(F)c(NNC=O)cc21]

Formic acid (0.157 ml, 4.09 mmol) was added to 2,2,7-trifluoro-6-hydrazinyl-4-(prop-2-ynyl)-2H-benzo[b][1,4]oxazin-3(4H)-one (the product of Step 1.7 above, 1.0 g, 3.69 mmol) in dichloromethane at room temperature under stirring. The mixture was then stirred overnight at room temperature. The resulting precipitate was isolated over a glass filter and washed with diisopropyl either to yield 858 mg of product (>95% purity), which was used without further purification.

Example 3.2

6-chloro-3,4-dihydropyridine-1(2H)-carbonyl chloride

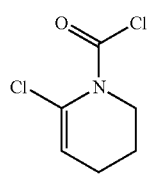

To stirred diphosgene (3.10 ml, 25.7 mmol) at ~−20° C. (cooled with a dry ice/2-propanol bath) under nitrogen was added activated carbon (0.25 g), which caused some phosgene gas to be liberated. To the resulting stirred mixture was added very slowly dropwise piperidin-2-one (2.55 g, 25.7 mmol) in ethyl acetate (dried over molecular sieves) (7 ml) over 1 hour, while keeping the temperature below 0° C.

Thereafter the reaction was stirred at room temperature for 2 hours, whereupon the reaction was found to be complete according to TLC analysis. The reaction mixture was filtered to remove precipitate and activated carbon, and then washed with dry ethyl acetate. The filtrate was concentrated in vacuo (flushed with Argon) to yield 1.87 g of product as a yellow cloudy oil, which is used without further purification in the following step.

Example 3.3

2,2,7-Trifluoro-6-(3-oxo-5,6,7,8-tetrahydro-[1,2,4]triazolo[4,3-a]pyridin-2-yl)-4-prop-2-ynyl-4H-benzo[1,4]oxazin-3-one

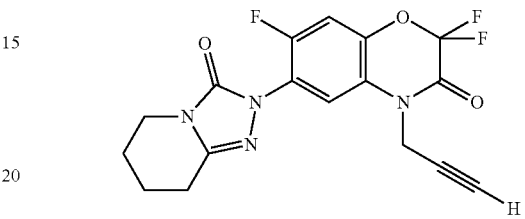

To an ice-bath cooled yellow/brown suspension of N'-(2,2,7-trifluoro-3-oxo-4-(prop-2-ynyl)-3,4-dihydro-2H-benzo[b][1,4]oxazin-6-yl)formohydrazide (850 mg, 2.84 mmol) in anhydrous acetonitrile (35 ml) was added dropwise 6-chloro-3,4-dihydropyridine-1(2H)carbonyl chloride (614 mg, 3.41 mmol) in anhydrous acetonitrile (1 ml), maintaining the temperature below 10° C. Thereafter, triethylamine (0.792 ml, 5.68 mmol) was added dropwise and stirring was continued at ~10° C. for one hour, resulting in a clear red solution. The reaction was than stirred for 2 hours at 50° C., after which time TLC analysis indicated that the reaction was complete. 6N hydrochloric acid (4.26 ml, 25.6 mmol) was added dropwise and the resulting mixture was stirred at 50° C. for one hour. The reaction mixture was subsequently poured into ~250 ml water and the whole was extracted three times with ethyl acetate. The combined organic layers were washed with brine and dried over Na$_2$SO$_4$. The organic phase was subsequently concentrated in vacuo to yield 950 mg of crude product. Chromatography (2:1→1:9 hexane/ethyl acetate) yielded 550 mg of product (92% purity). Trituration with diisopropyl ether provided 440 mg of the title compound (purity>95%).

$^1$H NMR (CDCl$_3$) δ 7.52-7.50 (d, 1H), 7.15-7.13 (d, 1H), 4.79-4.78 (d, 2H), 3.74-3.71 (t, 2H), 2.81-2.78 (t, 2H), 2.37-2.36 (t, 1H), 2.04-1.95 (m, 4H)

EXAMPLE 4

5-Isopropylidene-3-(2,2,7-trifluoro-3-oxo-4-prop-2-ynyl-3,4-dihydro-2H-benzo[1,4]oxazin-6-yl)-oxazolidine-2,4-dione (compound Ie48)

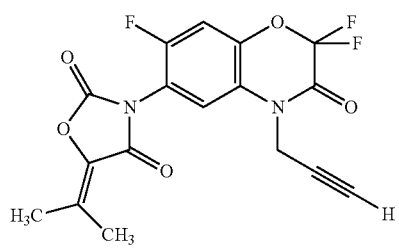 [SMILES: C#CCN1C(=O)C(F)(F)Oc2cc(F)c(N3C(=O)OC(=C(C)C)C3=O)cc21]

Example 4.1

Ethyl 3,3-dimethyl-oxirane-2-carboxylate

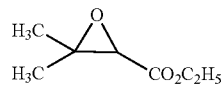

To a stirred solution of propan-2-one (11.52 ml, 157 mmol) and ethyl 2-chloroacetate (25.04 ml, 235 mmol) in dry diethyl ether (125 ml) at −10° C. under nitrogen was added sodium ethoxide (10.66 g, 157 mmol) portionwise, keeping the temperature below 5° C. After addition was complete, the mixture was stirred for two hours at −10° C., whereafter the reaction was continued at room temperature for three hours. The reaction mixture was quenched with saturated aqueous ammonium chloride, the phases were separated, and the aqueous layer was extracted with diethyl ether (100 ml). The combined organic phases were dried over $Na_2SO_4$ and evaporated in vacuo). The resulting residue was purified by vacuum distillation. The major fraction (~25 mbar, 82° C.-85° C., 14.3 g) consisted of the desired product, containing 6.4 mol % ethyl chloroacetate. This was used in the next step without further purification.

$^1$H NMR ($CDCl_3$) δ 4.32-4.20 (m, 2H), 1.43-1.39 (d, 6H), 1.33-1.30 (t, 3H).

Example 4.2

Ethyl 2-hydroxy-3-methylbut-3-enoate

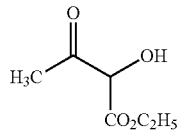

Tosic acid monohydrate (0.132 g, 0.694 mmol) was dehydrated by aezotropic distillation with benzene (3×10 ml) in a rotary evaporator flushed with nitrogen. Thereafter benzene (100 ml) and ethyl 3,3-dimethyloxirane-2-carboxylate (1 g, 6.94 mmol) were added and the resulting mixture was stirred at reflux (81° C.) overnight. The clear reaction mixture was then cooled to room temperature, cooled to 4° C. for a couple of hours, and then filtered over a glass filter to remove the crystallized tosic acid. The filtrate was concentrated in vacuo (40° C., 50 mbar) to yield 778 mg of crude product (containing 2.5 wt % benzene) which was used without further purification in the next step.

$^1$H NMR ($CDCl_3$) δ 5.14 (d, 1H), 5.04 (s, 1H), 4.56 (s, 1H), 4.30-4.24 (q, 2H), 2.51 (br. S, 1H), 1.75 (s, 3H), 1.32-1.29 (t, 3H)

Example 4.3

5-Isopropylidene-3-(2,2,7-trifluoro-3-oxo-4-prop-2-ynyl-3,4-dihydro-2H-benzo[1,4]oxazin-6-yl)-oxazolidine-2,4-dione

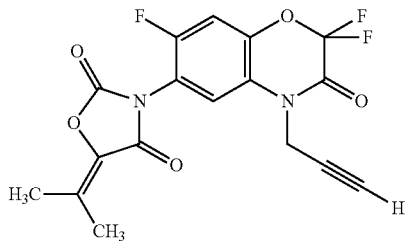

To a stirred solution of 6-amino-2,2,7-trifluoro-4-(prop-2-ynyl)-2H-benzo[b][1,4]oxazin-3(4H)-one (the product of Step 1.6 above, 810 mg, 3.16 mmol) and triethylamine (0.463 ml, 3.32 mmol) in anhydrous acetonitrile (20 ml) under nitrogen was added carbonyl diimidazole (1026 mg, 6.33 mmol). The resulting mixture was heated to 60° C. Thereupon ethyl 2-hydroxy-3-methylbut-3-enoate (456 mg, 3.16 mmol) in 1 ml dry acetonitrile was added. The reaction was heated to reflux, and the reaction was monitored by LCMS until all the starting material had been consumed. The reaction mixture was then diluted with ethyl acetate and washed with 1N hydrochloric acid. The aqueous phase was extracted twice with ethyl acetate, and the combined organic phases were washed with brine, dried over $Na_2SO_4$ and concentrated in vacuo to yield 1.34 g of crude product. Column chromatography (silica, 9:1→2:1, hexane/ethyl acetate) yielded 573 mg of product, containing 24% ethyl carbamate product). Recrystallization from dichloromethane/n-heptane afforded 322 mg of the title compound (purity>95%).

$^1$H NMR ($CDCl_3$) δ 7.30-7.28 (d, 1H), 7.21-7.18 (d, 1H), 4.79-4.78 (d, 2H), 2.40-2.39 (t, 1H), 2.32 (s, 3H), 2.09 (s, 3H).

EXAMPLE 5

7-Fluoro-6-[3-oxo-tetrahydro-[1,3,4]thiadiazolo[3,4-a]pyridazin-(1Z)-ylideneamino]-4-prop-2-ynyl-4H-benzo[1,4]oxazin-3-one (compound If48)

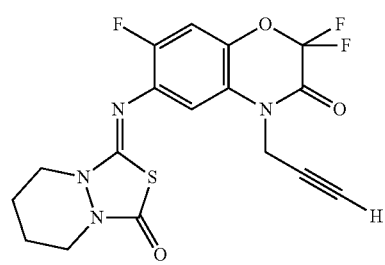 [SMILES: C#CCN1C(=O)C(F)(F)Oc2cc(F)c(/N=c3\sc(=O)n4n3CCCC4)cc21]

Example 5.1

2,2,7-Trifluoro-6-isothiocyanato-4-(prop-2-ynyl)-2H-benzo[b][1,4]oxazin-3(4H)-one

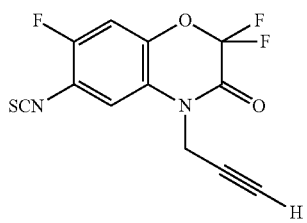

Sodium bicarbonate (4.10 g, 48.8 mmol) was added to a stirred solution of 6-amino-2,2,7-trifluoro-4-(prop-2-ynyl)-2H-benzo[b][1,4]oxazin-3(4H)-one (the product of Step 1.6 above, 5.0 g, 19.52 mmol) in absolute ethanol (100 ml) at 0° C. under nitrogen. Thereafter thiophosgene (1.795 ml, 23.42 mmol) was added dropwise under ice-bath cooling, keeping the temperature of the reaction mixture below 10° C. After the addition was complete, the reaction mixture was stirred for 1 h at room temperature, by which time, according to TLC analysis, the reaction was complete. The salts were removed by filtration and washed with ethyl acetate. The filtrate was concentrated in vacuo to yield 6.55 g of crude product, containing ca. 30% ethyl carbamate. Recrystallisation from dichloromethane afforded 3.84 g of the desired product (>90% purity), which was used without further purification.

Example 5.2

Piperazine-1,2-diium chloride

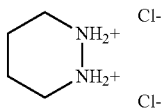

A solution of di-tert-butyl hydrazine-1,2-dicarboxylate (10 g, 43.1 mmol) in dry N,N-dimethylformamide (25 ml) was added to a stirred suspension of sodium hydride (3.79 g of a 60% suspension in mineral oil, 95 mmol) in dry N,N-dimethylformamide (175 ml) at 0° C. under nitrogen. The reaction mixture was stirred for 30 minutes and then 1,4-dibromobutane (9.3 g, 43.1 mmol) was added within half a minute. The reaction was stirred at room temperature overnight. Then water (~20 ml) was added carefully to the reaction mixture at room temperature, and stirring was continued for ca. 5 minutes. Thereafter the quenched reaction mixture was poured into 1 liter of water. The product was extracted twice with diethyl ether (200 ml), and the combined organic layers were washed with three times with 10% aqueous sodium chloride solution, dried over anhydrous sodium sulfate, and concentrated in vacuo to give 14 g of crude tetrahydropyridazine-1,2-dicarboxylic acid di-tert-butyl ester. This was dissolved in diethyl ether (200 ml) and 4N hydrochloric acid in dioxane (108 ml, 431 mmol) was added. The resulting mixture was stirred overnight at room temperature. The thus formed white precipitate was isolated by filtration and dried under a flow of nitrogen to yield 4.6 g of crude product. Analysis by $^1$H NMR indicated that the reaction had not gone to completion. This crude product was combined with the crude product of a similar preparation, dissolved in dichloromethane (200 ml) and treated with 4N hydrochloric acid in dioxane (60 ml, 240 mmol) and the resulting mixture was stirred overnight at room temperature. The reaction mixture was concentrated in vacuo and triturated with dry diethyl ether. The resulting precipitate was isolated by filtration and dried and a flow of nitrogen to yield 6.3 g of product, which was used without further purification in the next step.

$^1$H NMR (DMSO-$d_4$) δ 8.85 (broad s, 4H), 3.00 (s, 4H), 1.69 (s, 4H)

Example 5.3

7-Fluoro-6-[3-oxo-tetrahydro-[1,3,4]thiadiazolo[3,4-a]pyridazin-(1Z)-ylideneamino]-4-prop-2-ynyl-4H-benzo[1,4]oxazin-3-one (compound If48)

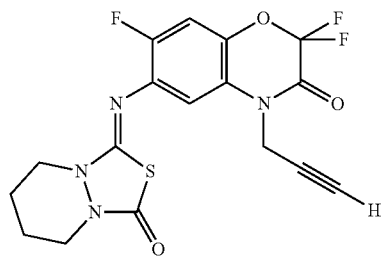

Triethylamine (1.402 ml, 10.06 mmol) was added to a stirred suspension of piperazine-1,2-diium chloride (0.587 g, 3.69 mmol) in dichloromethane (5 ml) at room temperature under nitrogen. This resulted in a thick white barely stirrable suspension. Hereto was dropwise added 2,2,7-trifluoro-6-isothiocyanato-4-(prop-2-ynyl)-2H-enzo[b][1,4]oxazin-3(4H)-one (the product of Step 4.1 above, 1 g, 3.35 mmol) in dichloromethane (5 ml). The resulting mixture was stirred at room temperature for 1 h, by which time TLC analysis indicated that the reaction was complete. The reaction mixture was concentrated in vacuo to yield crude product. It was then triturated with water to remove salts. The thus formed precipitate was isolated by filtration, washed with water and dried to yield 1.19 g of the title compound as a white powder (purity>95%).

$^1$H NMR (DMSO-$d_4$) δ 10.03 (s, 1H), 7.92-7.90 (d, 1H), 7.55-7.52 (d, 1H), 5.37-5.34 (t, 1H), 4.78 (s, 2H), 4.15 (broad s, 2H), 3.45 (s, 1H), 2.88-2.87 (d, 2H), 1.68-1.61 (m, 4H) MS (m/z), M+H: 411.0

EXAMPLE 6

6-(5-tert-Butyl-2-oxo-[1,3,4]oxadiazol-3-yl)-2,2,7-trifluoro-4-prop-2-ynyl-4H-benzo[1,4]oxazin-3-one (compound Ig48)

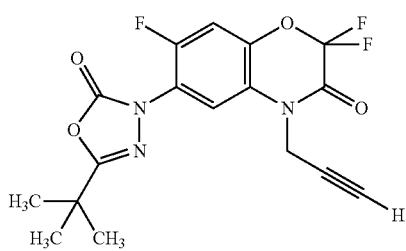 [SMILES: C#CCN1C(=O)C(F)(F)Oc2cc(F)c(-n3nc(C(C)(C)C)oc3=O)cc21]

Example 6.1

2,2-Dimethyl-propionic acid N'-(2,2,7-trifluoro-3-oxo-4-prop-2-ynyl-3,4-dihydro-2H-benzo[1,4]oxazin-6-yl)-hydrazide

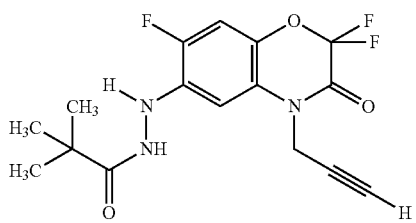 [SMILES: C#CCN1C(=O)C(F)(F)Oc2cc(F)c(NNC(=O)C(C)(C)C)cc21]

Pivalic anhydride (0.687 g, 3.69 mmol) was added dropwise to a stirred solution of 2,2,7-trifluoro-6-hydrazinyl-4-(prop-2-ynyl)-2H-benzo[b][1,4]oxazin-3(4H)-one (the product of Step 1.7 above, 1.0 g, 3.69 mmol) in dichloromethane at room temperature under nitrogen. The resulting mixture was stirred at room temperature for 1 hour, by which time TLC analysis indicated that the reaction was complete. The reaction mixture was diluted with dichloromethane, and washed with 1N aqueous hydrochloric acid. The aqueous layer was extracted with dichloromethane, and the combined organic phases were dried over anhydrous sodium sulfate and evaporated in vacuo to yield 1.55 g of crude product, which was used without further purification in the following step.

Example 6.2

6-(5-tert-Butyl-2-oxo-[1,3,4]oxadiazol-3-yl)-2,2,7-trifluoro-4-prop-2-ynyl-4H-benzo[1,4]oxazin-3-one

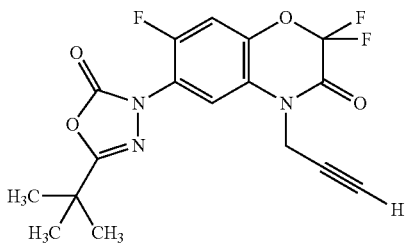 [SMILES: C#CCN1C(=O)C(F)(F)Oc2cc(F)c(-n3nc(C(C)(C)C)oc3=O)cc21]

Diphosgene (0.445 ml, 3.69 mmol) was added dropwise to a stirred solution of N'-(2,2,7-trifluoro-3-oxo-4-(prop-2-ynyl)-3,4-dihydro-2H-benzo[b][1,4]oxazin-6-yl)pivalohydrazide (1311 mg, 3.69 mmol) in dry toluene (30 ml) at room temperature under nitrogen. The resulting mixture was stirred at reflux for 4 hours. It was then cooled to room temperature and evaporated in vacuo to yield 1.7 g of crude product. Trituration of this with diisopropyl ether afforded 990 mg of the title compound as a white powder (purity>95%).

$^1$H NMR (DMSO-$d_6$) δ 7.83-7.80 (m, 2H), 4.83 (d, 2H), 3.50 (s, 1H), 1.32 (s, 9H).

EXAMPLE 7

1-Propyl-2-thioxo-3-(2,2,7-trifluoro-3-oxo-4-prop-2-ynyl-3,4-dihydro-2H-benzo[1,4]oxazin-6-yl)-imidazolidine-4,5-dione (compound Ii48)

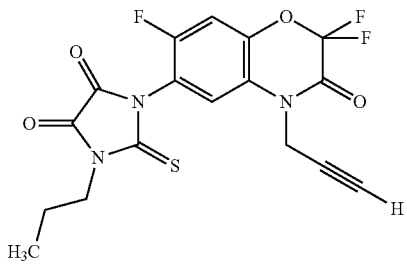

Example 7.1

1-Propyl-3-(2,2,7-trifluoro-3-oxo-4-prop-2-ynyl-3,4-dihydro-2H-benzo[1,4]oxazin-6-yl)-thiourea

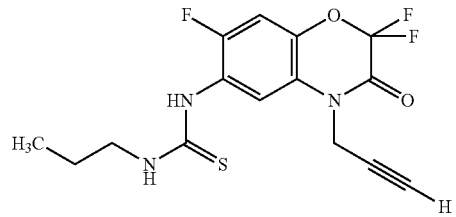 [SMILES: C#CCN1C(=O)C(F)(F)Oc2cc(F)c(NC(=S)NCCC)cc21]

Propan-1-amine (0.937 ml, 11.74 mmol) was added to a stirred solution of 2,2,7-trifluoro-6-isothiocyanato-4-(prop-2-ynyl)-2H-benzo[b][1,4]oxazin-3(4H)-one (the product of Step 4.1 above, 1.0 g, 3.35 mmol) in dichloromethane (10 ml) at room temperature under nitrogen. The resulting mixture was stirred at room temperature for 1 hour, by which time TLC analysis indicated that the reaction was complete. The reaction mixture was evaporated in vacuo to yield 1.3 g of the desired product (purity>95%), which was used without further purification in the next step.

Example 7.2

1-Propyl-2-thioxo-3-(2,2,7-trifluoro-3-oxo-4-prop-2-ynyl-3,4-dihydro-2H-benzo[1,4]oxazin-6-yl)-imidazolidine-4,5-dione

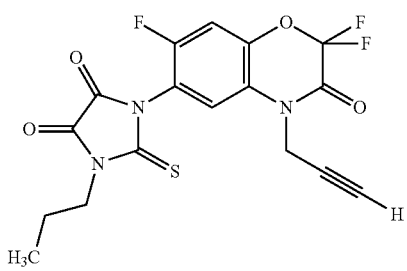 [SMILES: C#CCN1C(=O)C(F)(F)Oc2cc(F)c(N3C(=O)C(=O)N(CCC)C3=S)cc21]

Ethyl oxalyl chloride (0.487 ml, 4.36 mmol) was added to a stirred solution of 1-propyl-3-(2,2,7-trifluoro-3-oxo-4-(prop-2-ynyl)-3,4-dihydro-2H-benzo[b][1,4]oxazin-6-yl)thiourea (1197 mg, 3.35 mmol) in dichloromethane (20 ml) at room temperature under nitrogen. The resulting mixture was stirred overnight at room temperature, and then evaporated in vacuo. Toluene was added to the yellow residue, and the resulting suspension was refluxed for 3 hours, resulting in a clear solution. The reaction mixture was cooled to room temperature, and the resulting precipitate was isolated and washed with heptane to yield 792 mg of crude product. This was then recrystallised from toluene. Some remaining impurity was removed by dissolving the solid in ethyl aceate, washing with aqueous sodium bicarbonate solution, drying over sodium sulfate, and evaporating in vacuo to yield 667 mg of the title compound (purity>95%).

$^1$H NMR (DMSO-$d_6$) δ 7.83-7.80 (d, 1H), 7.66-7.64 (d, 1H), 4.77-4.67 (d, 2H), 3.91-3.80 (t, 2H), 3.52-3.51 (t, 1H), 1.75-1.66 (m, 2H), 0.97-0.93 (t, 3H).

EXAMPLE 8

1-Methyl-3-(2,2,7-trifluoro-3-oxo-4-prop-2-ynyl-3,4-dihydro-2H-benzo[1,4]oxazin-6-yl)-1H-quinazoline-2,4-dione (compound Ik48)

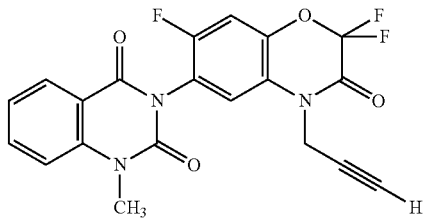 [SMILES: C#CCN1C(=O)C(F)(F)Oc2cc(F)c(-n3c(=O)c4ccccc4n(C)c3=O)cc21]

Carbonyl diimidazole (1.266 g, 7.81 mmol) was added to a stirred solution of 6-amino-2,2,7-trifluoro-4-(prop-2-ynyl)-2H-benzo[b][1,4]oxazin-3(4H)-one (the product of Step 1.6 above, 1.0 g, 3.90 mmol) and triethylamine (0.571 ml, 4.10 mmol) in anhydrous acetonitrile (20 ml) at room temperature under nitrogen. The resulting mixture was heated to 60° C., and then methyl 2-(methylamino)benzoate (0.602 ml, 4.10 mmol) was added. The reaction was heated to reflux for 1 h, after which time the LCMS analysis of a small sample that was subjected to quenching with benzylamine followed by aqueous acidic work up indicated that the reaction was complete. The reaction mixture was then poured into a stirred mixture of ethyl acetate (100 ml) and 1N aqueous hydrochloric acid (100 ml). The phases were separated and the aqueous phase was extracted with ethyl acetate. The combined organic phases were washed with brine, dried over anhydrous sodium sulfate and evaporated in vacuo to yield 1.69 g of crude product. This was triturated overnight with dichloromethane, and the resulting precipitate was filtered off, washed with diisopropyl ether and dried over anhydrous sodium sulfate to give 860 mg of the title compound as an off-white powder.

$^1$H NMR (CDCl$_3$) δ 8.11-8.09 (d, 1H), 7.91-7.88 (t, 1H), 7.78-7.77 (t, 1H), 7.75 (s, 1H), 7.59 (d, 1H), 7.41-7.37 (t, 1H), 4.80-4.71 (d, 2H), 3.58 (s, 3H), 3.45 (s, 1H)).

Further benzoxazinones of formula I have been prepared in accordance to the processes described above, and are, in addition to the compounds mentioned above, listed in table 2 below:

| Example No. | compound | $^1$H NMR (400 MHz; CDCl$_3$) or MS (m/z) M + H |
|---|---|---|
| 9 | | 379.2 |
| 10 | | 7.28 (d, 1H); 7.19 (d, 1H); 4.78 (s, 2H); 2.40 (s, 1H); 2.32 (s, 3H); 2.09 (s, 3H) |
| 11 | | 7.44 (d, 1H); 7.16 (d 1H); 7.07 (t, 1H); 4.79 (s, 2H); 2.39 (s, 1H)1.59 (s, 3H) |

| Example No. | compound | $^1$H NMR (400 MHz; CDCl$_3$) or MS (m/z) M + H |
|---|---|---|
| 12 | | 389.0 |
| 13 | | 409.9 |
| 14 | | 367.0 |
| 15 | | 8.0 (m, 1H); 7.7 (m, 1H); 7.5 (m, 1H); 7.3 (m, 1H); 7.2 (m, 1H); 4.79 (s, 2H); 2.39 (s, 1H) |
| 16 | | 422.0 |
| 17 | | 379.0 |

| Example No. | compound | ¹H NMR (400 MHz; CDCl₃) or MS (m/z) M + H |
|---|---|---|
| 18 | [structure] | 405.0 |
| 19 | [structure] | 352.0 |

USE EXAMPLES

The herbicidal activity of the benzoxazinones of the formula I was demonstrated by the following greenhouse experiments:

The culture containers used were plastic flowerpots containing loamy sand with approximately 3.0% of humus as the substrate. The seeds of the test plants were sown separately for each species.

For the pre-emergence treatment, the active ingredients, which had been suspended or emulsified in water, were applied directly after sowing by means of finely distributing nozzles. The containers were irrigated gently to promote germination and growth and subsequently covered with transparent plastic hoods until the plants had rooted. This cover caused uniform germination of the test plants, unless this has been impaired by the active ingredients.

For the post-emergence treatment, the test plants were first grown to a height of 3 to 15 cm, depending on the plant habit, and only then treated with the active ingredients which had been suspended or emulsified in water. For this purpose, the test plants were either sown directly and grown in the same containers, or they were first grown separately as seedlings and transplanted into the test containers a few days prior to treatment.

Depending on the species, the plants were kept at 10-25° C. or 20-35° C. The test period extended over 2 to 4 weeks. During this time, the plants were tended, and their response to the individual treatments was evaluated.

Evaluation was carried out using a scale from 0 to 100. 100 means no emergence of the plants, or complete destruction of at least the aerial moieties, and 0 means no damage, or normal course of growth. A good herbicidal activity is given at values of at least 70 and a very good herbicidal activity is given at values of at least 85.

The plants used in the greenhouse experiments belonged to the following species:

| Bayer Code | Scientific name |
|---|---|
| ABUTH | Abutilon theophrasti |
| AMAPA | Amaranthus palmeri |
| AMARE | Amaranthus retroflexus |
| CHEAL | Chenopodium album |
| KCHSC | Kochia scoparia |
| MALNE | Malva neglecta |
| VIOAR | Viola arvensis |

At an application rate of 12.5 g/ha the compound Ia48 applied by the post-emergence method showed very good herbicidal activity against *Amaranthus palmeri, Kochia scoparia* and *Malva neglecta*.

At an application rate of 25 g/ha the compound Ia48 applied by the pre-emergence method showed very good herbicidal activity against *Amaranthus retroflexus* and *Viola arvensis*.

At an application rate of 12.5 g/ha the compound Ig48 applied by the post-emergence method showed very good herbicidal activity against *Amaranthus palmeri* and *Malva neglecta*, and a good herbicidal activity against *Kochia scoparia*.

At an application rate of 25 g/ha the compound Ig48 applied by the pre-emergence method showed very good herbicidal activity against *Amaranthus retroflexus* and *Viola arvensis*.

At an application rate of 12.5 g/ha the compound Ii48 applied by the post-emergence method showed very good herbicidal activity against *Kochia scoparia* and *Malva neglecta*.

At an application rate of 12.5 g/ha the compound Ik48 applied by the post-emergence method showed very good herbicidal activity against *Amaranthus palmeri, Kochia scoparia* and *Malva neglecta*.

At an application rate of 25 g/ha the compound Ik48 applied by the pre-emergence method showed very good herbicidal activity against *Amaranthus retroflexus*, and a good herbicidal activity against *Viola arvensis*.

At an application rate of 50 g/ha the compound If48 applied by the pre-emergence method showed very good herbicidal activity against *Abutilon theophrasti, Amaranthus retroflexus* and *Chenopodium album*.

At an application rate of 50 g/ha example 2 applied by the pre-emergence method showed very good herbicidal activity against *Abutilon theophrasti, Amaranthus retroflexus* and *Chenopodium album.*

At an application rate of 50 g/ha example 9 applied by the pre-emergence method showed very good herbicidal activity against *Abutilon theophrasti, Amaranthus retroflexus* and *Chenopodium album.*

At an application rate of 50 g/ha example 10 applied by the pre-emergence method showed very good herbicidal activity against *Abutilon theophrasti, Amaranthus retroflexus* and *Chenopodium album.*

At an application rate of 50 g/ha example 11 applied by the pre-emergence method showed very good herbicidal activity against *Abutilon theophrasti, Amaranthus retroflexus* and *Chenopodium album.*

At an application rate of 50 g/ha example 12 applied by the pre-emergence method showed very good herbicidal activity against *Abutilon theophrasti, Amaranthus retroflexus* and *Chenopodium album.*

At an application rate of 50 g/ha example 13 applied by the pre-emergence method showed very good herbicidal activity against *Amaranthus retroflexus* and *Chenopodium album.*

At an application rate of 50 g/ha example 14 applied by the pre-emergence method showed very good herbicidal activity against *Abutilon theophrasti, Amaranthus retroflexus* and *Chenopodium album.*

At an application rate of 50 g/ha example 15 applied by the pre-emergence method showed very good herbicidal activity against *Amaranthus retroflexus* and *Chenopodium album.*

At an application rate of 50 g/ha example 16 applied by the pre-emergence method showed very good herbicidal activity against *Amaranthus retroflexus* and *Chenopodium album.*

At an application rate of 50 g/ha example 17 applied by the pre-emergence method showed very good herbicidal activity against *Amaranthus retroflexus* and *Chenopodium album.*

At an application rate of 1000 g/ha example 19 applied by the past-emergence method showed a very good herbicidal activity against *Abutilon theophrasti.*

The invention claimed is:
1. A compound of formula I

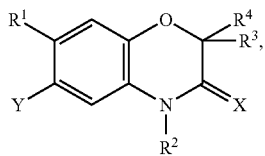

I wherein
$R^1$ is hydrogen or halogen;
$R^2$ is hydrogen, $C_1$-$C_6$-alkyl, $C_1$-$C_6$-haloalkyl, $C_3$-$C_6$-cycloalkyl, $C_3$-$C_6$-alkenyl, $C_3$-$C_6$-haloalkenyl, $C_3$-$C_6$-alkynyl, $C_3$-$C_6$-haloalkynyl, $C_1$-$C_6$-alkoxy or $C_3$-$C_6$-cycloalkyl-$C_1$-$C_6$-alkyl;
$R^3$ is halogen;
$R^4$ is halogen;
X is O or S; and
Y is a substituent selected from the group consisting of $Y^1$ to $Y^{66}$:

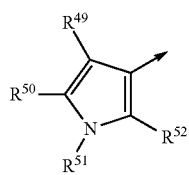

$Y^1$

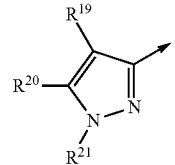

$Y^2$

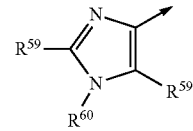

$Y^3$

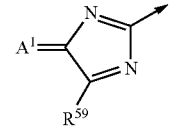

$Y^4$

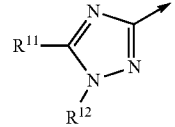

$Y^5$

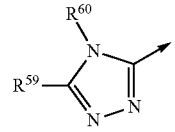

$Y^6$

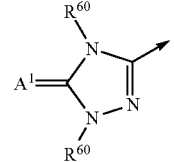

$Y^7$

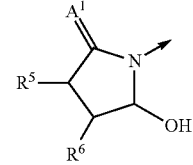

$Y^8$

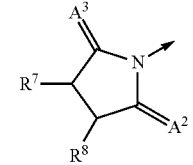

$Y^9$

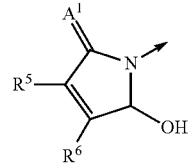

$Y^{10}$

-continued
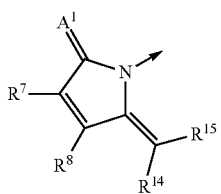
Y¹¹
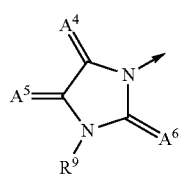
Y¹²
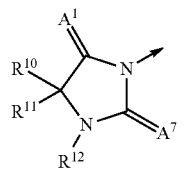
Y¹³
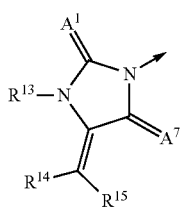
Y¹⁴
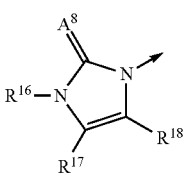
Y¹⁵
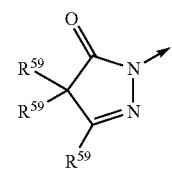
Y¹⁶
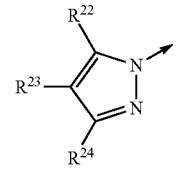
Y¹⁷
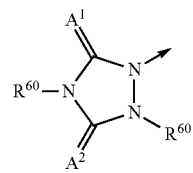
Y¹⁸
-continued
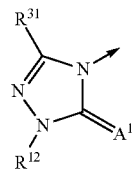
Y¹⁹
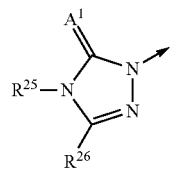
Y²⁰
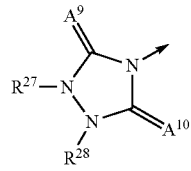
Y²¹
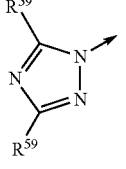
Y²²
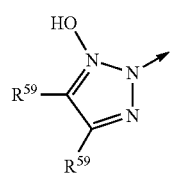
Y²³
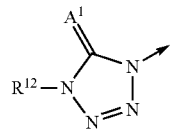
Y²⁴
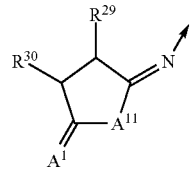
Y²⁵
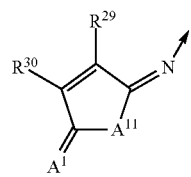
Y²⁶
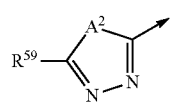
Y²⁷

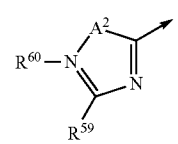 Y28
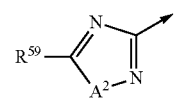 Y29
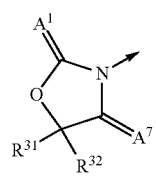 Y30
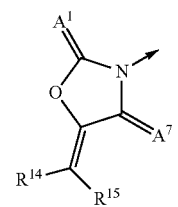 Y31
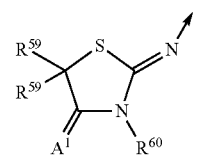 Y32
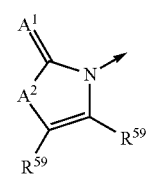 Y33
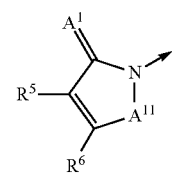 Y34
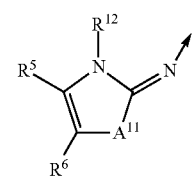 Y35
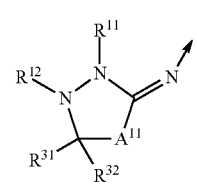 Y36
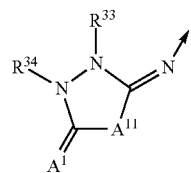 Y37
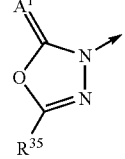 Y38
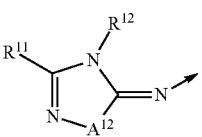 Y39
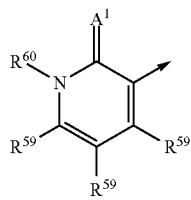 Y40
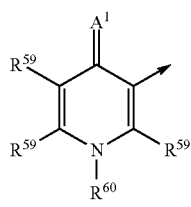 Y41
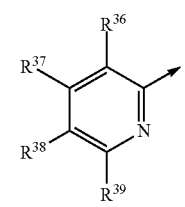 Y42
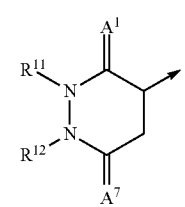 Y43
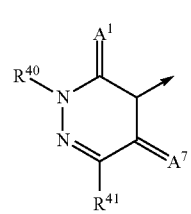 Y44

-continued
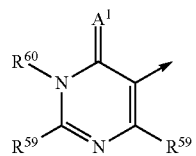 Y⁴⁵
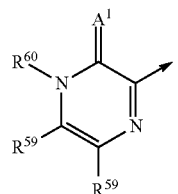 Y⁴⁶
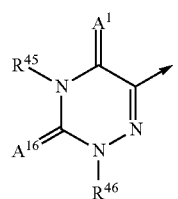 Y⁴⁷
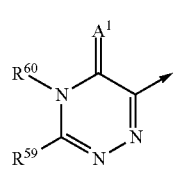 Y⁴⁸
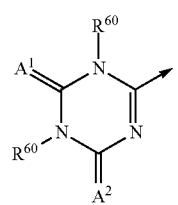 Y⁴⁹
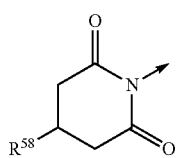 Y⁵⁰
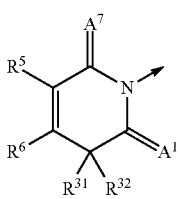 Y⁵¹
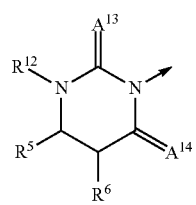 Y⁵²
-continued
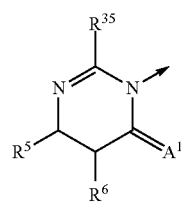 Y⁵³
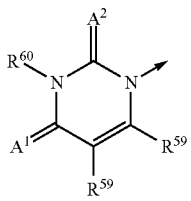 Y⁵⁴
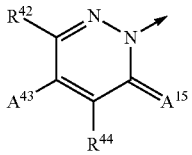 Y⁵⁵
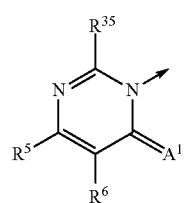 Y⁵⁶
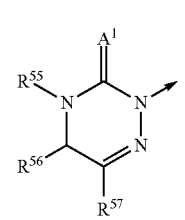 Y⁵⁷
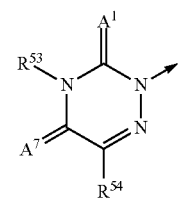 Y⁵⁸
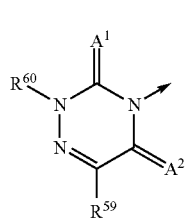 Y⁵⁹
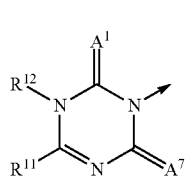 Y⁶⁰

-continued

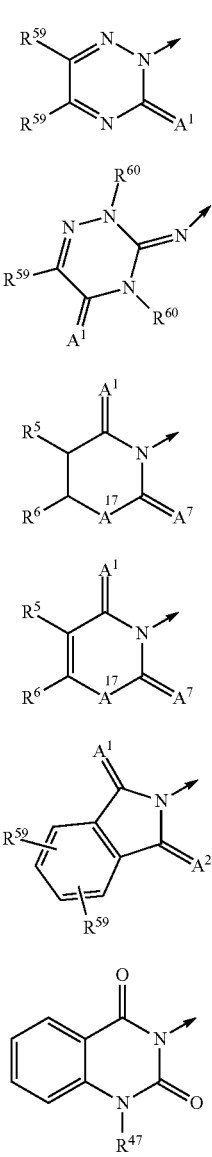

wherein
$A^1$ to $A^{10}$ are oxygen or sulfur;
$A^{11}$ is oxygen, sulphur, SO or $SO_2$;
$A^{12}$ to $A^{17}$ are oxygen or sulfur;
$R^5$, $R^6$, $R^7$, $R^8$, $R^{23}$, $R^{24}$, $R^{29}$, $R^{30}$, $R^{37}$, $R^{38}$, $R^{39}$, $R^{43}$, $R^{44}$, $R^{56}$ and $R^{58}$
are hydrogen, hydroxy, $C_1$-$C_6$-alkyl, $C_1$-$C_6$-haloalkyl, $C_3$-$C_7$-cycloalkyl, $C_3$-$C_7$-cycloalkyloxy, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkenyloxy, $C_3$-$C_6$-alkynyl, $C_3$-$C_6$-alkynyloxy, $C_1$-$C_6$-alkylthio, $C_1$-$C_6$-alkylsulfinyl, $C_1$-$C_6$-alkylsulfonyl, $C_1$-$C_6$-alkoxysulfonyl, $C_1$-$C_6$-alkylsulfonyloxy, amino, $C_1$-$C_6$-alkylamino or di($C_1$-$C_6$-alkyl)amino; or
$R^5$ and $R^6$, $R^7$ and $R^8$, $R^{23}$ and $R^{24}$ or $R^{29}$ and $R^{30}$, together with the atoms to which they are attached, form a three- to six-membered cycle, which is saturated, partial unsaturated or aromatic, which may comprise, apart from carbon atoms, one to four nitrogen atoms, or one or two oxygen atoms, or one or two sulfur atoms, or one to three nitrogen atoms and an oxygen atom, or one to three nitrogen atoms and a sulfur atom, or one sulfur and one oxygen atom, and which for its part may be partially or fully halogenated and/or substituted by one to three radicals from the group consisting of $C_1$-$C_6$-alkyl and $C_1$-$C_6$-alkoxy;

$R^9$, $R^{10}$, $R^{11}$, $R^{12}$, $R^{16}$, $R^{17}$, $R^{20}$, $R^{21}$, $R^{25}$, $R^{26}$, $R^{27}$, $R^{28}$, $R^{33}$, $R^{34}$, $R^{40}$, $R^{45}$, $R^{46}$, $R^{50}$, $R^{51}$, $R^{53}$ and $R^{55}$ are hydrogen, cyano, hydroxy, $C_1$-$C_6$-alkyl, $C_1$-$C_6$-cyanoalkyl, $C_1$-$C_6$-haloalkyl, $C_3$-$C_7$-cycloalkyl, $C_3$-$C_7$-cycloalkyloxy, $C_1$-$C_6$-alkoxy, $C_1$-$C_6$-haloalkoxy, $C_2$-$C_6$-alkenyl, $C_2$-$C_6$-haloalkenyl, $C_2$-$C_6$-alkenyloxy, $C_3$-$C_6$-alkynyl, $C_3$-$C_6$-alkynyloxy, $C_1$-$C_6$-alkylsulfinyl, $C_1$-$C_6$-alkylsulfonyl, phenyl-$C_1$-$C_6$-alkyl, amino, $C_1$-$C_6$-alkylamino or di(($C_1$-$C_6$-alkyl)amino; or $R^{11}$ and $R^{12}$, $R^{16}$ and $R^{17}$, $R^{25}$ and $R^{26}$, $R^{27}$ and $R^{28}$, or $R^{33}$ and $R^{34}$, together with the atoms to which they are attached, form a three- to six-membered cycle, which is saturated, partial unsaturated or aromatic, which may comprise, apart from carbon atoms, one to four nitrogen atoms, or one or two oxygen atoms, or one or two sulfur atoms, or one to three nitrogen atoms and an oxygen atom, or one to three nitrogen atoms and a sulfur atom, or one sulfur and one oxygen atom, and which for its part may be partially or fully halogenated and/or substituted by one to three radicals from the group consisting of $C_1$-$C_6$-alkyl and $C_1$-$C_6$-alkoxy;

$R^{13}$ is hydrogen, $C_1$-$C_6$-alkyl, $C_1$-$C_6$-haloalkyl, $C_2$-$C_6$-alkenyl, $C_3$-$C_6$-alkynyl, $C_1$-$C_6$-haloalkoxy, amino, $C_1$-$C_6$-alkylamino or di($C_1$-$C_6$-alkyl)amino;

$R^{14}$, $R^{15}$, $R^{18}$, $R^{22}$, $R^{31}$ and $R^{32}$
are hydrogen, halogen or $C_1$-$C_6$-alkyl;

$R^{19}$, $R^{35}$, $R^{36}$, $R^{41}$, $R^{42}$, $R^{49}$, $R^{52}$, $R^{54}$ and $R^{57}$
are hydrogen, halogen, hydroxy, $C_1$-$C_6$-alkyl, $C_1$-$C_6$-haloalkyl, $C_3$-$C_7$-cycloalkyl, $C_3$-$C_7$-cycloalkyloxy, $C_1$-$C_6$-alkoxy, $C_1$-$C_6$-haloalkoxy, $C_1$-$C_6$-alkylthio, $C_1$-$C_6$-haloalkylthio, $C_2$-$C_6$-alkenyl, $C_2$-$C_6$-haloalkenyl, $C_2$-$C_6$-alkenyloxy, $C_3$-$C_6$-alkynyl or $C_3$-$C_6$-alkynyloxy; and $R^{47}$ is hydrogen, $NH_2$, $C_1$-$C_6$-alkyl or $C_3$-$C_6$-alkynyl;

$R^{59}$ is hydrogen, amino, nitro, cyano, carboxy, carbamoyl, thiocarmbamoyl, halogen, $C_1$-$C_6$-alkyl, $C_1$-$C_6$-haloalkyl, $C_3$-$C_7$-cycloalkyl, $C_3$-$C_7$-cyclo-alkyloxy, $C_1$-$C_6$-alkoxy, $C_1$-$C_6$-haloalkoxy, $C_1$-$C_6$-alkylthio, $C_1$-$C_6$-halo-alkylthio, $C_2$-$C_6$-alkenyl, $C_2$-$C_6$-haloalkenyl, $C_2$-$C_6$-alkenyloxy, $C_3$-$C_6$-alkynyl, $C_3$-$C_6$-alkynyloxy, $C_1$-$C_6$-alkoxycarbonyl, $C_2$-$C_6$-alkenylthio, $C_3$-$C_6$-alkynylthio, $C_1$-$C_6$-alkylamino, di($C_1$-$C_6$-alkyl)amino or $C_3$-$C_7$-cycloalkyl-$C_1$-$C_3$-alkyl;

$R^{60}$ is hydrogen, hydroxyl, amino, cyano, $C_1$-$C_6$-alkyl, $C_1$-$C_6$-haloalkyl, $C_3$-$C_7$-cycloalkyl, $C_3$-$C_7$-cycloalkyloxy, $C_1$-$C_6$-alkoxy, $C_1$-$C_6$-haloalkoxy, $C_2$-$C_6$-alkenyl, $C_3$-$C_6$-alkynyl, $C_1$-$C_6$-alkoxycarbonyl, $C_1$-$C_6$-alkylamino, di($C_1$-$C_6$-alkyl)amino, $C_3$-$C_7$-cycloalkyl-$C_1$-$C_3$-alkyl, phenyl or phenyl-$C_1$-$C_6$-alkyl;

wherein in case Y is $Y^2$ or $Y^{20}$, $R^3$ and $R^4$ both are halogen;
or an agriculturally acceptable salt thereof.

2. The compound of claim 1, wherein $R^1$ is halogen.

3. The compound of claim 1, wherein $R^2$ is $C_3$-$C_6$-alkynyl or $C_3$-$C_6$-haloalkynyl.

4. The compound of claim 1, wherein Y is $Y^2$, $Y^{42}$ or $Y^{55}$.

5. A herbicidal composition comprising a herbicidal active amount of a compound of claim 1 and at least one further active compound selected from the group of the herbicides B and/or safeners C.

6. The composition according to claim 5 comprising at least two further active compounds selected from the group of the herbicides B and/or safeners C.

7. The composition according to claim 6 further comprising at least one inert liquid and/or solid carrier and, if appropriate, at least one surface-active substance.

8. The composition of claim 6 wherein $R^1$ is halogen.

9. The composition of claim 6 wherein $R^2$ is $C_3$-$C_6$-alkynyl or $C_3$-$C_6$-haloalkynyl.

10. The composition of claim 6 wherein Y is $Y^2$, $Y^{42}$ or $Y^{55}$.

11. A herbicidal composition comprising a herbicidal active amount of a compound of claim 1 and at least one inert liquid and/or solid carrier and, if appropriate, at least one surface-active substance.

12. A process for the preparation of herbicidal active compositions, which comprises mixing a herbicidal active amount of a compound of claim 1 and at least one inert liquid and/or solid carrier and, if desired, at least one surface-active substance.

13. A method of controlling undesired vegetation, which comprises allowing a composition comprising a herbicidal active amount of a compound of claim 1 to act on plants, their environment or on seed.

14. The method of claim 13, wherein the composition further comprises at least two further active compounds selected from the group of the herbicides B and/or safeners C.

15. The method of claim 14, wherein the composition further comprises at least one inert liquid and/or solid carrier and, if appropriate, at least one surface-active substance.

16. The method of claim 15, wherein $R^1$ is halogen.

17. The method of claim 15, wherein $R^2$ is $C_3$-$C_6$-alkynyl or $C_3$-$C_6$-haloalkynyl.

18. The method of claim 15, wherein Y is $Y^2$, $Y^{42}$ or $Y^{55}$.

\* \* \* \* \*